United States Patent [19]

Miyake et al.

[11] Patent Number: 5,506,238

[45] Date of Patent: Apr. 9, 1996

[54] BIPHENYLMETHANE DERIVATIVE AND PHARMACOLOGICAL USE

[75] Inventors: Kazutoshi Miyake; Masayuki Matsukura; Naoki Yoneda, all of Ibaraki; Osamu Hiroshima, Chiba; Nobuyuki Mori, Ibaraki; Hiroki Ishihara; Takashi Musha, Ibaraki; Toshiyuki Matsuoka, Ibaraki; Sachiyuki Hamano, Tokyo; Norio Minami, Ibaraki, all of Japan

[73] Assignee: Eisai Co., Ltd., Tokyo, Japan

[21] Appl. No.: 877,113

[22] Filed: May 1, 1992

Related U.S. Application Data

[62] Division of Ser. No. 846,950, Mar. 6, 1992, Pat. No. 5,298,518, which is a division of Ser. No. 675,155, Mar. 26, 1991, abandoned, which is a continuation-in-part of Ser. No. 583,025, Sep. 13, 1990, Pat. No. 5,328,911.

[30] Foreign Application Priority Data

Sep. 29, 1989 [JP] Japan ..................... 1-251761
Dec. 27, 1989 [JP] Japan ..................... 1-336640

[51] Int. Cl.$^6$ ..................... A61K 31/435; C07D 471/04
[52] U.S. Cl. ............................................. 514/303; 546/118
[58] Field of Search ............................ 546/118; 514/303

[56] References Cited

U.S. PATENT DOCUMENTS

| | | | |
|---|---|---|---|
| 4,880,804 | 11/1989 | Carini et al. | 514/234.5 |
| 5,102,880 | 4/1992 | Chakravarty et al. | 544/184 |

FOREIGN PATENT DOCUMENTS

| | | |
|---|---|---|
| 0253310 | 1/1988 | European Pat. Off. |
| 0291969 | 11/1988 | European Pat. Off. |
| WO9312095 | 6/1993 | WIPO |
| WO9405661 | 3/1994 | WIPO |

OTHER PUBLICATIONS

Chemical Abstract, vol. 94, No. 9, 2 Mar. 1981, Columbus, Ohio, Abstract No. 65554u (p. 717).
Chemical Abstract, vol. 101, No. 5, 30 Jul. 1984, Columbus, Ohio, Abstract No. 35051 (p. 220).

*Primary Examiner*—Bernard Dentz
*Attorney, Agent, or Firm*—Birch, Stewart, Kolasch & Birch

[57] ABSTRACT

The biphenylmethane derivative having the formula (I) is useful to prevent and treat hypertension and cardiac failure.

in which R1 is hydrogen, an alkyl, a cycloalkyl, a halogenated alkyl, —S—R7, —SO2—R7, —C≡C—R7 or —(CH2)p—OR7, R7 being hydrogen, an alkyl, a cycloalkyl or a halogenated alkyl, p being zero or 1, —A1=A2—A3=A4— is —CH=CH—CH=CH—, —N=CH—CH=CH—, —CH=N—CH=CH—, —CH=CH—N=CH—, —CH=CH—CH=N— or —CH=N—CH=N—, R2 and R3 are each hydrogen, a halogen, a lower alkyl, a lower alkoxy, a carbamoyl or cyano, R4 is hydrogen or a lower alkyl, R5 is 1H-tetrazol-5-yl, carboxyl (—COOH) or a carboxylic ester and R6 is hydrogen, a halogen, hydroxyl or a lower alkoxy, or a pharmacologically acceptable salt thereof.

4 Claims, No Drawings

BIPHENYLMETHANE DERIVATIVE AND PHARMACOLOGICAL USE

This application is a divisional of application Ser. No. 07/846,950, filed on Mar. 6, 1992, now U.S. Pat. No. 5,298,518, which is a Rule 60 Divisional application of Ser. No. 07/675,155, filed on Mar. 26, 1991, now abandoned, which is a continuation-in-part application of Ser. No. 07/583,025, filed on Sep. 13, 1990, now U.S. Pat. No. 5,328,911, the entire contents of which are hereby incorporated by reference.

FIELD OF THE INDUSTRIAL APPLICATION

The present invention relates to a condensed imidazole compound and pharmacologically acceptable salts thereof which exhibit an excellent activity as a pharmaceutical. More particularly, the present invention is concerned with a novel biphenylmethane derivative and pharmacologically acceptable salts thereof useful as a therapeutic agent for hypertension and/or a therapeutic agent for cardiac failure.

BACKGROUND OF THE INVENTION AND PRIOR ART

About 20% of the whole Japanese, i.e., about twenty million or more Japanese are suffering from hypertension, and the hypertension is a serious risk factor of various cerebral diseases, heart diseases, etc. In practice, thiazide hypotensive diuretic agents, β-blockers, calcium antagonists, ACE inhibitors, etc., have now been clinically utilized for drug therapy of the hypertension.

However, the origin and pathology of the hypertension are very different, and it is difficult to significantly control all types of hypertension through the use of only one drug. Further, regarding safety, the β-blocker brings about cardiac depression and bronchial actuation as the side effects and the diuretic agent brings about side effects such as hyperuricemia, abnormal saccharometabolism and abnormal fat metabolism, while the ACE inhibitor brings about cough as the side effect.

Under the above-described circumstances, different types of better hypotensives which exhibit their effects through various mechanisms have still been desired.

The present inventors have made extensive and intensive studies on a compound having a nonpeptide angiotensin II antagonistic activity for years and, as a result, have found that the following biphenylmethane derivative has an excellent activity.

Examples of the imidazole compound having an angiotensin II antagonistic activity proposed in the art include those disclosed in Japanese Patent Laid-Open Nos. 148788/1979, 71073/1981, 71074/1981, 98270/1982, 157768/1983 and 23868/1988. Further, Japanese Patent Laid-Open No. 240683/1987 proposes 4,5,6,7-tetrahydro-1H-imidazo[4,5-c]pyridine-6-carboxylic acid derivatives. Any of the above-described compounds are different from the compounds of the present invention, which will be described hereinbelow, in the structure.

SUMMARY OF THE INVENTION

The invention provides a biphenylmethane derivative having the formula (I):

in which $R^1$ is hydrogen, an alkyl, a cycloalkyl, a halogenated alkyl, —S—$R^7$, —$SO_2$—$R^7$, —C=C—$R^7$ or —$(CH_2)_p$—$OR^7$, $R^7$ being hydrogen, an alkyl, a cycloalkyl or a halogenated alkyl, p being zero or 1, —$A^1$=$A^2$—$A^3$=$A^4$— is —CH=CH—CH=CH—, —N=CH—CH=CH—, —CH=N—CH=CH—, —CH=CH—N=CH—, —CH=CH—CH=N— or —CH=N—CH=N—, $R^2$ and $R^3$ are each hydrogen, a halogen, a lower alkyl, a lower alkoxy, a carbamoyl or cyano, $R^4$ is hydrogen or a lower alkyl, $R^5$ is 1H-tetrazol-5-yl, carboxyl (—COOH) or a carboxylic ester and $R^6$ is hydrogen, a halogen, hydroxyl, or a lower alkoxy, or a pharmacologically acceptable salt thereof.

It is preferable that $R^5$ is carboxyl or 1H-tetrazol-5-yl. $R^5$ may be a carboxylic ester with an alkyl having 1 to 6 carbon atoms.

It is preferable that $R^1$ is an alkyl selected from methyl, ethyl, propyl, methoxy, ethoxy and cyclopropyl; and —$A^1$=$A^2$—$A^3$=$A^4$— is —CH=CH—CH=N—.

It is preferable that $R^2$ is hydrogen on $A^1$ and $R^3$ is methyl on $A^3$; $R^2$ is methyl on $A^1$ and $R^3$ is methyl on $A^3$; or $R^2$ is methyl on $A^1$ and $R^3$ is hydrogen on $A^3$.

It is preferable that $R^4$ is hydrogen and $R^6$ is hydrogen.

The following two compounds are most preferable:
7-methyl-2-n-propyl-3-[(2'-(1H-tetrazol-5-yl)-biphenyl-4-yl)methyl]-3H-imidazo[4,5-b]pyridine
3-[(2'-carboxylbiphenyl-4-yl) methyl]-2-cyclopropyl-7-methyl- 3H-imidazo[4,5-b]pyridine The following compounds are preferable:
2-Ethyl-7-methyl-3-[{2'-(1H-tetrazol-5-yl)biphenyl-4-yl}methyl]-3H-imidazo[4,5-b]pyridine
3-{(2'-Carboxybiphenyl-4-yl)methyl}-7-methyl- 2-n-propyl-3H-imidazo[4,5-b]pyridine
2-Cyclopropyl-7-methyl-3-[{2'-(1H-tetrazol-5-yl) biphenyl-4-yl}methyl]-3H-imidazo[4,5-b]pyridine
3-[{5'-Chloro-2'-(1H-tetrazol-5-yl)biphenyl-4-yl} methyl]-7-methyl-2-n-propyl-3H-imidazo[4,5-b]pyridine
3-{(2'-Carboxybiphenyl-4-yl)methyl}-2-ethylthio- 7-methyl-3H-imidazo[4,5-b]pyridine
3-{(2'-Carboxy-5'-chlorobiphenyl-4-yl)methyl}- 2-cyclopropyl-7-methyl-3H-imidazo[4,5-b]pyridine
2-n-Propyl-3-[{2'-(1H-tetrazol-5-yl)biphenyl- 4-yl}methyl] -3H-imidazo[4,5-b]pyridine
2-Methoxy-7-methyl-3-[{2'-(1H-tetrazol-5-yl) biphenyl-4-yl}methyl]-3H-imidazo[4,5-b]pyridine
2-Cyclopropyl-5,7-dimethyl-3-[{2'-(1H-tetrazol-5-yl) biphenyl-4-yl}methyl]-3H-imidazo[4,5-b]pyridine
3-{(2'-Carboxybiphenyl-4-yl)methyl}-2-cyclopropyl- 5,7-dimethyl-3H-imidazo[4,5-b]pyridine
5,7-Dimethyl-2-n-propyl-3-[{2'-(1H-tetrazol-5-yl) biphenyl-4-yl}methyl]-3H-imidazo[4,5-b]pyridine
3-{2'-Carboxybiphenyl-4-yl)methyl}-2-n-propyl- 5,7-dimethyl-3H-imidazo[4,5-b]pyridine
2-Ethoxy-7-methyl-3-[{2'-(1H-tetrazol-5-yl) biphenyl-4-yl}methyl]-3H-imidazo[4,5-b]pyridine 7-Methyl-2n-propoxy-3-[{2'-(1H-tetrazol-5-yl) biphenyl-4-yl}methyl]-3H-imidazo[4,5-b]pyridine 7-Methyl-2-(1-propynyl)-3-[{2'-(1H-tetrazol-5-yl) biphenyl-4-yl}methyl]-3H-imidazo[4,5-b]pyridine 2-Ethylthio-7-methyl-3-[{2'-(1H-tetrazol-5-yl) biphenyl-4-yl}methyl]-3H-imidazo[4,5-b]pyridine 3-{(2'-Carboxybiphenyl-4-yl)methyl}-2-ethyl- 7-methyl-3H-imidazo[4,5-b]pyridine 2-Ethoxy-5,7-dimethyl-3-[{2'-(1H-tetrazol-5-yl)biphenyl-4-yl}methyl]- 3H-imidazo[4,5-b]pyridine 5,7-Dimethyl-2-methoxy-3-[{2'-(1H-tetrazol-5-yl)biphenyl-4-yl}methyl]- 3-imidazo[4,5-b]pyridine 5,7-Dimethyl-2-propoxy-3-[{2'-(1H-tetrazol-5-yl)biphenyl-4-yl} methyl]-3-imidazo[4,5-b]pyridine 3-{(2'-Carboxybiphenyl-4-yl)methyl}-2-ethoxy-7-methyl-3H-imidazo[4,5-b]pyridine 3-{(2'-Carboxybiphenyl-4-yl)methyl}-2-methoxy-7-methyl- 3H-imidazo[4,5-b]pyridine 3-{(2'-Carboxybiphenyl-4-yl)methyl}-2-methyl-2-n-propoxy- 3H-imidazo[4,5-b]pyridine 3-{(2'-Carboxybiphenyl-4-yl)methyl}-5,7-dimethyl-2-ethoxy- 3H-imidazo[4,5-b]pyridine 3-{(2'-Carboxybiphenyl-4-yl)methyl}-5,7-dimethyl-2-methoxy- 3H-imidazo[4,5-b]pyridine 3-{(2'-Carboxybiphenyl-4-yl)methyl}-5,7-dimethyl-2-propoxy- 3H-imidazo[4,5-b]pyridine The invention further provides a pharmacological composition comprising a pharmacologically effective amount of the biphenylmethane derivative or a pharmacologically acceptable salt thereof as defined above and a pharmacologically acceptable carrier.

The invention provides a method for preventing and treating hypertension or cardiac failure by administering a pharmacologically effective amount of the biphenylmethane derivative or a pharmacologically acceptable salt thereof as defined above to a patient.

The compounds of the present invention include a biphenylmethane derivative represented by the following general formula (I) and pharmacologically acceptable salts thereof:

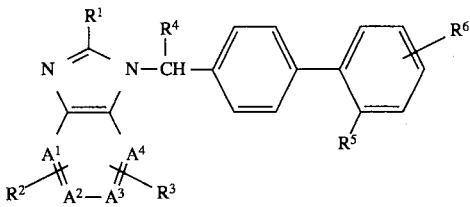

wherein $R^1$ is a hydrogen atom, an alkyl group, a cycloalkyl group, a halogenated alkyl group or a group represented by the formula $—S—R^7$ (wherein $R^7$ is a hydrogen atom, an alkyl group, a cycloalkyl group or a halogenated alkyl group), $—A^1=A^2A^3=A^4—$ is a group represented by the formula $—CH=CH—CH=CH—$, a group represented by the formula $—N=CH—CH=CH—$, a group represented by the formula $—CH=N—CH=CH—$, a group represented by the formula $—CH=CH—N=CH—$ or a group represented by the formula $—CH=CH—CH=N—$, $R^2$ and $R^3$ which may be the same or different are each a hydrogen atom, a halogen atom, a lower alkyl group, a lower alkoxy group, a carbamoyl group or a cyano group;

$R^4$ is a hydrogen atom or a lower alkyl group;

$R^5$ is a group represented by the formula

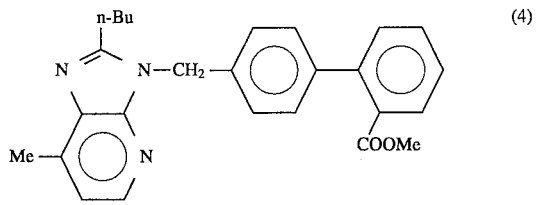

or a carboxyl group; and $R^6$ is a hydrogen atom, a halogen atom, a hydroxyl group or a lower alkoxy group.

The term "lower alkyl group" in the above-described definition of $R^2$, $R^3$ and $R^4$ on the compounds of the present invention is intended to mean a straight-chain or branched alkyl group having 1 to 6 carbon atoms, and examples thereof include methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups, among which methyl, ethyl, propyl, isopropyl groups, etc., are preferred and methyl and ethyl groups are most desirable. Especially a methyl group is most desirable as the lower alkyl group in the definition of $R^4$.

The term "lower alkoxy group" used in the definition of $R^2$, $R^3$ and $R^4$ is intended to mean a lower alkoxy group derived from the above-described lower alkyl group, such as methoxy, ethoxy and n-propoxy, among which a methoxy group is most desirable.

The term "halogen atom" in the definition of $R^2$, $R^3$ and $R^6$ is intended to mean a chlorine atom, a bromine atom, a fluorine atom or the like.

The term "alkyl group" in the definition of $R^1$ is preferably intended to mean a straight-chain or branched alkyl group having 1 to 10 carbon atoms. The alkyl group include, besides the above-described alkyl groups having 1 to 6 carbon atoms, n-heptyl, n=octyl, n-nonyl and n-decyl groups and branched alkyl groups. Among them, straight-chain or branched alkyl groups having 1 to 8 carbon atoms are preferred, and especially preferred examples thereof include methyl, ethyl, n-propyl, isopropyl, n-butyl and n-pentyl groups.

The above shown preferable embodiments for R1 can apply also to R7.

The term "halogenated alkyl group" is intended to mean a group wherein any one or more hydrogen atoms of the alkyl group as defined above is substituted by a halogen atom, especially a fluorine atom.

The term "cycloalkyl group" is intended to mean, e.g., a cycloalkyl group having 3 to 6 carbon atoms, and cyclopropyl and cyclobutyl groups are most desirable.

The group represented by the formula $—A^1=A^2—A^3=A^4—$ is intended to mean:

① a group represented by the formula $—CH=CH—CH=CH—$;

② a group represented by the formula $—N=CH—CH=CH—$;

③ a group represented by the formula $—CH=N—CH=CH—$;

④ a group represented by the formula $—CH=CH—N=CH—$; or

⑤ a group represented by the formula $—CH=CH—CH=N—$.

Specific examples of the portion condensed with an imidazole ring in the compound of the present invention include the following groups:

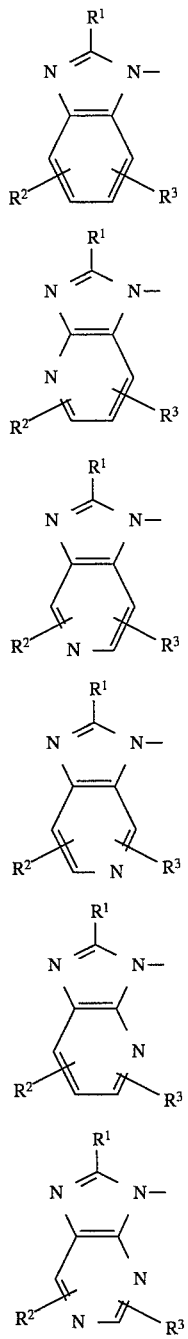

In the present invention, the group represented by the formula $-A^1=A^2-A^3=A^4-$ is most desirably a group represented by the formula (5) $-CH=CH-CH=N-$ and a group represented by the formula (2) $-N=CH-CH=CH-$ comes next.

The above-described benzimidazole or imidazopyridine ring may be substituted by the above-described $R^2$ and $R^3$. Preferred examples of the substituent include a lower alkyl group, and the most desirable benzimidazole or imidazopyridine ring is one mono-substituted by a methyl group.

The term "pharmacologically acceptable salt" may be any salt as far as it can be used in the present invention, and examples thereof include ammonium salt, sodium salt, potassium salt, hydrochloride, hydrobromide, methanesulfonate and sulfate.

Further, some of the above compounds may be present as the hydrate or as the optically active isomers. It is a matter of course that these compounds are within the scope of the present invention.

Representative processes for preparing the compound of the present invention will now be described.

PREPARATION PROCESS 1

A compound represented by the general formula (1) wherein $R^5$ is a tetrazolyl group represented by the formula

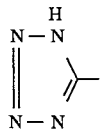

can be prepared by the following process:

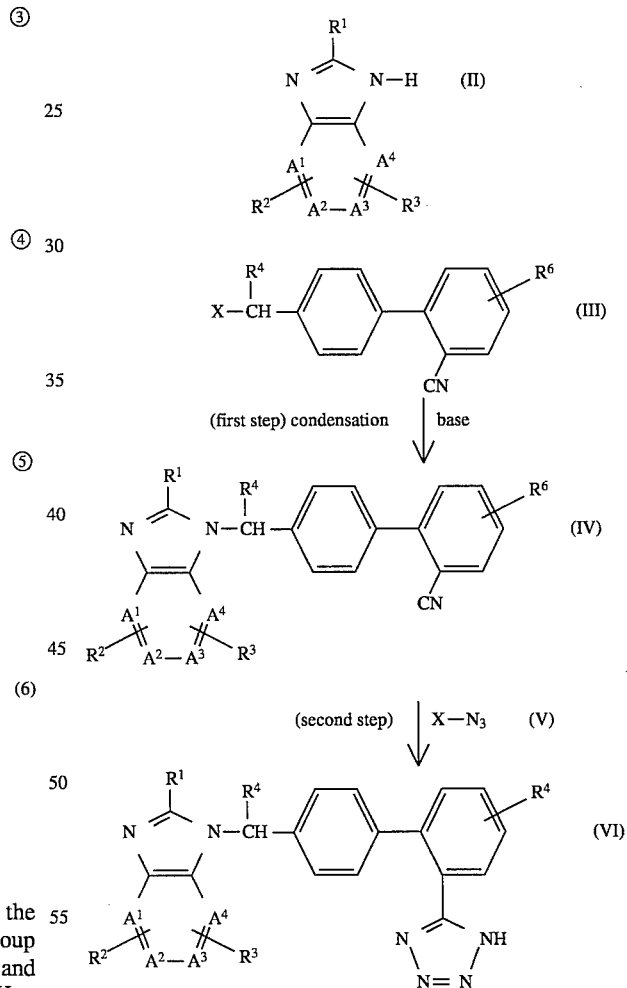

In the above-described formulae, $R^1$, $R^2$, $R^3$, $R^4$, $R^6$ and a group represented by the formula $-A^1=A^2-A^3=A^4-$ are each as defined above and X is a halogen atom, a methanesulfonyloxy group or a p-toluenesulfonyloxy group.

First Step

A condensed imidazole derivative represented by the general formula (II) is condensed with a nitrile compound represented by the general formula (III) by the conventional process to prepare a compound represented by the general formula (IV).

The above-described reaction is usually conducted in the presence of a base. Examples of the base include sodium hydride, lithium hydride, potassium carbonate, sodium carbonate, sodium alcoholate, tert-butoxypotassium, sodium hydroxide, potassium hydroxide, triethylamine and diisopropylethylamine.

Dimethylformamide, dimethyl sulfoxide, N-methylpyrrolidone, 1,3-dimethyl-2-imidazolidinone, dioxane, alcohol, acetone, etc., are preferred as the solvent for the reaction.

In the formulae, X is a halogen atom, a methanesulfonyloxy group or a p-toluenesulfonyloxy group, and the halogen atom may be chlorine, bromine, iodine or the like.

In the present process, especially preferred examples thereof include one which comprises forming a metal salt of (l) in an aprotic polar solvent, such as dimethylformamide, through the use of lithium hydride or sodium hydride as a base and then conducting alkylation at 0° C. to room temperature through the use of a biphenylmethyl halide [X=Cl, Br] and one which comprises forming a sodium salt of (l) in an alcohol through the use of sodium alcoholate as a base and then conducting alkylation at room temperature through the use of a biphenylmethyl halide IX=Cl, Br].

The compound represented by the general formula (III) which may be used as a starting material in the present process can be prepared by the process described in, e.g., A. I. Meyers et al., J. Org. Chem., 43, 1372 (1978) or Japanese Patent Laid-Open No. 23868/1988.

Second Step

The compound represented by the general formula (IV) can be reacted with an azide represented by the general formula (V) by heating in an aprotic polar solvent to prepare a compound represented by the general formula (VI).

The compound represented by the general formula (VI) can be preferably synthesized by heating sodium azide in the presence of an amine salt, such as ammonium chloride [see J. P. Hurwitz et al., J. Org. Chem., 26, 3392 (1961)], triethylamine hydrochloride [see P. P. Bernstein et al., Synthesis, 1133 (1987)] or a pyridine hydrochloride [see H. Nakai et al., J. Med. Chem., 31, 84 (1988)] while stirring in a solvent, such as dimethylformamide, N-methylpyrrolidone or 1,3-dimethyl-2-imidazolidone at 120° to 150° C.

When R1 is —(CH2)p—OR7, p is zero and R7 is an alkyl, the starting compound (II) in which R1 is an alkoxy can be used in the above shown process. Another process comprises conducting the steps (I) and (II) by using the starting compound (II) in which R1 is —S-alkyl, then oxidizing the obtained compound (VI') in which R1 is —SO2-alkyl and reacting the sulfonyl compound (VI') with a compound having —R7OM, R7 being an alkyl, M being a metal such as sodium and potassium, to obtain a final compound in which R1 is an alkoxy.

PREPARATION PROCESS 2

A compound represented by the general formula (I) wherein $R^5$ is a carboxyl group can be prepared, e.g., by the following process:

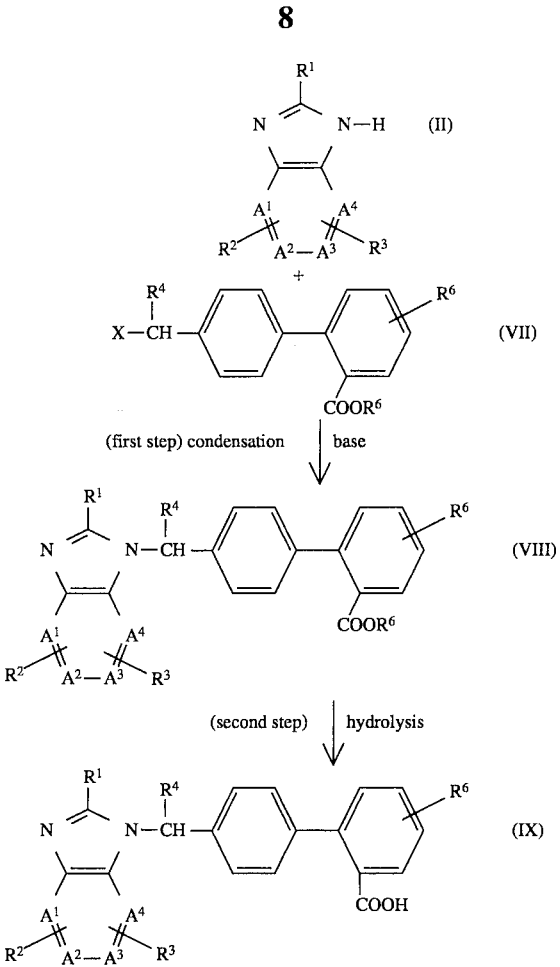

In the above-described formulae, $R^1$, $R^2$, $R^3$, $R^6$ and a group represented by the formula $—A^1=A^2—A^3=A^4—$ are each as defined above, First Step In this step, a condensed imidazole derivative represented by the general formula (II) is condensed with an ester represented by the general formula (VII) by the conventional method to prepare a compound represented by the general formula (VIII).

$R^8$ may be any group as far as it can combine with a carboxylic acid to form an ester, and representative examples thereof include methyl and ethyl groups.

The present reaction is usually conducted in the presence of a base. Preferred examples of the base include sodium hydride, lithium hydride, potassium carbonate, sodium carbonate, sodium alcoholate, tert-butoxypotassium, sodium hydroxide, potassium hydroxide, triethylamine and diisopropylethylamine.

Preferred examples of the solvent for the reaction include dimethylformamide, dimethyl sulfoxide, N-methylpyrrolidone, 1,3-dimethyl-2-imidazolidinone, dioxane, alcohol and acetone.

In the formulae, X is a halogen atom, a methanesulfonyloxy group or a p-toluenesulfonyloxy group, and the halogen atom is chloride, bromine or iodine.

In the present process, especially preferred examples thereof include one which comprises forming a metal salt of (l) in an aprotic polar solvent, such as dimethylformamide, through the use of lithium hydride or sodium hydride as a base and then conducting alkylation at 0° C. to room temperature through the use of a biphenylmethyl halide [X=Cl, Br] and one which comprises forming a sodium salt of (l) in an alcohol through the use of sodium alcoholate as a base and then conducting alkylation at room temperature through the use of a biphenylmethyl halide [X=Cl, Br].

Second Step

In this step, the ester represented by the general formula (VIII) is hydrolyzed to prepare one of the intended substances of the present invention, i.e., a compound represented by the general formula (IX).

The ester is hydrolyzed by the conventional procedure. When $R^8$ is a lower alkyl group such as a methyl or ethyl group, the ester can be easily converted into a carboxylic acid, e.g., by heating the ester under reflux in a mixed solvent comprising ethanol and an aqueous sodium hydroxide solution. Although the hydrolysis by a base is preferred, any method may be applied as far as it can eliminate the protective group of the carboxylic acid.

As shown above, the compound of the invention can be produced by the process (I) in which R5 being tetrazolyl, a condensed imidazol (II) and a biphenylmethane compound (II) are reacted with each other by condensation and cyano for R5 is converted to tetrazol with an azid compound (V).

When R5 is carboxyl or carboxyl ester, according to the process (II), a condensed imidazol (II) and a biphenylmethane compound (VII) are condensed to produce a compound (VIII) having a carboxylic ester of —COOR8 for R5. The compound in which R5 is —COOH can be obtained by hydrolyzing the compound (VIII).

The effect of the compounds of the present invention will now be described in more detail by way of the following examples of pharmacological experiment.

Examples of Pharmacological Experiment

1. Experimental Method (1) Angiotens in II contracture antagonism through the use of rabbit aortic strip A male New Zealand white rabbit having a weight of 2 to 3 kg was anesthetized with pentobarbital sodium, and the thoracic aorta was removed. A spiral preparation of the aorta having a width of 1.5 to 2 mm and a length of 15 to 20 mm was prepared therefrom and suspended in a 10-ml Magnus tank containing a Krebs bicarbonate solution (Krebs bicarbonate (mM): NaCl 118.4, KCl 4.7, $CaCl_2$ 2.0, $MgSO_4.7H_2O$ 1.2, $NaHCO_3.25.0$, $KH_2PO_4$ 1.2, glucose 11.1). $10^{-5}$ M indomethacine was added thereto to eliminate the influence of prostaglandin. The Krebs solution was maintained at 37° C. and bubbled with 95% $O_2$–5% $CO_2$. An initial tension of 1 g was applied to the strip, and the strip was allowed to stand for about 1 hr. Then, 50 mM KCl was added thereto to induce contracture. After the contracture was stabilized, the strip was washed. The above procedure was repeated twice, and the second contracture was taken as 100% contracture.

Thereafter, angiotensin II was accumulatively added from $10^{-10}$ to $3\times10^{-6}$ to prepare a dose-reaction curve. When studying the antagonistic activity of the angiotensin II antagonist, a test compound was added in a concentration of $10^{-6}$ to $10^{-9}$ M 40 min before the addition of $10^{-10}$ M angiotensin to observe the shift of the dose-reaction curve toward the right. The contraction was recorded on a multipen recorder (R-10 manufactured by Rika Denki Kogyo Co., Ltd.) through a carrier amplifier (AP620G or AP621G manufactured by Nihon Koden Corp.) by making use of an isometric piezoelectric transducer (TB611T manufactured by Nihon Koden Corp.). The potency of the angiotensin II antagonist was determined by calculating negative logarithm (-log) of a concentration of $pA_2$ value [i.e., a concentration of competitive antagonist which makes the dose ratio of the active agent 2] through the use of Schild's equation. The results are given in Table 1.

(2) Inhibition of pressor reaction of angiotensin II on anesthetized rat (Wistar Kyoto) having blocked ganglions A 9 to 25 week-old Wistar Kyoto male rat (Charles River Japan) was anesthetized with 50 mg/kg pentobarbital sodium intraperitoneally, and the carotid and jugular were cannulated. The carotid cannula was connected to a piezoelectric transducer (TP-200T), and recording was conducted with a polygraph system (RM-6000 manufactured by Nihon Koden Corp.) through a carrier amplifier (AP-601G manufactured by Nihon Koden Corp.) and an average blood pressure measuring panel (Nihon Koden Corp.) utilizing the integration of pulse waves. 10 mg/kg of pentolinium was administered intravenously through the jugular cannula to conduct ganglion blockade. After the blood pressure was stabilized, 0.003 to 0.1 or 0.3 µg/kg of angiotensin II was accumulatively administered intravenously at such time intervals that the pressor reaction in each dose was substantially restored (2 to 3 min), thereby preparing a dose-reaction curve. Then, 0.1 to 10 mg/kg of the test compound was administered intravenously, and 0.03 to 1 µg/kg of angiotensin II was again administered intravenously 3 min after the administration of the test compound to determine the rate of shift of the dose-pressor reaction curve toward the right. A dose (C, $ED_{50}$, mg/kg, i.v.) necessary for bringing about doubled shift of the dose-pressor reaction curve toward the right was determined from the dose of the antagonist (A, mg/kg, i.v.) and the above-described rate of shift (B).

$$C = \frac{A}{B/2} \text{ (mg/kg, i.v.)}$$

The results are given in Table 1.

2. EXPERIMENTAL RESULTS

The results of pharmacological experiments (1) and (2) on the compounds of the present, invention (test compounds) are given in Table 1.

TABLE 1

| Comp. No. | Chemical structure of test comp. | $pA_2$ | Dose necessary for shifting about doubled shift of pressor reaction of angiotensin toward right (mg/kg, i.v.) |
|---|---|---|---|
| 1 | (structure) | 8.11 | 0.74 |
| 2 | (structure) | 9.08 | 0.15 |
| 3 | (structure) | 8.81 | 0.44 |
| 4 | (structure) | 8.00 | 1.57 |
| 5 | (structure) | 10.33 | 0.029 |
| 6 | (structure) | 10.04 | 0.019 |

TABLE 1-continued

| Comp. No. | Chemical structure of test comp. | pA$_2$ | Dose necessary for shifting about doubled shift of pressor reaction of angiotensin toward right (mg/kg, i.v.) |
|---|---|---|---|
| 7 | (structure) | 10.64 | 0.022 |
| 8 | (structure) | 8.37 | 0.71 |
| 9 | (structure) | 7.63 | 1.33 |
| 10 | (structure) | 9.18 | 0.42 |
| 11 | (structure) | 9.74 | 0.04 |
| 12 | (structure) | 9.28 | 0.13 |

TABLE 1-continued

| Comp. No. | Chemical structure of test comp. | $pA_2$ | Dose necessary for shifting about doubled shift of pressor reaction of angiotensin toward right (mg/kg, i.v.) |
|---|---|---|---|
| 13 | (structure: n-Pr substituted imidazopyridine with Cl, N—CH₂—biphenyl—COOH) | 8.06 | 0.66 |
| 14 | (structure: Et substituted imidazopyridine with Cl, N—CH₂—biphenyl—tetrazole) | 8.53 | 0.35 |
| 15 | (structure: n-Pr substituted imidazopyridine with Me, Cl, N—CH₂—biphenyl—tetrazole) | 8.87 | 0.32 |
| 16 | (structure: Et substituted imidazopyridine with Me, N—CH₂—biphenyl—COOH) | 8.50 | 0.29 |
| 17 | (structure: n-Pr substituted imidazopyridine with Me, N—CH₂—biphenyl—COOH) | 8.45 | 0.17 |
| 18 | (structure: cyclopropyl substituted imidazopyridine with Me, N—CH₂—biphenyl—COOH) | 8.67 | 0.075 |

TABLE 1-continued

| Comp. No. | Chemical structure of test comp. | pA$_2$ | Dose necessary for shifting about doubled shift of pressor reaction of angiotensin toward right (mg/kg, i.v.) |
|---|---|---|---|
| 19 | (cyclobutyl-C(=N-)-N(CH$_2$-biphenyl-2-COOH)- fused to 4-Me-pyridine) | 8.31 | 0.25 |
| 20 | (EtS-C(=N-)-N(CH$_2$-biphenyl-2-COOH)- fused to 4-Me-pyridine) | 8.28 | 0.41 |
| 21 | (n-Pr-C(=N-)-N(CH$_2$-(4'-Cl-biphenyl-2-tetrazol-5-yl))- fused to 4-Me-pyridine) | 10.94 | 0.071 |
| 22 | (n-Pr-C(=N-)-N(CH$_2$-biphenyl-2-tetrazol-5-yl)- fused to 4,6-diMe-pyridine) | 10.62 | 0.040 |
| 23 | (n-Pr-C(=N-)-N(CH$_2$-biphenyl-2-COOH)- fused to 4,6-diMe-pyridine) | 8.94 | 0.080 |
| 24 | (cyclopropyl-C(=N-)-N(CH$_2$-biphenyl-2-tetrazol-5-yl)- fused to 4,6-diMe-pyridine) | 10.86 | 0.015 |

TABLE 1-continued
| Comp. No. | Chemical structure of test comp. | pA$_2$ | Dose necessary for shifting about doubled shift of pressor reaction of angiotensin toward right (mg/kg, i.v.) |
|---|---|---|---|
| 25 | 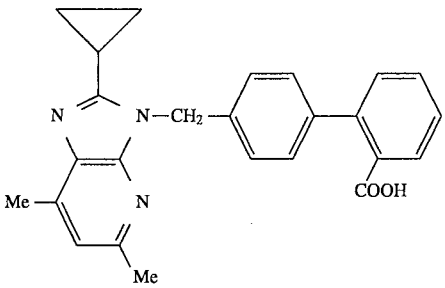 | 9.23 | 0.021 |
| 26 | 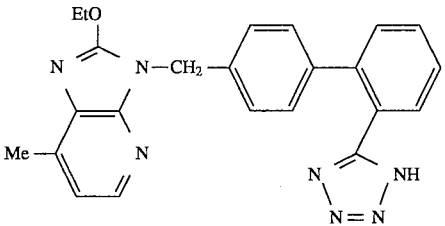 | 10.58 | 0.0084 |
| 27 | 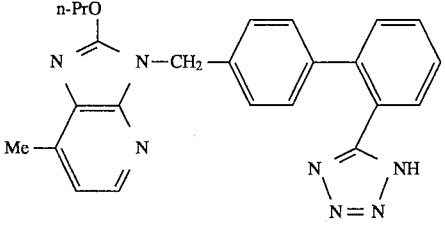 | 9.43 | 0.034 |
| 28 | 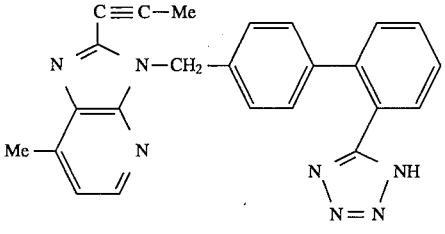 | 9.05 | 0.040 |
| 29 | 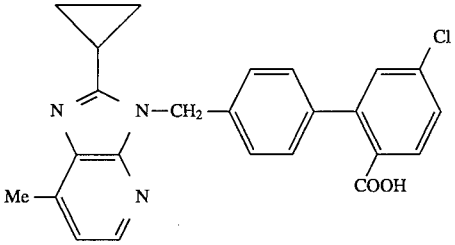 | 8.47 | 0.060 |
| 30 | 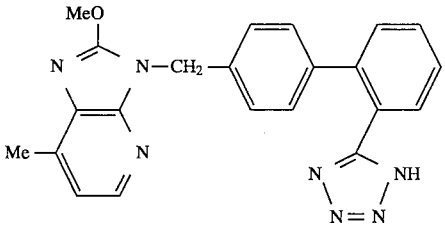 | 9.88 | 0.016 |

TABLE 1-continued

| Comp. No. | Chemical structure of test comp. | pA$_2$ | Dose necessary for shifting about doubled shift of pressor reaction of angiotensin toward right (mg/kg, i.v.) |
|---|---|---|---|
| 31 | (structure: pyridine with EtO, N, Me, Me substituents; N—CH$_2$—biphenyl—tetrazole) | 9.74 | 0.010 |
| 32 | (structure: pyridine with EtO, N, Me, Me substituents; N—CH$_2$—biphenyl—COOH) | 9.24 | 0.018 |

From the above-described examples of pharmacological experiment, it is apparent that the compounds of the present invention have a remarkably excellent angiotensin II antagonism.

Further, compound Nos. 1, 2, 5 and 6 listed in the above-described Table 1 were suspended in 0.5% MC (methylcellulose), and the suspension was orally administered to an eight week-old male SD (Sprague Dawley) rats (4 rats per group) in a dose of 100 mg/kg/day for seven days. The rats were observed until 24 hr after the final administration. As a result, no death was observed in all the groups to which the above-described compounds (compound Nos. 1, 2, 5 and 6) were administered.

Therefore, by virtue of the angiotensin II antagonism, the compounds of the present invention are useful for the therapy and prevention of hypertension, useful for the therapy and prevention of cardiac failure and useful for the therapy and prevention of other diseases for which the angiotensin antagonism is useful. Specifically, they are useful as a therapeutic and preventive agent for hypertension such as essential, renal, renovascular or malignant hypertension, and further as a therapeutic and preventive agent for cardiac failure. Further, as described above, the compounds of the present invention have a high safety, which renders the present invention highly valuable.

When using the compounds of the present invention as a pharmaceutical, they may be orally or parenterally administered. The dose of the compounds of the present invention will vary depending upon the symptom; age, sex, weight and difference in the sensitivity of patients; method of administration; time and intervals of administration, and properties, formulation and kind of pharmaceutical preparations; and kind of active ingredients, etc., so that there is no particular limitation on the dose.

In the case of oral administration, the compounds of the present invention are usually administered in a dose of about 1 to 1,000 mg, preferably about 5 to 500 mg per adult per day in one to three portions. In the case of injection, the dose is usually about 1 to 3,000 μg/kg preferably about 3 to 1,000 μg/kg.

When preparing a solid preparation for oral administration, the active ingredient is blended with a vehicle and, if necessary, a binder, a disintegrator, a lubricant, a colorant, a corrigent, etc., followed by the preparation of tablets, coated tablets, granules, powders and capsules by the conventional procedure.

Examples of the vehicle include lactose, corn starch, sucrose, glucose, sorbitol, crystalline cellulose and silicon dioxide. Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricant include magnesium stearate, talc, polyethylene glycol, silica and hydrogenated vegetable oil. Any colorant of which the addition to pharmaceuticals is officially allowed can be used as the colorant. Examples of the corrigent include cacao powder, menthol, aromatic powder, mentha powder, borneol and powdered cinnamon bark. It is a matter of course that a sugar coating, a gelatin coating and, if necessary, suitable other coatings may be applied on these tablets and granules.

When preparing injections, a pH modifier, a buffering agent, a suspending agent, a solubilizing agent, a stabilizer, a tonicity agent, a preservative, etc., are added to the active ingredient, followed by the preparation of intravenous, subcutaneous and intramuscular injections according to the conventional procedure. In this case, these preparations may be lyophilized by the conventional procedure.

Examples of the suspending agent include methylcellulose, Polysorbate 80, hydroxyethylcellulose, gum arabic, powdered trangcanth, sodium carboxymethylcellulose and polyoxyethylene sorbitan monolaurate.

Examples of the solubilizing agent include polyoxyethylene hydrogenated castor oil, Polysorbate 80, nicotinamide, polyoxyethylene sorbitan monolaurate, Macrogol,-and ethyl esters of castor oil fatty acids.

Examples of the stabilizer include sodium sulfite, sodium metasulfite and ether, and examples of the preservative include methyl p-hydroxybenzoate, ethyl p-hydroxybenzoate, sorbic acid, phenol, cresol and chlorocresol.

Representative compounds of the present invention will now be described by way of the following Examples. It is needless to say that the present invention is not limited to these only.

Apart from the Examples, Preparation Examples will be given for the preparation of a starting material used in the preparation of the object substance of the present invention.

In the chemical structural formulae, Me is a methyl group, Et an ethyl group, n-Pr a n-propyl and n-Bu a n-butyl group.

PREPARATION EXAMPLE 1

4-Chloro-2-methoxybenzoyl chloride

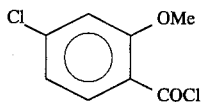

120 ml of thionyl chloride was dropwise added at room temperature to 75 g of 4-chloro-2-anisic acid, and the mixture was stirred at room temperature for 12 hr. The reaction mixture was concentrated for crystallization. The crystal was used for the subsequent reaction without purification.

PREPARATION EXAMPLE 2

2-(4-Chloro-2-methoxyphenyl)-4,4-dimethyloxazoline

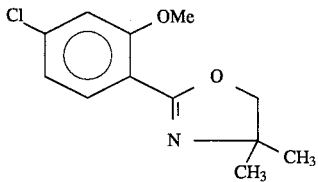

80 g of 2-amino-2-methyl-1-propanol was dissolved in 350 ml of methylene chloride, and the solution was cooled to −5° C. 4-Chloro-2-methoxybenzoyl chloride was dissolved in 180 ml of methylene chloride and then slowly dropwise added to the cooled solution. After the dropwise addition, the mixture was stirred at room temperature for 2 hr. The reaction mixture was filtered, and the crystal was washed with methylene chloride. Dilute hydrochloric acid was added to the filtrate and then subjected to phase separation to get an organic phase. The organic phase was dried over anhydrous magnesium sulfate and then concentrated. 120 ml of thionyl chloride was slowly dropwise added at room temperature to 106 g of the resultant oleaginous substance. The mixture was stirred for an additional 1 hr and then concentrated. Water was added to the concentrate for dissolution, and an aqueous sodium hydroxide solution was added to the solution to adjust the pH value to 11. Chloroform was added thereto, and the mixture was extracted, dried over anhydrous magnesium sulfate and then concentrated. The residue was purified by column chromatography (chloroform). The yield was 62.3 g.

NMR(90 MHz, CDCl₃, δ value): 7.65(d,1H,J=8 Hz), 7.00~6.81(m,2H), 4.05 (s,2H), 3.87(s,3H),1.39(s,6H)

PREPARATION EXAMPLE 3

2-(4-Chloro-4'-methylbiphenyl-2-yl)-4,4-dimethyloxaline

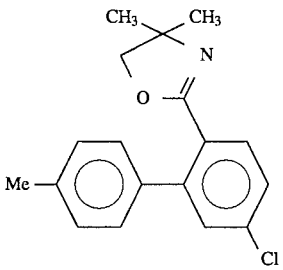

A THF solution (450 ml) of 46.0 g of 4-bromotoluene was dropwise added to 6.38 g of magnesium in a nitrogen stream. After heating under reflux for 40 min, the reaction mixture was dropwise added at room temperature to a THF solution (260 ml) of 30 g of 2-(4-chloro-2-methoxyphenyl)-4,4-dimethyloxazoline. The mixture was stirred at room temperature for 2 hr and then cooled, and an aqueous ammonium chloride was added thereto. The mixture was extracted with ethyl acetate, and the extract was washed with a dilute sodium hydroxide solution and a saline solution, dried over anhydrous magnesium sulfate and then concentrated to prepare 38 g of the title compound in a crude form.

NMR(90 MHz, CDCl₃, δ value): 7.64(d,1H,J=8 Hz), 7.40~7.00(m,6H),3.79 (s,2H),2.38(s,3H),1.29(s,6H)

PREPARATION EXAMPLE 4

4-Chloro-2-(4-methylphenyl)benzoic acid

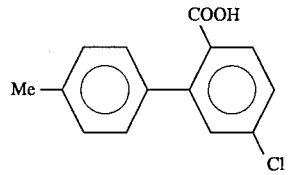

500 ml of 4.6N hydrochloric acid was added to 38 g of 2-(4-chloro-4'-methylbiphenyl-2-yl)-4,4-dimethyloxazoline, and the mixture was heated under reflux for 36 hr. After cooling the refluxed solution was extracted with a mixed solvent comprising ether and ethyl acetate, washed with water, dried over anhydrous magnesium sulfate and then concentrated. The residue was recrystallized from THF-isopropyl ether-hexane to give 17.5 g of the title compound.

m.p. (°C.): 143.5~146

NMR (90 MHz, CDCl₃, δ value): 9.30 (bs, 1H), 7.87 (1H, d, J=8 Hz), 7.46~7.20 (m, 2H), 7.18 (s, 4H), 2.38 (s, 3H)

The following starting materials used for synthesizing the compounds of the present invention were prepared according to the process described in Preparation Examples 1 to 4.

(1) 3-Methoxy-2-(4-methylphenyl)benzoic acid m.p. (°C.): 180.5~181

NMR(90 MHz, CDCl₃, δ value): 9.40(bs, 1H), 7.55~6.98 (m, 3H), 7.06 (s, 4H), 3.73 (s, 3H), 2.38 (s, 3H)

(2) 4-Methoxy-2-(4-methylphenyl)benzoic acid m.p. (°C.): 176~179

NMR(90 MHz, CDCl₃, δ value): 9.40 (bs, 1H), 7.96 (d, 1H, J=8 Hz), 7.18 (s, 4H), 6.97~6.56 (m, 2H), 3.84 (s, 3H), 2.39 (s, 3H)

(3) 5-Chloro-2-(4-methylphenyl)benzoic acid m.p. (°C.): 143~145

NMR (90 MHz, CDCl$_3$, δ value): 10.05 (bs, 1H), 7.88 (d, 1H, J=2 Hz), 7.49 (dd, 1H, J=2 Hz, 8 Hz), 7.26 (d, 1H, J=8 Hz), 7.16 (s, 4H), 2.37 (s, 4H)

(4) 5-Methoxy-2-(4-methylphenyl)benzoic acid

NMR (90 MHz, CDCl$_3$, δ value): 9.40 (bs, 1H), 7.37~6.82 (m, 7H), 3.81 (s, 3H), 2.32 (s,3H)

PREPARATION EXAMPLE 5

4-Chloro-2-(4-methylphenyl)benzamide

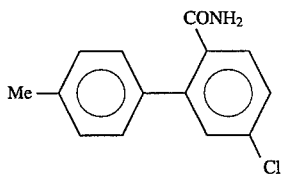

40 ml of thionyl chloride was dropwise added to 12.4 g of 4-chloro-2-(4-methylphenyl)benzoic acid, and the mixture was heated under reflux for 2 hr. The reaction mixture was concentrated. In this procedure, toluene was added to distill off the thionyl chloride as much as possible. The residue was dissolved in 120 ml of tetrahydrofuran, and an ammonia gas was blown into the solution at an internal temperature of −12° to −5° C. Water and chloroform were added to the reaction mixture, and the mixture was subjected to phase separation. The organic phase was washed with water and then dried over anhydrous magnesium sulfate. The dried organic phase was concentrated and then recrystallized from tetrahydrofuran-isopropyl ether to give 9.1 g of the title compound.

m.p. (°C.): 162~163.5

NMR(90 MHZ, CDCl$_3$, δ value): 7.72(d,1H,J=8 Hz), 7.42~7.08(m,2H),7.16 (s,4H),2.39(s,3H)

PREPARATION EXAMPLE 6

4-Chloro-2-(4-methylphenyl)benzonitrile

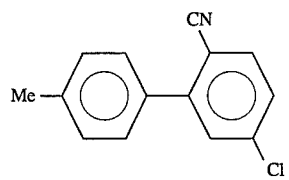

26 ml of thionyl chloride was dropwise added to 8.9 g of 4-chloro-2-(4-methylphenyl) benzamide, and the mixture was heated under reflux for 2.5 hr. Excess thionyl chloride was distilled off as much as possible by making use of toluene. The residue was recrystallized from a mixed solvent of tetrahydrofuran-isopropyl ether-n-hexane to prepare 7.2 g of a product.

m.p. (°C.): 48°~50° C.

NMR (90 MHz, CDCl$_3$, δ value): 7.66 (d, 1H, J=8 Hz), 7.60~7.15 (m, 6H), 2.38 (s,3H)

The following starting materials used for synthesizing the compounds of the present invention were prepared according to the process described in Preparation Examples 5 to 6.

(1) 3-Methoxy-2-(4-methylphenyl)benzonitrile m.p. (°C.): 94.5~96

NMR(90 MHz, CDCl$_3$, δ value): 7.45~7.10 (m, 7H), 3.78 (s, 3H), 2.41 (s, 3H)

(2) 4-Methoxy-2-(4-methylphenyl)benzonitrile m.p. (°C.): 121~123

NMR (90 MHz, CDCl$_3$, δ value): 7.66 (d, 1H, J=8 Hz), 7.50~7.15 (m, 4H), 7.00~6.78 (m,2H), 3.88 (s, 3H), 2.42 (s, 3H)

(3) 5-Chloro-2-(4-methylphenyl)benzonitrile m.p. (°C.): 111~113.5

NMR (90 MHz, CDCl$_3$, δ value): 7.75~7.15 (s, 7H), 2.42(s, 3H)

(4) 5-Methoxy-2-(4-methylphenyl)benzonitrile m.p. (°C.): 152~155

NMR (90 MHz, CDCl$_3$, δ value): 7.45~6.93 (m, 7H), 3.91 (s, 3H), 2.44 (s, 3H)

PREPARATION EXAMPLE 7

2-(4-Bromomethylphenyl)4-chlorobenzonitrile

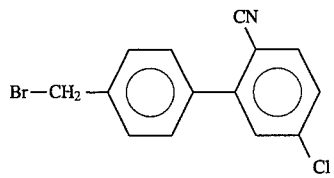

6.83 g of 4-chloro-2-(4-methylphenyl)benzonitrile, 5.34 g of N-bromosuccinimide and 0.1 g of α,α'-azobis(isobutyronitrile) were heated in 220 ml of carbon tetrachloride under reflux for 2 hr. The succinimide was removed by filtration, and the filtrate was concentrated. The residue was crystallized from a mixed solvent of tetrahydrofuran-isopropyl ether. The yield was 5.6 g.

m.p. (°C.): 122~125

NMR (90 MHz, CDCl$_3$, δ value): 7.69(d,2H,J=8 Hz),7.52 (s, 4H), 7.48(d, 1H, J=2 Hz), 7.40(dd, 1H, J=2 Hz, 8 Hz), 4.53 (s, 2H)

PREPARATION EXAMPLE 8

Methyl 2-(4-methylphenyl)benzoate

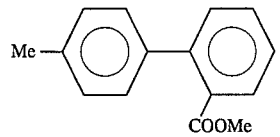

6 g of sulfuric acid in 12 ml of methanol was added to 3.2 g of 2-(4-methylphenyl)benzoic acid [see A. I. Meyers et al., J. Org. Chem., 43, 1372 (1978)], and the mixture was heated under reflux for 8 hr. The refluxed solution was cooled, poured into ice water, weakly alkalified with aqueous ammonia and extracted with ether. The extract was dried over anhydrous magnesium sulfate. The dried extract was concentrated, and the residue was recrystallized from n-hexane to prepare 2.4 g of the title compound.

m.p. (°C.): 54~57

PREPARATION EXAMPLE 9

Methyl 2-(4-bromomethylphenyl)benzoate

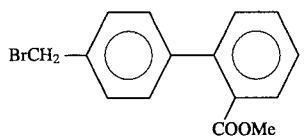

2.0 g of methyl 2-(4-methylphenyl)benzoate, 1.6 g of N-bromosuccinimide and 0.05 g of α,α'-azobis(isobutyronitrile) were heated in 110 ml of carbon tetrachloride under reflux for 2 hr. The succinimide was filtered off. The filtrate was concentrated, and the residue was recrystallized from a mixed solvent of n-hexane-isopropyl ether to prepare 1.6 g of the title compound.

m.p. (°C.): 50–51

PREPARATION EXAMPLE 10

(1) 2-Amino-4-n-propylpyridine

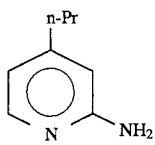

75 g (0.62M) of 4-n-propylpyridine and 28 g (0.73M) of sodium amide were added to 250 ml of xylene, and the mixture was heated under reflux for 10 hr. Water was added in small portions to the reaction mixture under ice cooling to decompose excess sodium amide, and the reaction mixture was extracted with ethyl acetate, dried over magnesium sulfate and then purified by column chromatography (dichloromethanemethanol 50:1÷20:1). The yield was 33 g. (blackish purple solid)

NMR (90 MHz, CDCl$_3$, δ value); 7.90 (d, 1H, J=8 Hz), 6.46 (dd, 1H, J=5 Hz, 1Hz), 6.28 (d, 1H, J=1 Hz), 4.50 (bs, 2H), 2.44 (t, 2H, J=7 Hz), 1.82~1.30(m, 2H), 0.94 (t, 3H, J=7 Hz)

(2) 2,3-Diamino-4-n-propylpyridine

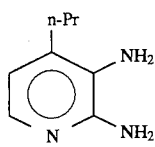

33 g (0.24M) of 2-amino-4-n-propylpyridine was added in small portions to 120 ml of concentrated sulfuric acid at an internal temperature of 25° C. or below under ice cooling. 17 ml (0.38M) of concentrated nitric acid was dropwise added thereto at an internal temperature of 20° C. or below under ice cooling. After the completion of the dropwise addition, the cooling bath was removed, and the mixture was allowed to stand at room temperature for 1 hr. The temperature was gradually raised, and the mixture was stirred at 95° C. for 1 hr. The reaction mixture was poured onto ice, and concentrated aqueous ammonia was added thereto for alkalification, followed by extraction with ethyl acetate. The extract was dried over magnesium sulfate, and the solvent was distilled off in vacuo to prepare a solid mixture of 2-amino- 3-nitro-4-n-propylpyridine with 2-amino-5-nitro-4-n-propylpyridine.

This mixture was suspended in methanol and catalytically hydrogenated in the presence of palladium carbon. The palladium carbon was removed by filtration, and the solvent was distilled off in vacuo. The residue was purified by silica gel chromatography. The yield was 2.6 g (brown crystal).

NMR (90 MHz, CDCl$_3$, δ value): 7.55(d, 1H,J=8 Hz), 6.50(d, 1H,J=8 Hz),3.80 (bs, 4H), 2.47 (t, 2H, J=7 Hz), 1.88~1.40(m, 2H), 1.00(t,3H, J=7 Hz)

(3) 2-Ethyl-7-n-propyl-imidazo[4,5-b]pyridine

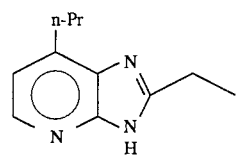

2.6 g (0.017M) of 2,3-diamino-4-n-propylpyridine and 1.4 ml (0.019M) of propionic acid were added to 15 ml of phosphoric acid, and the mixture was heated at 140° to 150° C. for 20 hr. It was cooled to room temperature, poured into a cold aqueous NaOH solution and then extracted with ethyl acetate. The extract was dried over magnesium sulfate, and the solvent was distilled off in vacuo to prepare a substantially pure brown oleaginous intended product. The yield was 2.9 g (this compound was used as a starting material in the preparation of the following raw material (29)) .

NMR(90 MHz, CDCl$_3$, δ value): 8.10 (d, 1H, J=8 Hz), 7.02 (d, 1H, J=8 Hz), 3.10 (q, 4H, J=7 Hz), 2.08~1.68 (m, 2H), 1.56 (t,3H, J=7 Hz), 1.04 (t, 3H, J=7 Hz)

PREPARATION EXAMPLE 11

2-Cyclopropyl-7-methyl-3H-imidazo[4,5-b]pyridine

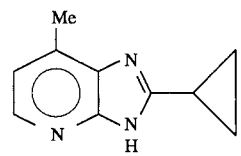

30 ml of cyclopropanecarboxylic acid and 70 ml of phosphoric acid (85%) were added to 15 g of 2,3-diamino-4-methylpyridine, and the mixture was stirred at an internal temperature of 130° C. for 12 hr. The reaction mixture was cooled, poured into a solution of 140 g of potassium hydroxide in 420 ml of water and then extracted with chloroform. The extract was dried over anhydrous magnesium sulfate and then concentrated. The residue was purified by column chromatography (chloroform : ethanol=97:3). The yield was 14.1 g, and the product was recrystallized from ethyl acetate-isopropyl ether to prepare the title compound in a pure form having a melting point of 203° to 204° C.

NMR (90 MHz, CDCl$_3$ , δ value): 8.16(d, 1H,J=8 Hz), 7.00(d, 1H,J=8 Hz),2.68 (s,3H) ,2.50~2.10(m, 1H), 1.40~1.12(m, 4H)

PREPARATION EXAMPLE 12

The following compounds were prepared according to the process described in the above-described Preparation Example 10(3) and Preparation Example 11. These compounds are used as a starting material in the process for preparing the compounds of the present invention.

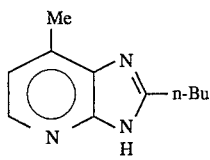
(1)

NMR(90 MHz, CDCl₃: δ value): 8.15(d, 1H, J=5 Hz), 7.02(d, 1H, J=5Hz), 3.06 (t, 2H, J=7 Hz), 2.68 (s, 3H), 2.14~1.70 (m, 2H), 1.70~1.10(m, 2H), 0.97 (t, 3H, J=7 Hz)

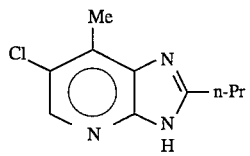
(2)

NMR(90 MHz, CDCl₃, δ value): 13.01 (bs; 1H), 8.22(s, 1H), 3.01 (t, 2H, J=7 Hz), 2.72 (s, 3H), 2.20~1.70 (m, 2H), 1.08 (t, 3H, J=7 Hz)

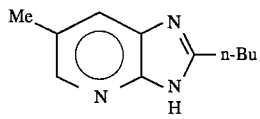
(3)

NMR (90 MHz, CDCl₃, δ value): 8.12 (d, 1H, J=1Hz), 7.81 (d, 1H, J=1Hz), 3.02 ( t, 2H, J=7 Hz), 2.49(s,3H), 2.20~1.72(m,2H),1.08(s,3H)

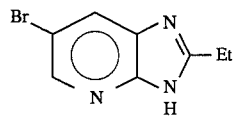
(4)

NMR(90 MHz, CDCl₃, δ value): 12.80(bs, 1H), 2.31 (d, 1H, J=2Hz), 8.12 (d, 1H, J=2Hz), 2.86 (q, 2H, J=7 Hz), 1.33 (t, 3H, J=7 Hz)

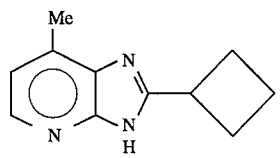
(5)

NMR (90 MHz, CDCl₃, δ value): 8.24 (d, 1H, J=8 Hz), 7.06 (d, 1H, J=8 Hz), 4.00 (quint, 1H, J=8 Hz), 2.75 (s, 3H), 2.86~1.96 (m,6H)

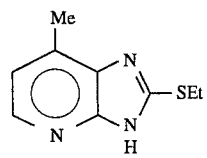
(6)

NMR (400 MHz, CDCl₃, δ value): 8.15(d, 1H, J=8 Hz), 7.01 (d, 1H, J=5 Hz), 3.40 (q, 2H, J=3Hz), 2.66 (s, 3H), 1.48 (t, 3H, J=8 Hz)

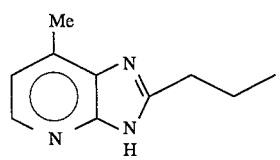
(7)

NMR (90 MHz, CDCl₃, δ value): 8.14 (d, 1H, J=5 Hz), 6.67 (d,1H,J=8 Hz), 4.10 (s, 3H), 3.00 (t, 2H, J=8 Hz), 2.20~1.70 (m, 2H), 1.08(t,3H,J=8 Hz)

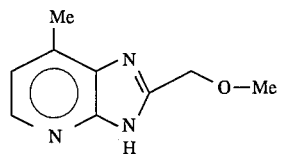
(8)

NMR (90 MHz, CDCl₃, (δ value): 8.23 (d, 1H, J=5 Hz), 7.02 (d, 1H, J=5 Hz), 4.88 (s, 2H), 3.57 (s, 3H), 2.70 (s, 3H)

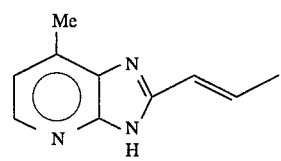
(9)

NMR (90 MHz, CDCl₃, δ value): 8.10 (d, 1H, J=5 Hz), 7.10~6.60 (m, 2H), 6.46 (dd, 1H, J=15 Hz, 1Hz), 2.58 (s, 3H), 1.99 (dd, 3H, J=6 Hz, 1 Hz)

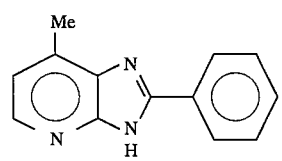
(10)

NMR (400 MHz, CDCl₃, δ value): 8.34~8.02 (m, 3H), 7.64~7.36 (m, 3H), 7.03 (d, 1H, J=5 Hz), 2.64 (s, 3H)

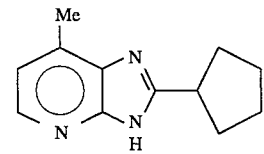
(10)

NMR (400 MHz, CDCl₃, δ value): 8.04 (d, 1H, J=5 Hz), 6.92 (d, 1H, J=5 Hz) , 3.50~3.00 (m, 1H), 2.52 (m, 3H), 2.24~1.46 (m, 8H)

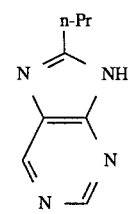
(12)

NMR (400 MHz, DMSO-d₆, δ value): 8.97 (1H, s), 8.84 (1H, s), 2.87 (2H, t, J=8 Hz), 1.88~1.78 (2H, m) , 0.96 (3H, t, J=8 Hz)

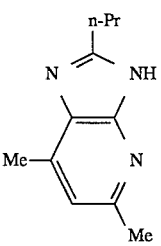
(13)

NMR (400 MHz, CDCl₃, δ value): 6.90 (1H, s), 2.98 (2H, t, J=8 Hz), 2.66 (3H, s), 2.65 (3H, s), 1.94~1.85 (2H, m), 1.037 (3H, t, J=8 Hz)

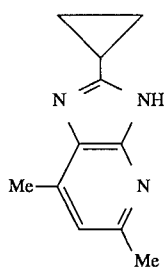

(14)

NMR (400 MHz, CDCl₃, δ value): 6.84 (1H, s), 2.66 (3H, s), 2.58 (3H, s), 2.21~2.15 (1H, m), 1.26~1.22 (2H, m), 1.12~1.07 (2H, m)

PREPARATION EXAMPLE 13

2-n-Butyl-1-{(5'-chloro-2'-cyanobiphenyl-4-yl)methyl}benzimidazole

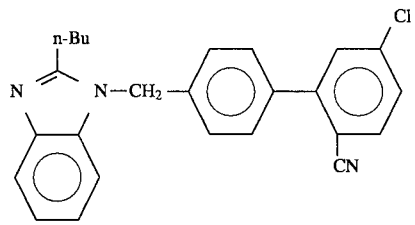

522 g of 2-n-butylbenzimidazole was dissolved in 10 ml of dimethylformamide and dropwise added to 130 g of sodium hydride. The mixture was stirred at room temperature for 30 min, and 920 mg of 2-(4-bromomethylphenyl)-4-chlorobenzonitrile dissolved in 10 ml of dimethylformamide was dropwise added thereto. The mixture was stirred at room temperature for 10 min, and the reaction mixture was filtered. The filtrate was concentrated and water and ethyl acetate were added to the residue. The organic phase was separated, dried over anhydrous magnesium sulfate and then concentrated. The residue was purified by column chromatography (chloroform: ethanol=98:2) (yield: 1.12 g).

NMR(90 MHz, CDCl₃, δ value): 7.82~6.95 (m, 11H), 5.38 (s, 2H), 2.83 ( t, 2H, J=7 Hz), 2.00~1.15 (m, 2H), 0.92 (t, 3H, J=7 Hz)

PREPARATION EXAMPLE 14

3-{(2'-Cyanobiphenyl-4-yl)methyl}-2-ethyl-3H imidazo[4,5-b]pyridiene

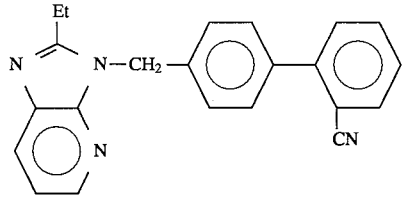

735 mg of 2-ethylimidazo[4,5b]pyridine was dissolved in 15 ml of dimethylformamide and dropwise added to 220 mg of sodium hydride. The mixture was stirred at room temperature for 30 min, and 1.4 g of 2-(4-bromomethylphenyl) benzonitrile dissolved in 15 ml of dimethylformamide was dropwise added thereto. The mixture was stirred at room temperature for 10 min and the reaction mixture was filtered. The filtrate was concentrated and water and ethyl acetate were added to the residue. The organic phase was separated, dried over anhydrous magnesium sulfate and then concentrated. The residue was purified by silica gel column chromatography, and eluation was conducted by gradually changing the eluent from 2% ethanol-98% chloroform to 5% ethanol-95% chloroform to separate regioisomers. The first eluted fraction was the intended title compound (yield: 800 mg).

NMR (90 MHz, CDCl₃, δ value): 8.34 (dd, 1H, J=1 Hz, 5 Hz), 8.02 (dd, 1H, J= 1Hz, 8 Hz), 7.78~6.95 (m, 9H), 5.55 (s, 2H), 2.87 (q, 2H, J=7 Hz), 1.42 (t, 3H, J=7 Hz)

The next eluted fraction was 1-{(2'-cyanobiphenyl- 4-yl)methyl}-2-ethyl-1H-imidazo[4,5-b]pyridine (yield: 200 mg).

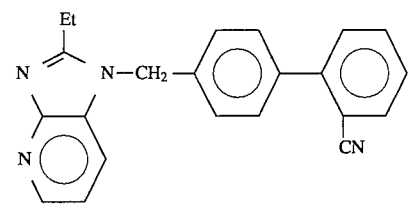

NMR (90 MHz, CDCl₃, δ value): 8.53(dd, 1H,J=1 Hz,5 Hz), 7.82~6.90(m, 10H), 5.41 (s,2H) ,2.93(q,2H,J=7 Hz), 1.47 (t,3H,J= 7 Hz)

The third eluted fraction was 4-{(2'-cyanobiphenyl- 4-yl)methyl}-2-ethyl-4H-imidazo[4,5-b]pyridine (yield: 570 g).

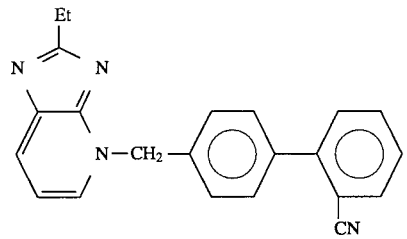

NMR (90 MHz, CDCl₃, δ value): 8.07 (d, 1H, J=7 Hz), 7.82~7.26 (m, 9H), 7.02 (dd, 1H, J=7 Hz, 7 Hz), 5.88 (s, 2H), 3.09 (q, 2H, J =7 Hz), 1.49 (t, 3H, J=7 Hz)

The structures of the regioisomers were determined by measuring the NOE (nuclear overhouser effect).

PREPARATION EXAMPLE 15

(a) 2-n-Butyl-1-[(2'-cyanobiphenyl-4-yl)methyl]- 1H-imidazo[4,5-c]pyridine and (b) 2-n-butyl-3-[( 2'-cyanobiphenyl-4-yl ) methyl]-3H-imidazo[4,5-c]pyridine

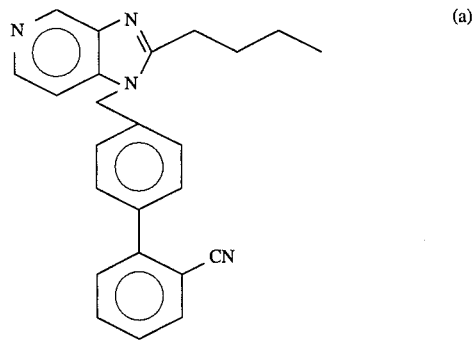

(a)

-continued (b)

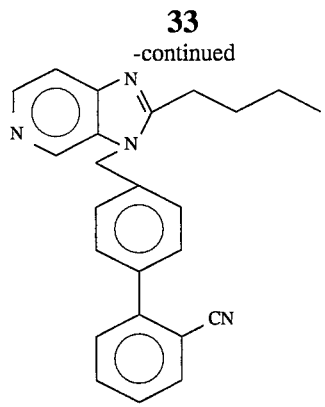

6.0 g (0.37M) of 2-n-butylimidazo[4,5-c]pyridine and 10 g (0.037M) of 2-(4-bromomethylphenyl)benzonitrile were suspended in 50 ml of dimethylformamide, and 1.6 g (0.040M) of sodium hydride was added thereto at once at room temperature under stirring. 30 min after the addition, water was added thereto, and the mixture was extracted with ethyl acetate. The extract was dried over magnesium sulfate. The solvent was distilled off in vacuo, and the residue was purified by silica gel chromatography. The first eluted fraction was 2-n-butyl-3-[2'-cyanobiphenyl-4-yl)methyl]-3H-imidazo[4,5-c]pyridine (yield 160 mg, brown oleaginous substance), and the next eluted fraction was 2-n-butyl-1-[(2'-cyanobiphenyl-4-yl)methyl]-1H-imidazo[ 4,5-c]pyridine (yield 200 mg, brown oleaginous substance).

(a) NMR (90 MHz, CDCl₃, δ value): 8.60 (s, 1H), 8.38 (d, 1H, J=5 Hz), 7.82~7.00 (m, 9H), 5.46 (s, 2H), 2.92 (t,2H, J=7 Hz), 2.08 ~1.30 (m, 4H), 0.96 (t, 3H, J=7 Hz).

(b) NMR (90 MHz, CDCl₃, δ value): 9.04 (s, 1H),8.32 (d, 1H,J=8 Hz), 7.80~7.00 (m, 9H), 5.40 (s, 2H), 2.90 (t, 2H, J=7 Hz), 2.07 ~1.20 (m, 4H), 0.96 (t, 3H, J=7 Hz)

PREPARATION EXAMPLE 16

The following compounds usable as a starting material for synthesizing the compounds of the present invention were prepared according to the process described in Preparation Examples 13 to 15.

The chemical structural formulae of the prepared compounds will be described below.

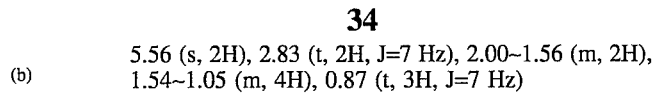

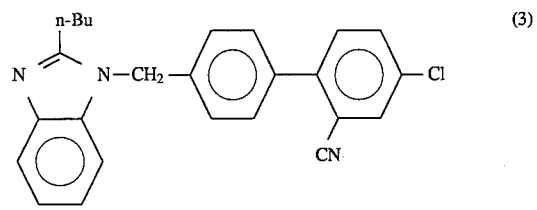
(1)

NMR (90 MHz, CDCl₃, δ value): 7.85~7.62 (m, 1H), 7.45~6.85 (m, 10H), 5.40 (s, 2H), 3.75 (s, 3H), 2.86 (t, 2H, J=7 Hz), 2.02 ~1.10 (m, 4H), 0.92 (t, 3H, J=7 Hz)

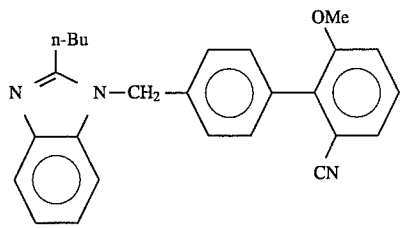
(2)

NMR (90 MHz, CDCl₃, δ value): 8.34 (dd, 1H, J=1 Hz, 5 Hz), 8.01 (dd, 1H, J=1 Hz, 8 Hz), 7.78~7.06 (m, 9H), 5.56 (s, 2H), 2.83 (t, 2H, J=7 Hz), 2.00~1.56 (m, 2H), 1.54~1.05 (m, 4H), 0.87 (t, 3H, J=7 Hz)

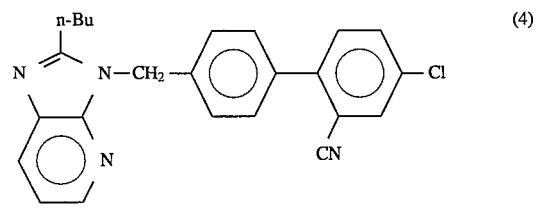
(3)

NMR (90 MHz, CDCl₃, δ value): 7.86~7.00 (m, 11H), 5.40 (s, 2H), 2.86 (t, 2H, J=7 Hz), 2.03~1.15(m, 4H), 0.93 (t, 3H, J=7 Hz)

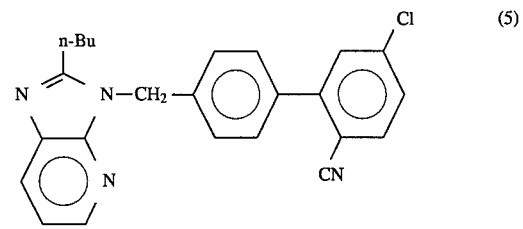
(4)

NMR (90 MHz, CDCl₃, δ value): 8.33(dd, 1H, J=1 Hz,5 Hz) ,8.01 (dd, 1H, J=1 Hz, 8 Hz), 7.74~7.05 (m, 8H), 5.56 (s, 2H), 2.83 (t, 2H, J=7 Hz), 2.00~1.15 (m, 4H), 0.92 (t, 3H, J= 7 Hz)

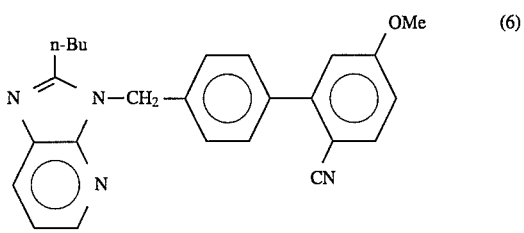
(5)

NMR (90 MHz, CDCl₃, δ value): 8.34 (dd, 1H, J=1 Hz,5 Hz) ,8.02(dd, 1H, J=1 Hz, 8 Hz), 7.72~7.05 (m, 8H), 5.56 (s, 2H), 2.84 (t, 2H, J=7 Hz), 2.00~1.17 (m, 4H), 0.92 (t, 3H, J= 7 Hz)

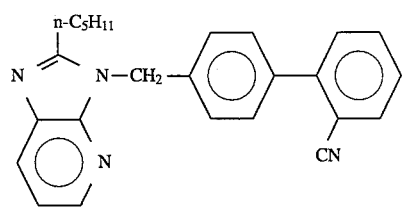
(6)

NMR(90 MHz, CDCl₃, δ value): 8.34 (dd, 1H, J=1 Hz, 5 Hz), 8.01 (dd, 1H, J=1 Hz, 8 Hz), 7.75~7.05 (m, 6H), 7.00~6.82 (m, 2H), 5.56 (s, 2H), 3.87 (s, 3H), 2.85 (t, 2H, J=7 Hz), 2.02~1.15(m, 4H), 0.93(t,3H, J=7 Hz)

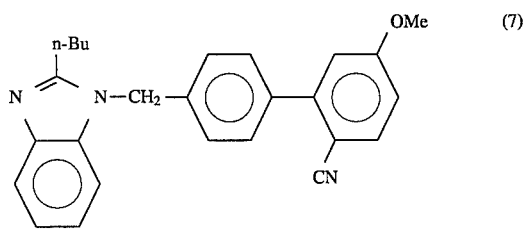
(7)

NMR(90 MHz, CDCl₃, δ value): 7.83~7.35 (m, 4H), 7.33~6.98 (m, 5H), 6.98 ~6.77 (m, 2H), 5.40 (s, 2H), 3.87 (s, 3H), 2.87 (t, 2H, J=8 Hz), 2.06~1.22 (m, 4H), 0.94 (t, 3H, J=7 Hz)

(8)

NMR (90 MHz, CDCl₃, δ value): 8.34 (dd, 1H, J=1Hz, 5 Hz), 8.02 (dd, 1H, J=1 Hz, 8 Hz), 7.75~7.12 (m, 8H), 5.57 (s, 2H), 2.82 (t, 2H, J=7 Hz), 2.10~1.62(m,2H), 1.02(t,3H,J= 7 Hz)

(9)

NMR (90 MHz, CDCl₃, δ value): 8.34 (dd, 1H,J=1 Hz,5 Hz),8.01 (dd, 1H,J=1 Hz, 8 Hz), 7.80~7.00 (m, 8H), 5.56 (s, 2H), 2.82 (t, 2H, J=7 Hz), 2.12~1.58 (m, 2H), 1.02 (t, 3H, J= 7 Hz)

(10)

NMR (90 MHz, DMSO-d₆, δ value): 7.85~7.00 (m, 12H), 5.39 (s, 2H), 2.84 (t, 2H, J=7 Hz), 2.04~1.20 (m, 4H), 0.92 (t, 3H, J=7 Hz)

(11)

(12)

NMR (90 MHz, CDCl₃, δ value): 7.80~6.70 (m, 11H), 5.36 (s, 2H), 2.85 (t, 2H, J=7 Hz), 2.04~1.20(m, 4H), 0.95 (t, 38, J=7 Hz)

(13)

NMR (90 MHz, CDCl₃, δ value): 7.80~6.70 (m, 11H), 5.32 (s, 2H), 2.86 (t, 2H, J=7 Hz), 2.04~1.24 (., 4H), 0.96 (t, 3H, J=7 Hz)

(14)

(15)

NMR (90 MHz, CDCl₃, δ value): 8.30(dd, 1H, J=8 Hz, 1Hz), 7.98 (dd, 1H, J=8 Hz, 1Hz), 7.78~7.04 (m, 9H), 5.54 (s, 2H), 2.86 (t, 2H, J=7 Hz), 2.02~1.22 (m, 4H), 0.94 (t, 3H, J=7 Hz)

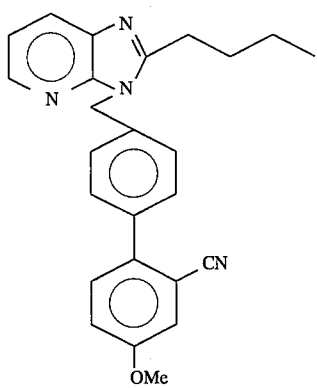
(16)
NMR (90 MHz, CDCl₃, δ value): 8.28 (dd, 1H, J=8 Hz, 1 Hz), 7.96 (dd, 1H, J=8 Hz, 1Hz), 7.50~6.96 (m, 8H), 5.52 (s, 2H), 3.76 (s, 3H), 2.84 (t, 2H, J=7 Hz), 2.04~1.16 (m, 4H), 0.92(t,3H,J=7 Hz)
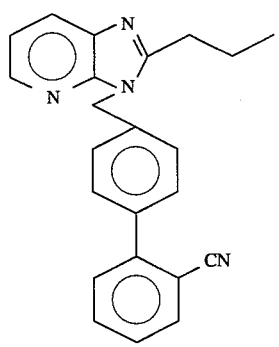
(17)
NMR (90 MHz, CDCl₃, δ value): 8.30 (dd, 1H, J=5 Hz, 1Hz), 7.96 (dd, 1H, J=8 Hz, 1Hz), 7.80~7.08 (m, 9H), 5.54 (s, 2H), 2.84 (t,2H,J=7 Hz) ,2.10~1.66(m,2H), 1.04 (t, 3H, J=7 Hz)
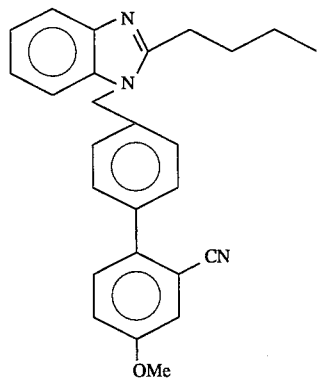
(18)
NMR (90 MHz, CDCl₃, δ value): 7.84~7.60(m, 1H), 7.52~6.98(m, 10H), 5.36 (s, 2H), 3.84 (s, 3H), 2.88 (t, 2H, J=7 Hz), 2.04~1.20 (m, 4H), 0.95 (t, 3H, J=7 Hz)
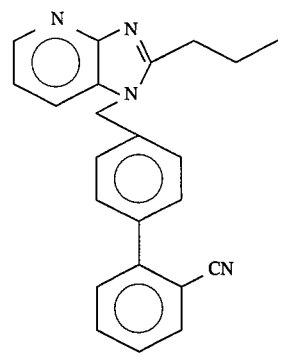
(19)
NMR (90 MHz, CDCl₃, δ value): 8.49(dd, 1H,J=8 Hz, 1Hz) ,8.07~7.01 (m, 10H), 5.48 (s, 2H), 2.90(t, 2H, J=7 Hz), 2.04~1.10 (m, 4H), 0.93(t,3H, J=7 Hz)
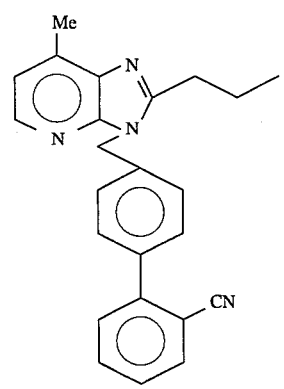
(20)
NMR (90 MHz, CDCl₃, δ value): 8.16 (d, 1H, J=5 Hz), 7.80~7.06 (m, 8H), 7.00 (d, 1H, J=5 Hz), 5.54 (s, 2H), 2.85 (t, 2H, J=7 Hz), 2.70 (s, 3H), 2.04~1.60 (m, 2H), 1.02 (t, 3H, J=7 Hz)
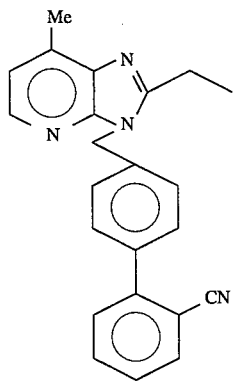
(21)
NMR (90 MHz, CDCl₃, δ value): 8.16(d, 1H,J=8 Hz), 7.76~7.08(m,8H),7.00 (d, 1 H, J=8 Hz), 5.54 (s, 2H), 2.88 (q, 2H, J=7 Hz), 2.72 (s, 3H), 1.40 (t, 3H, J=7 Hz)

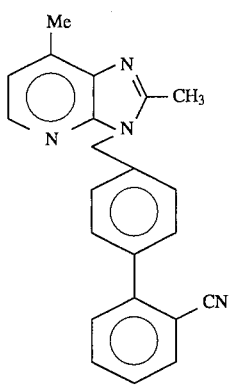
(22)
NMR (90 MHz, CDCl₃, δ value): 8.17(d,1H J=5 Hz) 7.80~7.10(m, 8H) 7.02 (d, 1H, J=5 Hz), 5.52 (s, 2H), 2.72 (s, 3H), 2.63 (s,3H)
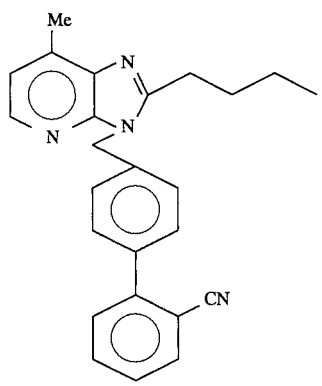
(23)
NMR (90 MHz, CDCl₃, δ value): 8.16 (d, 1H, J=5 Hz), 7.80~7.08 (m, 8H), 7.00 (d, 1H, J=5 Hz), 5.52 (s, 2H), 2.86 (t, 2H, J=6 Hz), 1.96~1.16(m,4H), 0.92(t,3H,J=6 Hz)
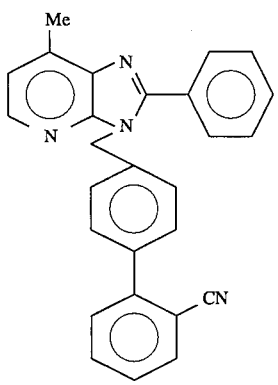
(24)
NMR (90 MHz, CDCl₃, δ value): 8.23 (d, 1H, J=8 Hz), 7.80~6.99(m, 14H), 5.60 (s,2H), 2.76(s,3H)
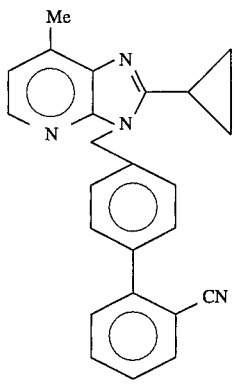
(25)
NMR (90 MHz, CDCl₃, δ value): 8.12(d, 1H,J=8 Hz), 7.80~7.10(m,8H), 6.94 (d, 1H, J=8 Hz), 5.62 (s, 2H), 2.64 (s, 3H) 2.36~2.14 (m, 1H), 1.40~0.90(m, 4H)
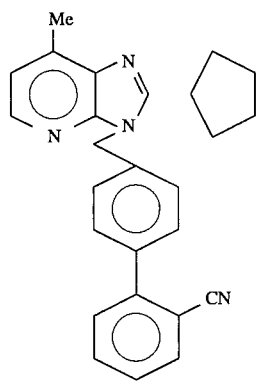
(26)
NMR (90 MHz, CDCl₃, δ value): 8.16 (d, 1H, J=8 Hz), 7.80~7.06 (m, 8H), 6.98 (d,1H,J=8 Hz),5.56(s,2H), 3.44~2.90(m, 1H), 2.70 (s, 3H), 2.40~1.40 (m, 8H)
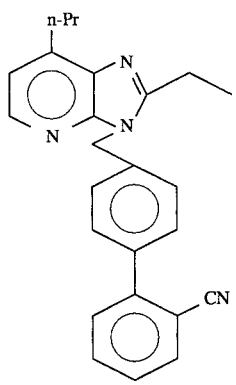
(27)
NMR (90 MHz, CDCl₃, δ value): 8.22 (d, 1H, J=8 Hz), 7.80~7.12 (m, 8H), 7.03 (d, 1H, J=8 Hz), 5.54 (s, 2H), 3.08 (t, 2H, J=6 Hz), 2.89(q,2H, J=6 Hz),2.10~1.70(m, 2H), 1.38 (t, 3H, J=6 Hz), 1.06 (t, 3H, J=6 Hz)

41
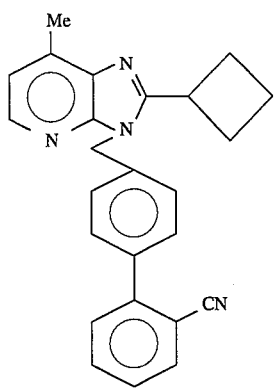
(28)
NMR (90 MHz, CDCl₃, δ value): 8.18(d, 1H,J=8 Hz), 7.80~6.94 (m,9H),5.48 (s, 2H), 3.80~3.40 (m, 1H), 2.74 (s, 3H), 2.66 ~1.88(m,6H)
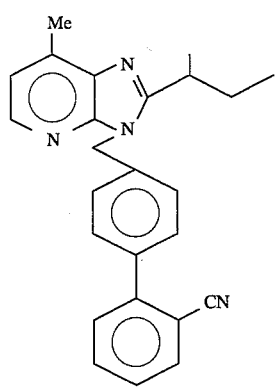
(29)
NMR (90 MHz, CDCl₃, δ value): 8.18 (d, 1H, J=5 Hz), 7.80~7.10 (m, 8H), 7.01 (d, 1H, J=5 Hz), 5.57 (s, 2H), 3.10~2.80 (m, 1H), 2.72 (s, 3H), 2.04~1.60 (m, 2H), 1.34 (d, 3H, J=6 Hz), 0.84 (t, 3H, J=6 Hz)
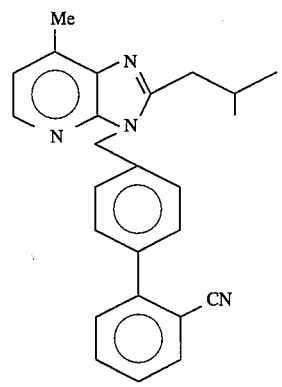
(30)
NMR (90 MHz, CDCl₃, δ value): 8.18 (d, 1H, J=8 Hz), 7.80~7.10 (m, 8H), 7.02 (d, 1H, J=8 Hz), 5.56 (s, 2H), 2.76 (d, 2H, J=6 Hz), 2.40~1.08 (m, 1H), 1.00 (d, 6H)
42
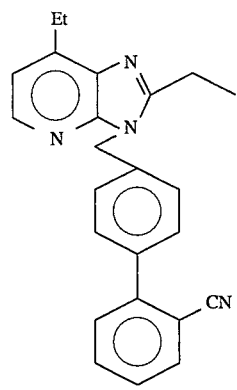
(31)
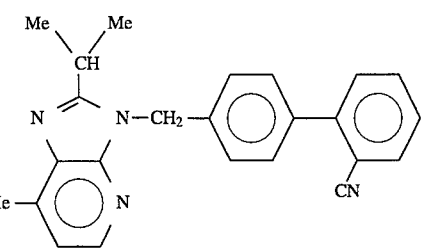
(32)
NMR (90 MHz, CDCl₃, δ value): 8.20 (d, 1H, J=5 Hz), 7.84~6.90 (m, 9H), 5.57 (s, 2H), 3.40~3.00 (m, 1H), 2.70 (m, 3H), 1.37 (s,6H,J=7 Hz)
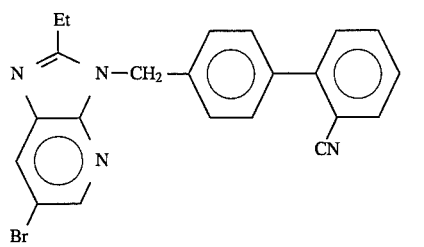
(33)
NMR (90 MHz, CDCl₃, δ value): 8.38 (d, 1H, J=2Hz), 8.13 (d, 1H, J=2Hz), 7.82 ~7.10 (m, 8H), 5.51 (s, 2H), 2.87 (q, 2H, J=7 Hz), 1.41 (t,3H,J=7 Hz)
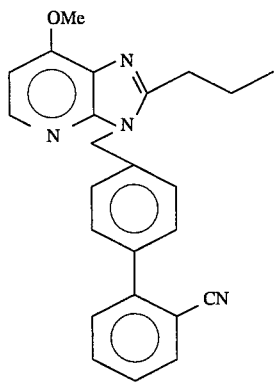
(34)
NMR (90 MHz, CDCl₃, δ value): 8.18 (d, 1H, J=6 Hz), 7.80~7.08 (m, 8H), 6.68 (d, 1H,J=6 Hz),5.52(s,2H), 4.10(s,3H),2.80 (t, 2H, J=6 Hz), 2.10~1.64 (m, 2H), 1.01 (t, 3H,J=6 Hz)

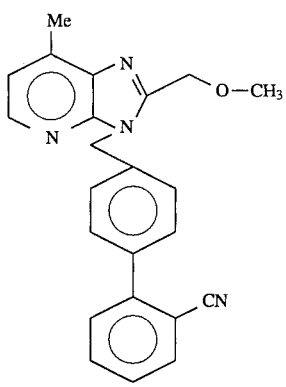

(35)

NMR (90 MHz, CDCl₃, δ value): 8.28 (d, 1H, J=6 Hz), 7.80~7.20 (m, 8H), 7.06 (d, 1H, J=6 Hz), 5.68 (s, 2H), 4.69 (s, 2H), 3.40 (s,3H), 2.72(s,3H)

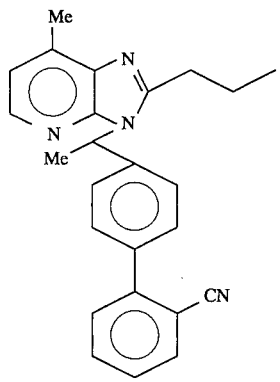

(36)

NMR (90 MHz, CDCl₃, δ value): 8.17 (d, 1H, J=8 Hz), 7.84~7.28 (m,8H), 7.00 (d, 1H, J=8 Hz), 6.16 (q, 1H, J=8 Hz), 2.80 (t, 2H, J=6 Hz), 2.69(s,3H), 2.17 (d,3H, J=8 Hz), 2.00 ~1.60 (m, 2H), 0.98 (t, 3H. J=6 Hz)

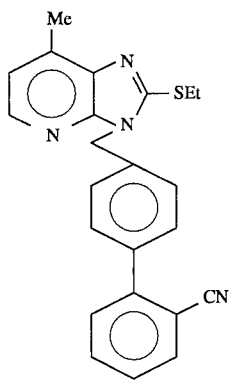

(37)

NMR (90 MHz, CDCl₃, δ value): 8.15 (d, 1H, J=5 Hz), 7.74 (dd, 1H, J=8 Hz, 1Hz), 7.61 (td, 1H, J=8 Hz, 1Hz), 7.51~7.39 (m, 6H), 6.99(d, 1H, J=8 Hz),5.46(s,2H), 3.40(q,2H,J= 7 Hz), 2.65 (s, 3H), 1.45 (t, 3H, J=7 Hz)

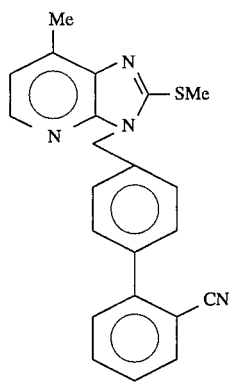

(38)

NMR (90 MHz, CDCl₃, δ value): 8.15 (d, 1H, J=8 Hz), 7.74 (d, 1H, J=8 Hz), 7.61 (td, 1H, J=8 Hz, 1Hz), 7.51~7.39 (m, 8H), 7.00 (d, 1H, J=8 Hz), 5.46 (s, 2H), 2.80(s, 3H), 2.65 (s,3H)

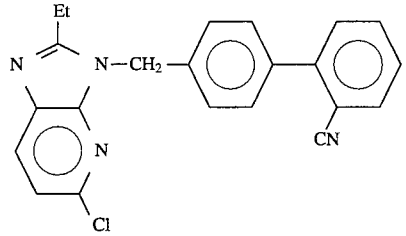

(39)

NMR(90 MHz, CDCl₃, δ value): 7.96 (d, 1H, J=8 Hz), 7.80~7.07 (m, 9H), 5.51 (s, 2H), 2.83 (q, 2H, J=8 Hz), 1.40 (t, 3H, J=8 Hz)

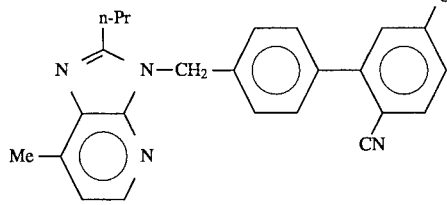

(40)

NMR (90 MHz, CDCl₃, δ value): 8.20(d, 1H,J=5 Hz), 7.72~7.05(m, 7H), 7.03 (d, 1H, J=8 Hz), 5.55 (s, 2H), 2.83 (t, 2H, J=7 Hz), 2.69 (s, 3H), 2.02~1.60 (m, 2H), 1.00 (t, 3H, J=7 Hz)

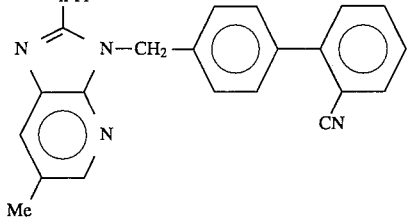

(41)

NMR (90 MHz, CDCl₃, δ value): 8.17 (d, 1H, J=1 Hz), 7.85~7.05 (m, 9H), 5.53 (s,2H), 2.81 (t, 2H, J=7 Hz), 2.47 (s, 3H), 2.08 ~1.61 (m,2H), 1.01 (t,3H,J=7 Hz)

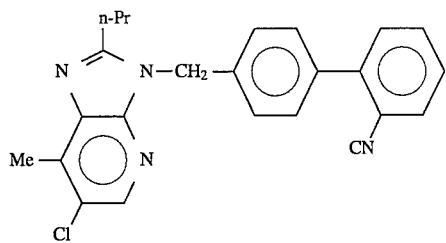
(42)

NMR (90 MHz, CDCl₃, δ value): 8.26(s, 1H), 7.78~7.05(m,9H),5.51 (s,2H), 2.83 (t, 2H, J=7 Hz), 2.71 (s, 3H), 2.03~1.57 (m, 2H),1.00(t,3H,J=7 Hz)

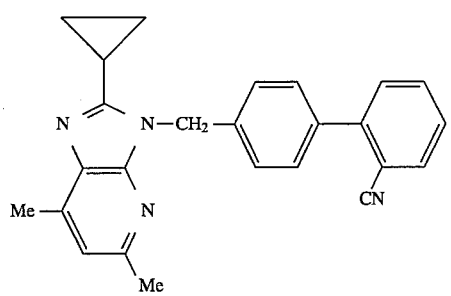
(43)

NMR (400 MHz, CDCl₃, δ value): 7.75 (1H, dd, J=8 Hz, 1 Hz), 7.63 (1H, td, J=8 Hz, 1Hz), 7.49 (2H, d, J=8 Hz), 7.46 (1H, dd, J=8 Hz, 1 Hz), 7.43 (1H, td, J=8 Hz, 1 Hz), 7.30(2H, d, J=8 Hz), 6.88 (1H, s), 5.64 (2H, s), 2.59(6H, s), 1.93~1.86(1H, m), 1.19~1.15 (2H, m), 1.03~0.98 (2H, m)

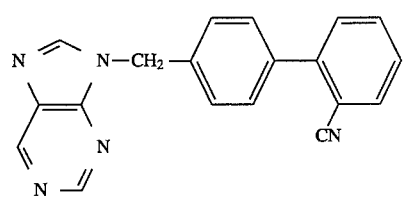
(44)

NMR (400 MHz, CDCl₃, δ value): 9.20(1H, s), 9.06(1H, s), 8.17 (1H, s), 7.76 (1H, dd, J=8 Hz, 1 Hz), 7.64 (1H, td, J=8 Hz, 1 Hz), 7.56 (2H, d, J=8Hz), 7.48~7.43 (4H, m), 5.54 (2H, s)

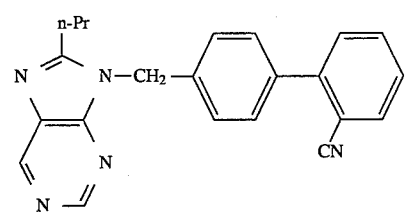
(45)

NMR (400 MHz, CDCl₃, δ value): 9.09 (1H, s), 8.97 (1H, s), 7.75 (1H, d, J=8 Hz), 7.63 (1H, td, J=8 Hz, 1 Hz), 7.52 (2H, d, J=8 Hz), 7.45 (1H, d, J=8 Hz), 7.44 (1H, td, J=8 Hz, 1 Hz), 7.28 (2H, d, J=8 Hz), 5.52 (2H, s), 2.85 (2H, t, J=8 Hz), 1.94~1.85 (2H, m), 1.03 (3H, t, J=8 Hz)

(46)

NMR(400 MHz, CDCl₃, δ value): 7.75 (1H, dd, J=8 Hz, 1Hz), 7.62 (1H, td, J=8 Hz, 1 Hz), 7.49~7.41 (4H, m), 7.23 (2H, d, J=8 Hz), 6.91 (1H, s), 5.54 (2H, s), 2.78 (2H, t, J=8 Hz), 2.64 (3H, s), 2.60 (3H, s), 1.82~1.73 (2H, m), 0.98 (3H, t, J=8 Hz)

PREPARATION EXAMPLE 17

(1) 4-Chloro-2,3-diaminopyridine

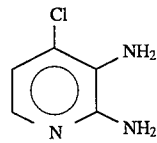

3.6 g of 2-amino-4-chloro-3-nitropyridine was added to 21 ml of methanol and 24 ml of concentrated hydrochloric acid, and the mixture was vigorously stirred. Powdery iron was added in small portions to the mixture. 10 min after the completion of the addition, the mixture was poured into an iced concentrated aqueous ammonia and extracted with ethyl acetate. The extract was dried over magnesium sulfate, and the solvent was distilled off in vacuo. The residue was purified by silica gel chromatography (CH₂Cl₂: MeOH= 20:1–10:1) to prepare 2.6 g of 4-chloro-2,3-diaminopyridine as a purplish white crystal.

NMR (90 MHz, CDCl₃, δ value): 7.20 (d, 1H, J=5 Hz), 8.48 (d, 1H, J=5 Hz), 5.74 (bs, 2H), 4.87 (bs, 2H)

(2) 7-Chloro-2-n-propyl-3H-imidazo[4,5-b]pyridine

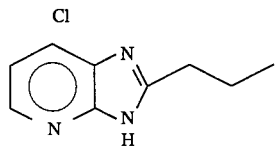

500 mg of 4-chloro-2,3-diaminopyridine was dissolved in THF, and 860 mg of dicyclohexylcarbodiimide, 570 mg of N-hydroxybenzotriazole and 0.4 ml of n-butyric acid were successively added thereto. The mixture was stirred overnight at room temperature, and the solid was removed by filtration. The solid was thoroughly washed with ethyl acetate. The mother liquor and wash liquid were collected, and the solvent was distilled off in vacuo. The residue was purified by silica gel chromatography (CH₂Cl₂: MeOH= 40:1). The solid obtained by distilling off the solvent in vacuo was heated to 140° C. The temperature of the solid was returned to room temperature after 30 min, and the solid was purified by column chromatography (Ch₂Cl₂: MeOH= 20:1) to prepare 200 mg of 7-chloro- 2-n-propyl-3H-imidazo [4,5-b]pyridine containing some impurities.

(3) 7-Chloro-2-n-propyl-3-[(2'-methoxycarbonylbiphenyl-4-yl)methyl]-3H-imidazo[4,5-b]pyridine

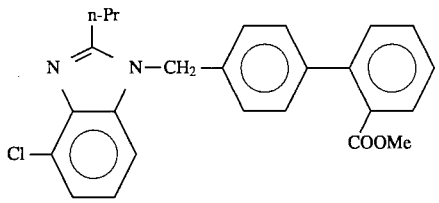

200 mg of the above-prepared 7-chloro-2-n-propyl-3H-imidazo[4,5-b]pyridine and 380 mg of methyl 2-(4-bromomethylphenyl)benzoate were dissolved in dimethylformamide, and 50 mg of sodium hydride was added to the solution. The mixture was stirred at room temperature for 20 min, and water was added thereto, followed by extraction with ethyl acetate. The extract was dried over magnesium sulfate, and the solvent was distilled off in vacuo. The residue was purified by silica gel chromatography (benzene:ethyl acetate=40:1+20:1) to prepare the intended product as a colorless oleaginous substance. The yield was 140 mg.

NMR(90 MHz, CDCl$_3$, δ value): 8.23 (d, 1H, J=8 Hz), 7.82 (dd, 1H, J=8 Hz, 1Hz), 7.51 (td, 1H,J=8 Hz, 1Hz), 7.40(td, 1H,J=8 Hz, 1Hz), 7.30(dd, 1H,J=8 Hz, 1Hz), 7.27~7.23 (m, 3H), 7.16 (d, 2H, J=8 Hz), 5.53 (s, 2H), 3.61 (s, 3H), 2.85 (t, 2H, J=8 Hz), 1.88~1.78 (m, 2H), 1.00(t,3H,J=8 Hz)

PREPARATION EXAMPLE 18

(1) 2-Mercapto-7-methyl-3H-imidazo[4,5-b]pyridine

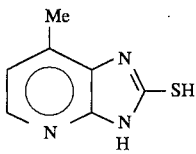

5 g of potassium hydroxide dissolved in 30 ml of ethanol was dropwise added at 20° C. or below to a solution of 15 g of 2,3-diamino-4-methylpyridine in 15 ml of carbon disulfide and 60 ml of methanol, and the mixture was refluxed for 2 hr. Water and 7 ml of concentrated hydrochloric acid were added thereto, and acetic acid was then added thereto to weakly acidify the mixture. The precipitated solid was recovered by filtration. The solid was washed twice with a small amount of methanol and then dried to prepare 12.3 g of 2-mercapto-7-methyl-3H-imidazo-[4,5-b]pyridine as a clayish solid.

NMR (400 MHz, DMSO-d$_6$): 13.01 (bs, 1H9,12.83(bs, 1H), 7.95(d, 1H,J= 5 Hz), 6.94 (d, 1H, J=5 Hz), 2.36 (s, 3H)

(2) 7-Methyl-2-methylthio-3H-imidazo[4,5-b]pyridine

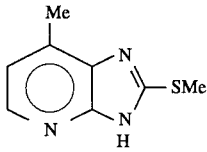

130 mg of sodium hydride was dropwise added at room temperature to a solution of 500 mg of 2-mercapto-7-methyl-3H-imidazo[4,5-b]pyridine in dimethylformamide. The mixture was stirred for 10 min, and 0.21 ml of iodomethane was added thereto, followed by reaction for 30 min. Water was added to the reaction mixture, and the mixture was extracted with ethyl acetate. The extract was dried over magnesium sulfate, and the solvent was distilled off in vacuo. The resultant solid was washed with a small amount of ethyl acetate to prepare 210 mg of 7-methyl-2-methylthio-3H-imidazo[ 4,5-b]pyridine as a mud yellow solid.

(3) 7-methyl-2-methylthio-3-[(2'-methoxycarbonylbiphenyl- 4-yl)methyl]-3H-imidazo[4,5-b]pyridine

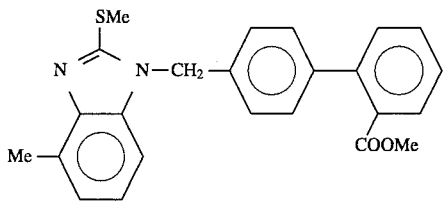

200 mg of 7-methyl-2-methylthio-3H-imidazo[4,5-b]pyridine and 370 mg of methyl 2-(4-bromomethylphenyl)benzoate was dissolved in dimethylformamide, and 48 mg of sodium hydride was added at room temperature to the solution under stirring. The reaction was allowed to proceed for 30 min. Water was added to the reaction mixture, and the mixture was extracted with ethyl acetate. The extract was dried over magnesium sulfate, and the solvent was distilled off in vacuo. The residue was purified by silica gel chromatography (benzene:ethyl acetate=10:1+3:2) to prepare the intended product as a colorless oleaginous substance. The yield was 60 mg.

NMR(90 MHz, CDCl$_3$, δ value): 8.23 (d, 1H, J=5 Hz), 7.82 (dd,1H,J=8 Hz, 1 Hz), 7.51 (td, 1H,J=8 Hz, 1Hz), 7.40 (td, 1H,J=8 Hz, 1Hz), 7.30 (dd, 1H, J=8 Hz, 1Hz), 7.27~7.23 (m, 3H), 7.16 (d. 2H, J=8 Hz), 5.53 (s, 2H), 3.61 (s, 3H), 2.85 (t, 2H, J=8 Hz), 1.88~1.78 (m, 2H), 1.00(t,3H,J=8 Hz)

PREPARATION EXAMPLE 19

2-Cyclopropyl-3-{(2'-methoxycarbonylbiphenyl-4-yl)methyl}- 7-methyl-3H-imidazo[4,5-b]pyridine

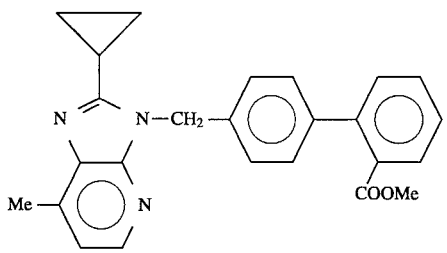

1.64 g of 2-cyclopropyl-7-methyl-3H-imidazo[4,5-b]pyridine dissolved in 30 ml of dimethylformamide was dropwise added to 400 mg of sodium hydride. The mixture was stirred at room temperature for 30 min, and 3.1 g of methyl-2-(4-bromomethylphenyl)benzoate dissolved in 20 ml of dimethylformamide was dropwise added thereto. The mixture was stirred for 10 min and then cooled, and an aqueous ammonium chloride solution was added thereto. The mixture was extracted with ethyl acetate. The extract was washed thrice with water, dried over anhydrous magnesium sulfate and then concentrated. The residue was subjected to column chromatography (chloroform: ethanol= 99:1). The first eluted isomer was the title compound (yield: 1.32 g).

NMR (90 MHz, CDCl$_3$, δ value): 8.16 (d, 1H, J=5 Hz), 7.85~7.63 (m, 1H), 7.56 ~7.10 (m, 1H), 7.22 (s, 4H), 6.98 (d, 1H, J=8 Hz), 5.62 (s, 2H), 3.60 (s, 3H), 2.64 (s, 3H), 2.10~1.80 (m, 1H), 1.30~0.82 (m, 4H)

2-hydroxymethyl-3-[(2'-methoxycarbonylbiphenyl-4-yl)methyl]-7-methyl-3H-imidazo[4,5-b]pyridine 50 ml (50 mmol) of a dichloromethane solution of 1M boron tribromide was added little by little dropwise to 100 ml of a dichloromethane solution of 3.3 g (8.2 mmol) of 3-[(2'-methoxycarbonyl-biphenyl-4-yl) methyl]-2-methoxymethyl- 7-methyl-3H-imidazo[4,5-b]pyridine, while stirred and cooled with ice. The mixture was further stirred at a room temperature for 12 hours. Methanol was added dropwise to the product mixture, while stirred and cooled with ice, and the solvent was distilled out at a reduced pressure. The residue was mixed with water and neutralized with sodium bicarbonate. It was weakly acidified with acetic acid and decanted to remove the water. Methanol was added to the residue and distilled out at a reduced pressure. It was re-crystallized from ethanol-isopropylether to obtain 2.4 g of the intended compound.

PREPARATION EXAMPLE 20

The following compounds were prepared according to the process described in Preparation Examples 17 to 19.

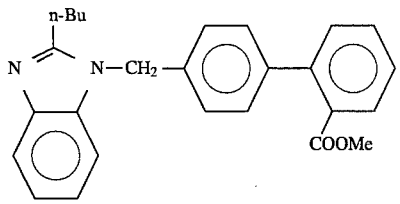
(1)

NMR(90 MHz, CDCl$_3$, δ value): 7.80~6.85 (m, 12H), 5.42 (s, 2H), 3.58 (s, 3H), 2.79(t, 2H, J=7 Hz), 1.85~1.00 (m, 4H), 0.86 (t, 3H, J=7 Hz)

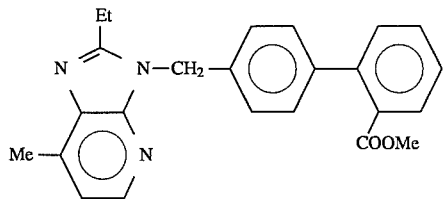
(2)

NMR (90 MHz, CDCl$_3$, δ value 8.21 (d, 1H, J=5 Hz), 7.90~7.72 (m, 1H), 7.58~6.94 (s, 8H), 5.52 (s, 2H), 3.59 (s, 3H), 2.87 (q, 2H, J=8 Hz), 2.69 (s, 3H), 1.35 (t, 3H, J=8 Hz)

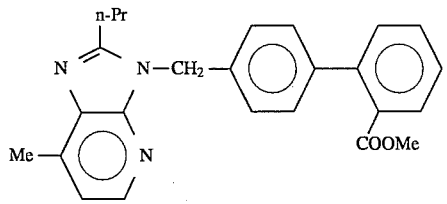
(3)

NMR (90 MHz, CDCl$_3$, δ value): 8.20 (d, 1H, J=5 Hz), 7.93~7.74 (m, 1H), 7.55~6.90 (m, 8H), 5.53 (s, 2H), 3.59 (s, 3H), 2.83 (t, 2H, J=7 Hz), 2.69 (s, 3H), 1.95~1.56 (m, 2H), 1.00 (t, 3H, J=7 Hz)

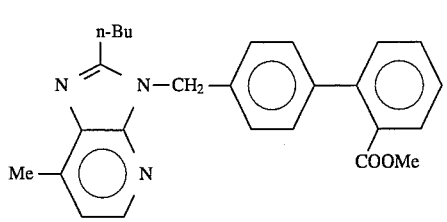
(4)

NMR (90 MHz, CDCl$_3$, δ value): 8.20 (d, 1H, J=5 Hz), 7.86~7.68 (m, 1H), 7.57~6.92 (m, 8H), 5.52 (s, 2H), 3.60 (s, 3H), 2.85 (t, 2H, J=7 Hz), 2.69 (s, 3H), 1.96~1.14 (m, 4H), 0.91 (t, 3H, J=7 Hz)

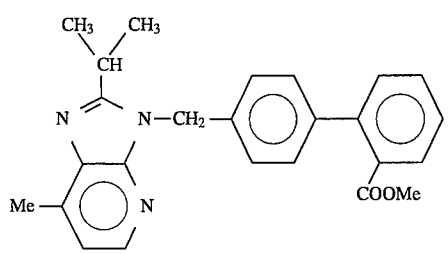
(5)

NMR (400 MHz, CDCl$_3$, δ value): 8.21 (d, 1H, J=5 Hz), 7.80 (d, 1H, J=8 Hz), 7.50 (t, 1H, J=8 Hz), 7.39 (t, 1H, J=8 Hz), 7.29 (d, 1H, J=8 Hz), 7.23 (d, 2H, J=8 Hz), 7.14 (d, 2H, J=8 Hz), 7.03 (d, 1H, J=5 Hz), 5.56 (s, 2H), 3.58 (s, 3H), 3.24~3.13 (m, 1H), 2.71 (s, 3H), 1.36 (d, 6H, J= 7 Hz)

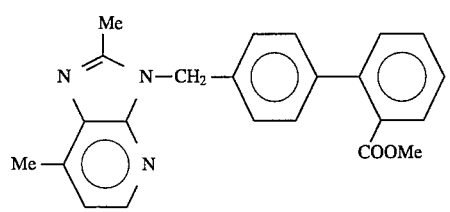
(6)

NMR (400 MHz, CDCl$_3$, δ value): 8.22 (d, 1H, J=5 Hz), 7.81 (d, 1H, J=8 Hz), 7.50 (t, 1H, J=8 Hz), 7.40 (t, 1H, J=8 Hz), 7.30 (d, 1H, J=8 Hz), 7.24 (d, 2H, J=8 Hz), 7.18 (d, 2H, J=8 Hz), 7.04 (d, 1H, J=5 Hz), 5.51 (s, 2H), 3.81 (s, 3H), 2.68 (s, 3H), 2.58 (s, 3H)

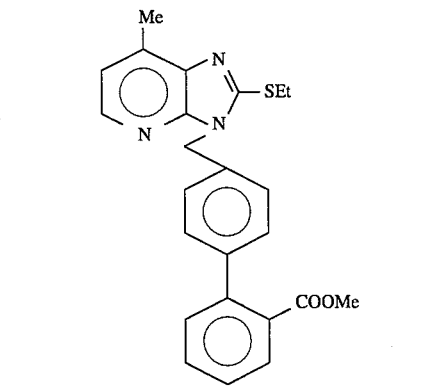
(7)

NMR (400 MHz, CDCl$_3$, δ value): 8.15 (d, 1H, J=5 Hz), 7.79 (d, 1H, J=8 Hz), 7.49 (td, 1H, J=8 Hz, 1 Hz), 7.38 (td, 1H, J=8 Hz, 1 Hz), 7.35~7.29 (m, 3H), 7.23 (d, 1H, J=8 Hz), 6.99 (dd, 2H, J=5 Hz, 1 Hz), 5.44 (s, 2H), 3.59 (s, 3H), 3.39 (q, 2H, J=8 Hz), 2.64 (s, 3H), 1.44 (t, 3H, J= 8 Hz)

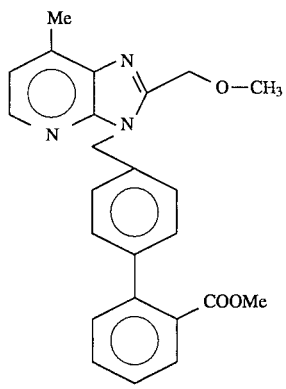
(8)

NMR (400 MHz, CDCl₃, δ value): 8.28 (d, 1H, J=5 Hz), 8.00 (d, 1H, J=8 Hz), 7.75 (td, 1H, J=8 Hz, 1 Hz), 7.46 (td, 1H, J=8 Hz, 1 Hz), 7.38 (d, 1H, J=8 Hz), 7.31~7.11 (m, 4H), 7.05 (d, 1H, J=5 Hz), 5.65 (s, 2H), 4.65 (s, 2H), 3.60 (s, 3H), 3.38 (s, 3H), 2.71 (s, 3H)

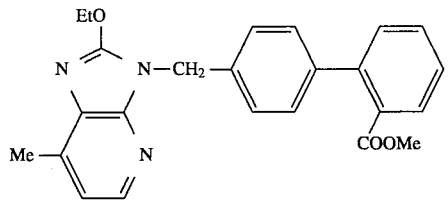
(9)

NMR (CDCl₃) δ; 8.05 (1H, d, J=5 Hz), 7.79 (1H, dd; J=1.8 Hz), 7.49 (1H, dt, J=1.8 Hz), 7.38 (1H, dt, J=1.8 Hz), 7.36 (2H, d, J=8 Hz), 7.30 (1H, dt, J=1.8 Hz), 7.23 (2H, d, J=8 Hz), 6.92 (1H, d, J=5 Hz), 5.30 (2H, s), 4.64 (2H, q, J=7 Hz), 3.61 (3H, s), 2.56 (3H, s), 1.47 (2H, t, J=7 Hz)

(10)

(11)

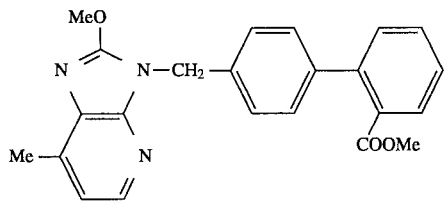

NMR (CDCl₃) δ: 8.06 (1H, d, J=5 Hz), 7.79 (1H, dd, J=1.8 Hz), 7.49 (1H, dt, J=1.8 Hz), 7.38 (1H, dt, J=1.8 Hz), 7.37 (2H, d, J=8 Hz), 7.29 (1H, dd, J=1.8 Hz), 7.23 (2H, d, J=8 Hz), 6.93 (1H, d, J=5 Hz), 5.30 (2H,s), 4.54 (2H, t,J=7 Hz), 3.60 (3H,s), 2.56 (3H, s), 1.91~1.82 (2H, m), 1.02 (3H, t, J=7 Hz)

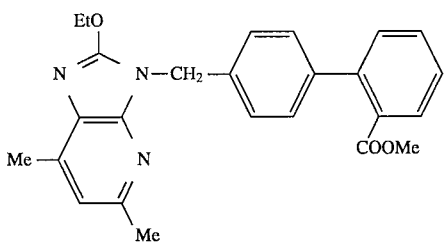
(12)

NMR(CDCl₃) δ: 7.79 (1H, dd, J=1.8 Hz), 7.49 (1H, dt, J=1.8 Hz), 7.38 (1H, dt, J=1.8 Hz), 7.35 (2H, d, J=8 Hz), 7.31 (1H, dd, J=1.8 Hz), 7.22 (2H, d, J=8 Hz), 6.79 (1H,s), 5.27 (2H, s), 4.60 (2H, q, J=7 Hz), 3.60 (3H, s), 2.55 (3H, s), 2.51 (3H, s), 1.44 (3H, t, J=7 Hz)

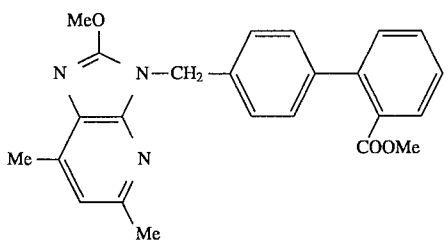
(13)

NMR (CDCl₃) δ: 7.80 (1H, dd, J=1.8 Hz), 7.50 (1H, dt, J=1.8 Hz), 7.39 (1H, dt, J=1.8 Hz), 7.32 (1H, dd, J=1.8 Hz), 7.25 (2H, d, J=8 Hz), 7.17 (2H, d, J=8 Hz), 6.57 (1H, s), 5.32 (2H, s), 3.59 (3H, s), 3.55 (3H, s), 2.48 (3H, s), 2.27 (3H, s),

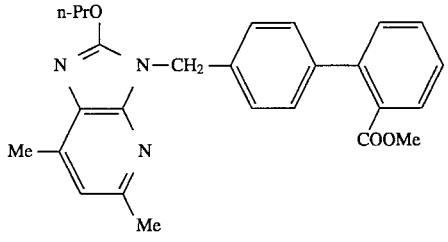
(14)

NMR(CDCl₃) δ: 7.79 (1H, dd, J=1.8 Hz), 7.49 (1H, dt, J=1.8 Hz), 7.38 (1H, dt, J=1.8 Hz), 7.35 (2H, d, J=8 Hz), 7.30 (1H, dd, J=1.8 Hz), 7.22 (2H, d, J=8 Hz), 6.79 (1H, s), 5.28 (2H, s), 4.49 (2H, t, J=7 Hz), 3.60 (3H, s), 2.56 (3H, s), 2.51 (3H, s), 1.88~1.78 (2H, m), 0.99 (3H, t, J=7 Hz)

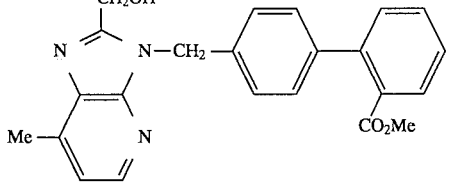
(15)

NMR (400 MHz, DMSO-d₆, δ value): 8.23 (1H, d, J=5 Hz), 7.73 (1H, dd, J=8 Hz, 1 Hz), 7.61 (1H, td, J=8 Hz, 1 Hz), 7.48 (1H, td, J=8 Hz, 1 Hz), 7.40 (1H, dd, J=8 Hz, 1 Hz), 7.28 (2H, d, J=8 Hz), 7.24 (2H, d, J=8 Hz), 7.14 (1H, d, J=5 Hz), 5.64 (2H, s), 4.73 (2H, s), 3.56 (3H, s), 2.59 (3H, s)

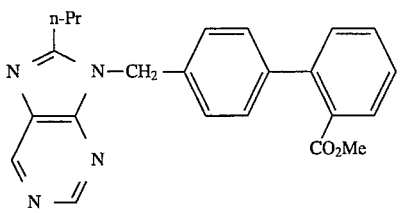

(16)

NMR (400 MHz, CDCl₃, δ value): 9.08 (1H, s), 8.97 (1H, s), 7.84 (1H, dd, J=8 Hz, 1 Hz), 7.53 (1H, td, J=8 Hz, 1 Hz), 7.42 (1H, td, J=8 Hz, 1 Hz), 7.31 (1H, dd, J=8 Hz, 1 Hz), 7.28 (2H, d, J=8 Hz), 7.20 (2H, d, J=8 Hz), 5.50 (2H, 3.61 (3H, s), 2.86 (2H, t, J=8 Hz), 1.95~1.85 (2H, 1.04 (3H, t, J=8 Hz)

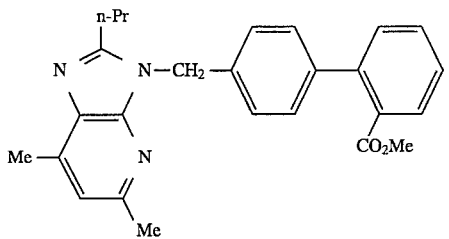

(17)

NMR (400 MHz, CDCl₃, δ value): 7.80 (1H, dd, J= 8 Hz, 1 Hz), 7.51 (1H, td, J=8 Hz, 1 Hz), 7.39 (1H, td, J=8 Hz, 1 Hz), 7.31 (1H, dd, J=8 Hz, 1 Hz), 7.23 (2H, d, J=8 Hz), 7.15 (2H, d, J=8 Hz), 6.90 (1H, s), 5.51 (2H, s), 3.59 (3H, s), 2.77 (2H, t, J=8 Hz), 2.64 (3H, s), 2.60 (3H, s), 1.81~1.72 (2H, m), 0.98 (3H, t, J=8 Hz)

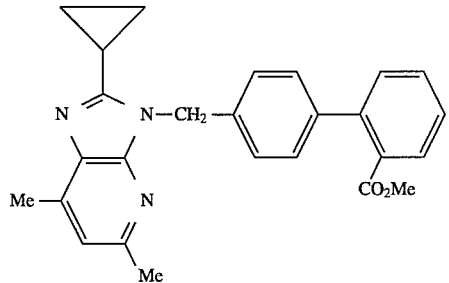

(18)

NMR (400 MHz, CDCl₃, δ value) 7.80 (1H, dd, J=8 Hz, 1 Hz), 7.50 (1H, td, J=8 Hz, 1 Hz), 7.39 (1H, td, J=8 Hz, 1 Hz), 7.31 (1H, dd, J=8 Hz, 1 Hz), 7.24 (2H, d, J=8 Hz), 7.21 (2H, d, J=8 Hz), 6.87 (1H, s), 5.60 (2H, s), 3.60 (3H, s), 2.58 (6H, s), 1.94~1.87 (1H, m), 1.19~1.15 (2H, m), 1.02~0.97 (2H, m)

EXAMPLE 1

2-n-Butyl-1-[{5'-chloro-2'-(1H-tetrazol-5-yl)-biphenyl-4-yl} methyl]benzimidazole

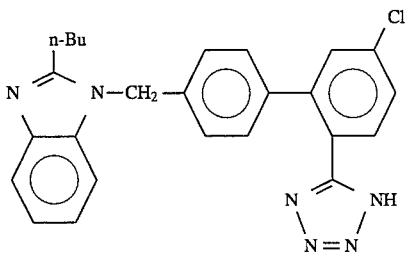

1.2 g of 2-n-butyl-1-{ (5'-chloro-2'-cyanobiphenyl-4-yl)methyl}benzimidazole prepared in Preparation Example 8, 910 mg of sodium azide and 750 mg of ammonium chloride were heated while stirring in 50 ml of dimethylformamide as a reaction solvent at an internal temperature of 125° C. for 50 hr. After cooling, a dilute sodium hydroxide solution and ethyl acetate were added thereto for phase separation, thereby obtaining a watery phase. The watery phase was weakly acidified with acetic acid, extracted with chloroform and washed with water. The extract was dried over anhydrous magnesium sulfate, and the residue was subjected to silica gel chromatography (chloroform:ethanol:acetic acid= 98:2:0.2). A fraciton of the intended title compound was concentrated and then recrystallized from ethyl acetate-isopropyl ethermethanol. The yield was 450 mg.

m.p. (° C.): 152~155

NMR (90 MHz, CDCl₃, δ value ): 7.70~7.00 (m, 7H), 7.06 (s, 4H), 5.50 (s, 2H), 2.82 (t, 2H, J=7 Hz), 1.90~1.00 (m, 4H), 0.87 (t, 3H, J=7 Hz)

EXAMPLE 2

2-Ethyl-7-methyl-3-[ { 2'-(1H-tetrazol-5-yl)-biphenyl-4-yl}methyl]-3H-imidazo[4,5-b]pyridine

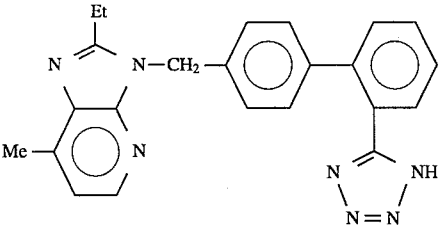

10 g (0.027M) of 3-[(2'-cyanobiphenyl-4-yl)-methyl]-2-ethyl-7-methyl-3H-imidazo[4,5-b] pyridine, 5.3 g (0.081M) of sodium azide and 5.6 g (0.041M) of triethylamine hydrochloride were suspended in 70 ml of N-methylpyrrolidone. The temperature of an oil bath was raised to 150° to 160° C. over a period of 20 min while stirring with a stirrer. The temperature was returned to room temperature after 6 hr, and water was added thereto, The mixture was washed with ethyl acetate (50 ml×3). The watery phase was acidified with acetic acid and extracted with ethyl acetate (100 ml× 5). The extract was dried over magnesium sulfate, and the solvent was distilled off in vacuo. The blackish brown oleaginous substance as the residue was purified by medium pressure column chromatography (SiO₂, ACOEt-:EtOH= 40:1÷2.0:1÷10:1). The yield was 11 g. Brown oleaginous substance.

This oleaginous substance was dissolved in ethyl acetate, and activated carbon was added thereto. The mixture was stirred at 50° C. for 15 min and then subjected to spontaneous filtration (no significant decoloring could be attained). The solvent was distilled off in vacuo, and the product was crystallized from hexanedichloromethane. The yield was 4.9 g. The product was a white crystal.

NMR (90 MHz, DMSO—d₆, δ value): 8.19 (d, 1H, J=5 Hz), 7.89~7.41 (m, 4H), 7.23~ 6.91 (m, 5H), 5.53 (m, 2H); 2.86 (q, 2H, J=6 Hz), 2.59 (m, 3H), 1.18 (t, 3H, J=6 Hz)

EXAMPLE 3

7-Methyl-2-n-propyl-3-[ { 2'-(1H-tetrazol-5-yl)-biphenyl-4-yl} methyl] - 3H- imidazo[ 4,5-b]pyridine

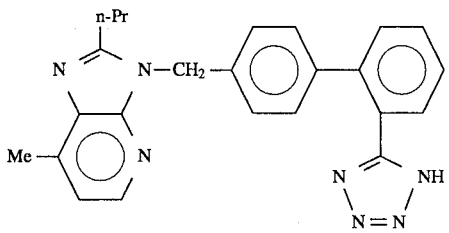

5.3 g of 3-[(2'-cyanobiphenyl-4-yl)methyl]-7-methyl-2-n-propyl-3H-imidazo[4,5-b] pyridine, 5.85 g of sodium azide and 6.19 g of triethylamine hydrochloride were heated in 120 ml of N-methylpyrrolidone as a reaction solvent at an internal temperature of 138° C. for 8 hr under stirring. After cooling, a dilute aqueous sodium hydroxide solution and ethyl acetate were added thereto to cause phase separation, thus obtaining a watery phase. The watery phase was weakly acidified with acetic acid and extracted thrice with ethyl acetate, and the extract was washed four times with water. Methanol was added to the washed extract to dissolve the precipitated crystal in the organic phase, and the organic phase was dried over anhydrous magnesium sulfate. The dried organic phase was concentrated, and the residue was subjected to silica gel chromatography (chloroform: ethanol : acetic acid=97:3:0.2). A fraction of the intended title compound was concentrated and recrystallized from ethanol. The yield was 4.6 g. The melting point was 200° to 202° C.

NMR (90 MHz, DMSO—$d_6$, δ value): 8.14 (d, 1H, J=5 Hz), 7.87~7.32 (m, 4H), 7.18~ 6.92 (m, 5H), 5.49 (s, 1H), 2.78 (t, 2H, J=7 Hz), 2.55 (s, 3H), 1.94~1.43 (m, 2H), 0.92 (t, 3H, J= 7 Hz)

EXAMPLE 4

The following compounds were synthesized according to the process described in Examples 1 to 3. The names, chemical structural formulae and physical constants of the synthesized compounds will be described below.

(1) 2-n-Butyl-1-[ { 2'-methoxy-6'-(1H-tetrazol- 5-yl)biphenyl-4-yl}methyl] benzimidazole

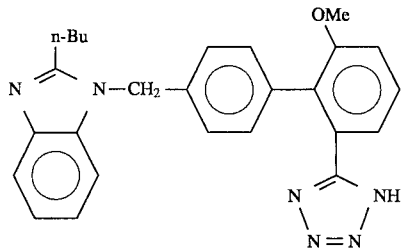

m.p. (° C.): 230.5~233

NMR (90 MHz, DMSO—$d_6$, δ value): 7.65~7.00 (m, 7H), 6.98 (s, 4H), 5.45 (s, 2H), 3.71 (s, 3H), 2.78 (t, 2H, J=7 Hz), 1.85~1.05 (m, 4H), 0.87 (t, 3H, J=7 Hz)

(2) 2-n-Pentyl-3-[ { 2'-(1H-tetrazol-5-yl)biphenyl-4-yl}methyl]-3H-imidazo[4,5-pyridine

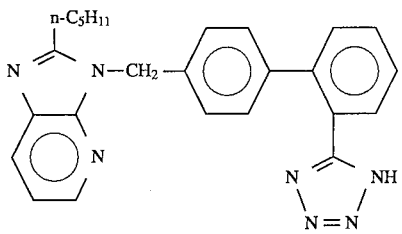

m.p. (° C.): 158~161

NMR (90 MHz, DMSO—$d_6$, δ value): 8.29 (dd, 1H, J=5 Hz), 7.99 (dd, 1H, J= 1 Hz, 8 Hz), 7.80~7.35 (m, 4H), 7.24 (dd, 1H, J=5 Hz, 8 Hz), 7.06 (s,4H), 5.51 (s,2H), 2.81 (t, 2H, J=8 Hz), 1.90~1.00 (m, 6H), 0.83 (t, 3H, J=7 Hz)

(3) 2-n-Butyl-1-[ { 4'-chloro-2'-(1H-tetrazol- 5-yl )biphenyl, 4-yl}methyl] benzimidazole

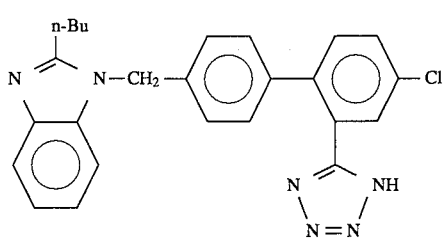

m.p. (° C.): 202~204

NMR (90 MHz, DMSO—$d_6$, δ value): 7.78~6.95 (m, 7H), 7.03 (s, 4H), 5.49 (s, 2H), 2.82 (t, 2H, J=7 Hz), 1.90~1.00 (m, 4H), 0.86 (t, 3H, J=7 Hz)

(4) 2-n-Butyl-5-methoxy-1-[ {2'-1H-tetrazol-5-yl)biphenyl-yl} methyl] benzimidazole

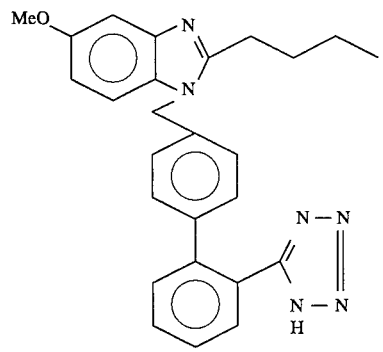

NMR (90 MHz, DMSO—$d_6$, δ value): 7.79~7.43 (m, 4H), 7.37 (d, 1H, J=9 Hz), 7.14 (d, 1H, J=3 Hz), 7.07 (s, 4H), 6.81 (dd, 1H, J=9 Hz, 3 Hz), 5.45 (s, 2H), 3.77 (s, 3H), 2.78 (t, 2H, J= 6 Hz), 1.85~1.10 (m, 4H), 0.86 (t, 3H, J=6 Hz)

(5) 2-n-Butyl-4-carbamoyl-1-[ { 2'-(1H-tetrazol- 5-yl)biphenyl-4-yl}methyl] benzimidazole

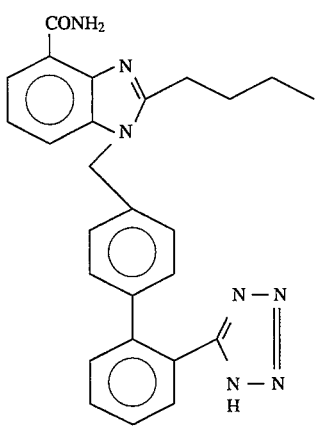

NMR (90 MHz, DMSO—d$_6$, δ value ): 7.95~6.84 (m, 11H), 5.53 (s, 2H), 2.90 (t, 2H, J=6 Hz), 1.93~1.13 (m, 4H), 0.87 (t, 3H, J=6 Hz)

(6) 2-n-Butyl-5-hydroxy-1-[ { 2'-(1H-tetrazol- 5-yl)biphenyl-4-yl}methyl] benzimidazole

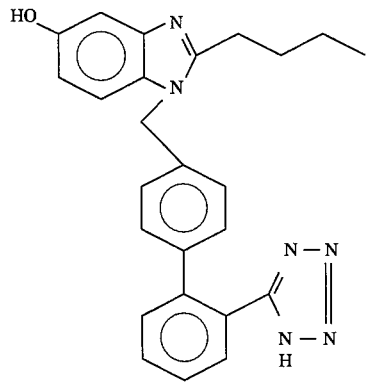

NMR (90 MHz, DMSO—d$_6$, δ value): 7.79~6.76 g(m, 10H), 6.67 (dd, 1H, J=9 Hz, 3 Hz), 5.39 (s, 2H), 2.77 (t, 2H, J=6 Hz), 1.87~1.11 (m, 4H), 0.86 (t, 3H, J=6 Hz)

(7) 2-n-Butyl-3-[ { 2'-(1H-tetrazol-5-yl)-biphenyl-4-yl}methyl]-3H-imidazo[ 4,5-b]pyridine

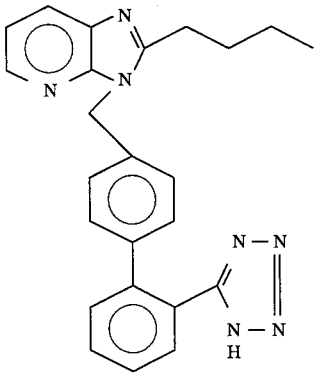

NMR (90 MHz, DMSO—d$_6$, δ value ): 8.34 (dd, 1H, J=5 Hz, 1 Hz), 8.02 (dd, 1H, J=8 Hz, 1 Hz), 7.81~7.41 (m, 4H), 7.27 (dd, 1H, J=5 Hz, 8 Hz), 7.07 (s, 4H), 5.55 (s, 2H), 2.82 (t, 2H, J= 6 Hz), 1.00~1.13 (m, 4H), 0.87 (t, 3H, J=6 Hz)

(8) 2-n-Butyl-1-[ { 5'-methoxy-2'-(1H-tetrazol-5-yl)biphenyl- 4-yl}methyl] benzimidazole

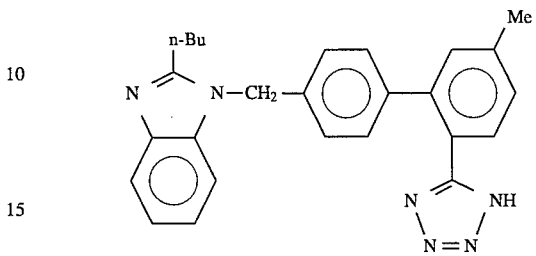

m.p. (° C.): 140~143

NMR (90 MHz, DMSO—d$_6$, δ value): 7.66~7.30 (m, 3H), 7.25~6.80 (m, 8H), 5.47 (s, 2H), 3.84 (s, 3H), 2.82 (t, 2H, J=7 Hz), 1.90~ 1.05 (m, 4H), 0.87 (t, 3H, J=7 Hz)

(9) 3-[ { 5'-Chloro-2'-(1H-tetrazol-5-yl)-biphenyl-4-yl}methyl]-2-n-propyl-3H-imidazo[ 4,5-b] pyridine

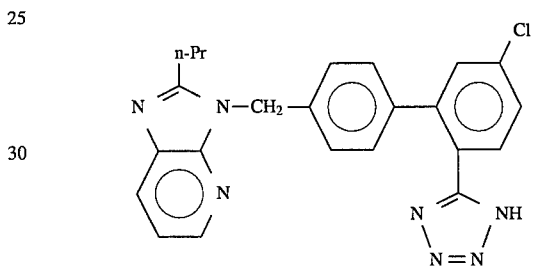

NMR (90 MHz, DMSO—d$_6$, δ value): 8.29 (dd, 1H, J= 1 Hz, 5 Hz), 8.00 (dd, 1H, J= 1 Hz, 8 Hz), 7.75~7.30 (m, 3H), 7.25 (dd, 1H, J=5 Hz, 8 Hz), 7.09 (s, 4H), 5.52 (s, 2H), 2.79 (t, 2H, J= 7 Hz), 1.95~1.45 (m, 2H), 0.93 (t, 3H, J=7 Hz)

(10) 3-[ { 4'-Chloro-2'-(1H-tetrazol-5-yl)biphenyl- 4-yl} methyl]-2-n-propyl-3H-imidazo[ 4,5-b] pyridine

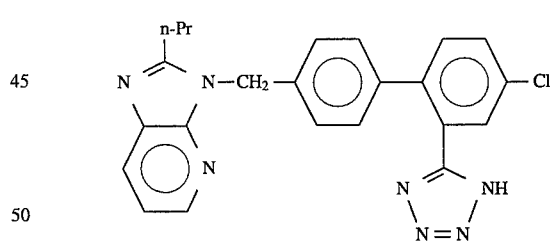

m.p. (° C.): 180~183

NMR (90 MHz, DMSO—d$_6$, δ value ): 8.29 (dd, 1H, J= 1 Hz, 5 Hz), 7.99 (dd, 1H, J= 1 Hz, 8 Hz), 7.80~7.37 (m, 3H), 7.25 (dd, 1H, J=5 Hz, 8 Hz), 7.06 (s, 4H), 5.51 (s, 2H), 2.79 (t, 2H, J= 7 Hz), 1.95~1.42 (m, 2H), 0.92 (t, 3H, J=7 Hz)

(11) 2-n-Butyl-3-[ { 2'-(1H-tetrazol-5-yl)biphenyl- 4-yl)methyl]-3H-imidazo[4,5-c] pyridine ammonium salt

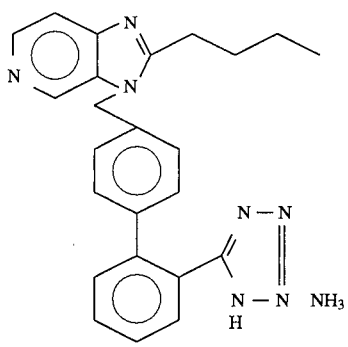

NMR (90 MHz, DMSO—d₆, δ value): 8.85 (s, 1H), 8.27 (d, 1H, J=5 Hz), 7.75~7.25 (m, 5H), 7.19~6.84 (m, 4H), 5.50 (s, 2H), 2.86 (t, 2H, J=6 Hz), 1.92~1.08 (m, 4H), 0.85 (t, 3H, J=6 Hz)

(12) 2-n-Propyl-1-[ { 2'-(1H-tetrazol-5-yl)biphenyl-4-yl}methyl]- 1H-imidazo[ 4,5-b] pyridine

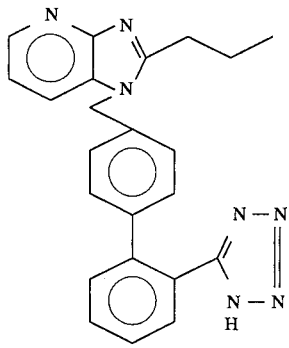

NMR (90 MHz, DMSO—d₆, δ value): 8.31 (dd, 1H, J=1 Hz, 5 Hz), 7.88 (dd, 1H, J=1 Hz, 8 Hz), 7.76~7.32 (m, 2H), 7.16 (dd, 1H, J=5 Hz, 8 Hz), 7.06 (s, 4H), 5.53 (s, 2H), 2.88 (t, 2H, J= 6 Hz), 1.90~1.16 (m, 2H), 0.92 (t, 3H, J=6 Hz)

(13) 2,7-Dimethyl-3[ {2'-(1H-tetrazol-5-yl)-biphenyl-4-yl}methyl]-3H-imidazo[ 4,5,b]pyridine ammonium salt

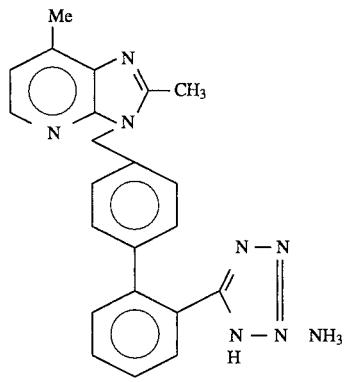

NMR (90 MHz, DMSO—d₆, δ value): 8.12 (d, 1H, J=5 Hz), 7.64~7.24 (m, 4H), 7.10~ 6.96 (m, 5H), 5.44 (s, 2H), 2.55 (s, 3H), 2.53 (s,3H)

(14) 2-n-Butyl-7-methyl-3-[ { 2'-(1H-tetrazol-5-yl)biphenyl- 4-yl}methyl]-3H-imidazo[4,5-b]pyridine ammonium salt

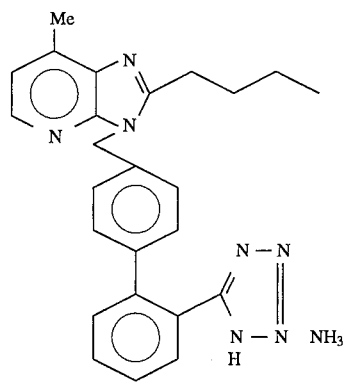

NMR (90 MHz, DMSO—d₆, δ value): 8.14 (d, 1H, J=5 Hz), 7.60~7.20 (m, 4H), 7.16~ 6.80 (m, 5H), 5.46 (s, 2H), 2.84 (t, 2H, J=7 Hz), 2.60 (s, 2H, J=7 Hz), 1.84~1.10 (m, 4H), 0.96 (t, 3H, J=6 Hz)

(15) 7-Methyl-2-phenyl-3[ { 2'-(1H-tetrazol-5-yl)biphenyl-4-yl} methyl], 3H-imidazo[4,5-b]pyridine ammonium salt

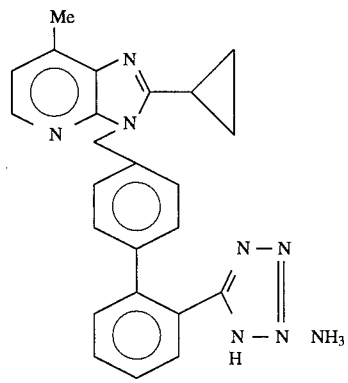

NMR (90 MHz, CDCl₃, δ value): 8.22 (d, 1H, J=5 Hz), 7.80~7.30 (m, 9H), 7.16 (d, 1H, J=5 Hz), 7.04~6.80 (m, 4H), 5.56 (s, 2H), 2.65 (s, 3H)

(16) 2-Cyclopropyl-7-methyl-3-[ { 2'-(1H-tetrazol- 5-yl)biphenyl-4-yl}methyl]-3H-imidazo-] 4,5-b] pyridine ammonium salt

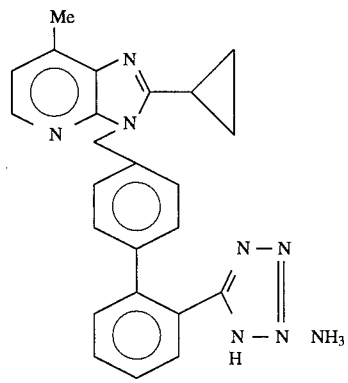

NMR (90 MHz, DMSO—d₆, δ value ): 8.06 (d, 1H, J=5 Hz), 7.60~7.16 (m, 4H), 7.12~ 6.88 (m, 5H), 5.54 (s. 2H), 2.50 (s, 3H), 2.40~ 2.04 (m, 1H), 1.08 (d, 4H, J=6 Hz)

(17) 2-Cyclopentyl-7-methyl-3-[ { 2'-(1H-tetrazol- 5-yl)biphenyl-4-yl}methyl]-3H-imidazo-[ 4,5-b] pyridine ammonium salt

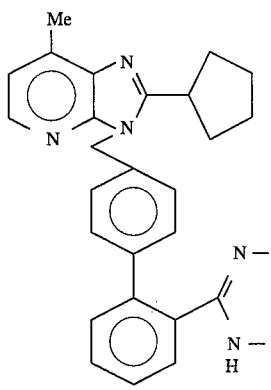

NMR (90 MHz, DMSO—d$_6$, δ value): 8.08 (d, 1H, J=5 Hz), 7.70~7.20 (m, 4H), 7.10~ 6.80 (m, 5H), 5.50 (s, 2H), 3.50~3.04 (m, 1H), 2.56 (s, 3H), 2.10~1.40 (m, 8H)

(18) 2-Ethyl-7-n-propyl-3-[ { 2'-(1H-tetrazol-5-yl )biphenyl- 4-yl}methyl]-3H-imidazo[ 4,5-b] pyridine ammonium salt

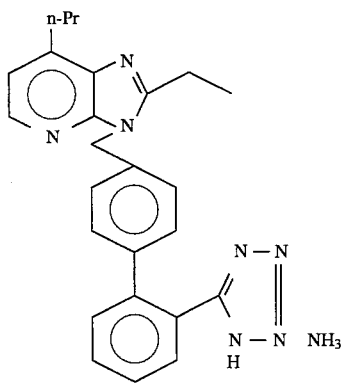

NMR (90 MHz, DMSO—d$_6$, δ value): 8.16 (d, 1H, J=5 Hz ), 7.68~7.18 (m, 4H), 7.10~ 6.90 (m, 5H), 5.44 (s, 2H), 3.10~2.60 (m, 4H), 2.0~1.60 (m, 2H), 1.18 (t, 3H, J=6 Hz), 0.96 (t, 3H, J=6 Hz)

(19) 2-Cyclobutyl-7-methyl-3-[ { 2'-(1H-tetrazol- 5-yl)biphenyl-4 -yl}methyl]-3H- imidazo-[ 4,5-b] pyridine ammonium salt

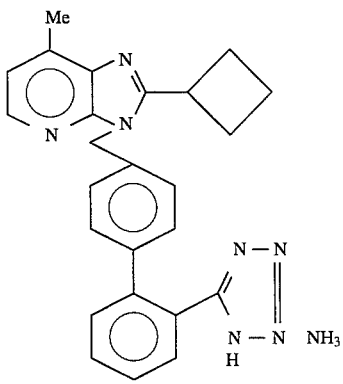

NMR (90MHz, DMSO—d$_6$, δ value): 8.14 (d; 1H, J=5 Hz), 7.64~7.20 (m, 4H), 7.16~ 6.84 (s, 5H), 5.38 (s, 2H), 3.90~3.60 (m, 1H), 2.60 (s, 3H), 2.55~1.80 (m, 6H)

(20) (±) 7-Methyl-2-(1-methylpropyl)-3-[{2'-( 1H-tetrazol-5-yl)biphenyl-4-yl}methyl]- 3H-imidazo[4,5-b]pyridine ammonium salt

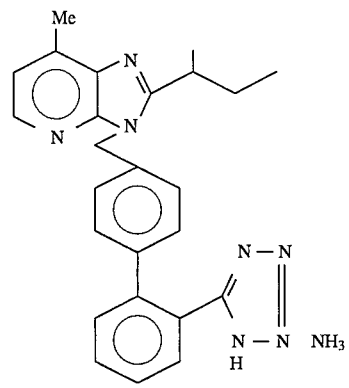

NMR (90 MHz, DMSO—d$_6$, δ value): 8.14 (d, 1H, J=5 Hz), 7.64~7.24 (m, 4H), 7.12~ 6.86 (m, 5H), 5.50 (s, 2H), 3.22~2.84 (m, 1H), 2.58 (s, 3H), 1.96~1.42 (m, 2H), 1.21 (d, 3H, J=6 Hz), 0.76 (t, 3H, J=6 Hz)

(21) (7-Methyl-2-(2-methylpropyl)-3-[ { 2'-(1H-tetrazol-5-yl)biphenyl-4-yl}methyl]- 3H-imidazo[ 4,5-b] pyridine ammonium salt

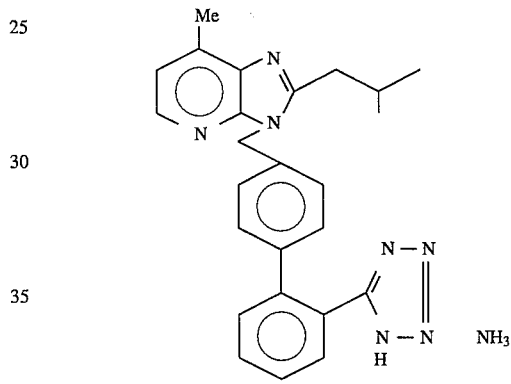

NMR (90 MHz, DMSO—d$_6$, δ value): 8.15 (d, 1H, J=5 Hz), 7.64~7.26 (m, 4H), 7.16~ 6.86 (m, 5H), 5.48 (s, 2H), 2.74 (d, 2H, J=6 Hz), 2.60 (s, 3H), 2.38~2.00 (m, 1H), 3.96 (d, 6H)

(22) 2,7-Diethyl-3-[ { 2'-(1H-tetrazol-5-yl)-biphenyl-4-yl}methyl]-3H-imidazo[ 4,5-b]-pyridine ammonium salt

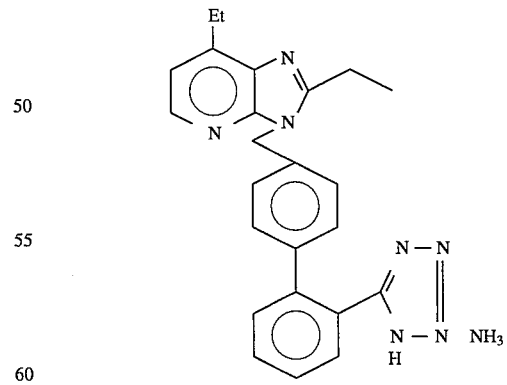

NMR (90 MHz, DMSO—d$_6$, δ value): 8.18 (d, 1H, J=5 Hz), 7.62~7.20 (m, 4H), 7.14~ 6.96 (m, 5H), 5.46 (s, 2H), 3.00 (q, 2H, J=6 Hz), 2.86 (q, 2H, J=6 Hz), 1.36 (t, 3H, J=6 Hz), 1.32 (t, 3H, J=6 Hz)

(23) 2-n-Butyl-1-[ { 2'-(1H-tetrazol-5-yl)biphenyl-4-yl}methyl] benzimidazole

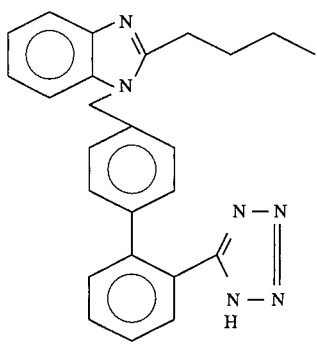

m.p. (° C.): 232~235

NMR (90 MHz, DMSO—d<sub>6</sub>, δ value): 7.80~7.34 (m, 6H), 7.33~6.95 (m, 2H), 7.05 (s, 4H), 5.48 (s, 2H), 2.82 (t, 2H, J=7 Hz), 1.93~1.08 (m, 4H), 0.88 (t, 3H, J=7 Hz)

(24) 2-n-Butyl-4-methyl-1-[ { 2'-(1H-tetrazol-5-yl)biphenyl- 4-yl}biphenyl-4-yl}methyl] benzimidazole ammonium salt

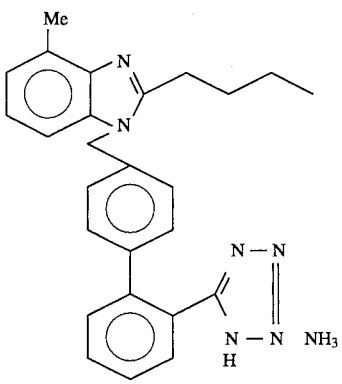

NMR (90 MHz, DMSO—d<sub>6</sub>, δ value): 7.79~7.41 (m, 4H), 7.39~6.87 (m, 7H), 5.50 (s, 2H), 2.82 (t, 2H, J=7 Hz), 2.54 (s, 3H), 1.86~1.20 (m, 4H), 0.88 (t, 3H, J=7 Hz)

(25) 2-n-Butyl-5-fluoro-1-[ { 2'-(1H-tetrazol-5-yl)biphenyl-4-yl}methyl]benzimidazole

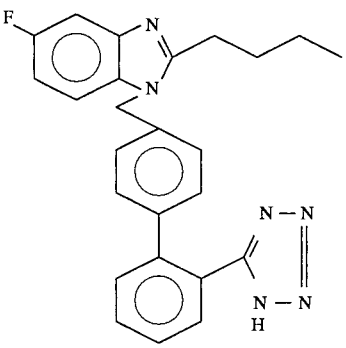

NMR (90 MHz, DMSO—d<sub>6</sub>, δ value): 7.75~7.27 (m, 6H), 7.19~6.87 (m, 5H), 5.49 (s, 2H), 2.81 (t, 2H, J=7 Hz), 1.85~1.13 (m, 4H), 0.86 (t, 3H, J=7 Hz)

(26) 2-n-Butyl-5-fluoro-3-[ {2'-(1H-tetrazol-5-yl)biphenyl-4-yl}methyl] benzimidazole

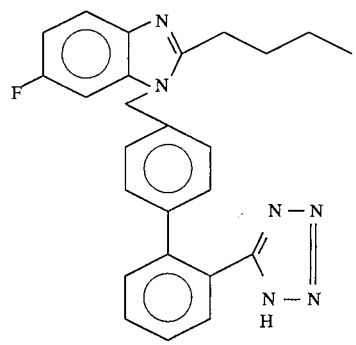

NMR (90MHz, DMSO—d<sub>6</sub>, δ value): 7.57~7.30 (m, 6H), 7.25~6.87 (m, 5H), 5.49 (s, 2H), 2.78 (t, 2H, J=7 Hz), 1.87~1.11 (m, 4H), 0.84 (t, 3H, J=7 Hz)

(27) 2-N-Butyl-3-[ { 4'-chloro-2'-(1H-tetrazol- 5-yl)biphenyl-4-yl}methyl]-3H-imidazo-[ 4,5-b]pyridine

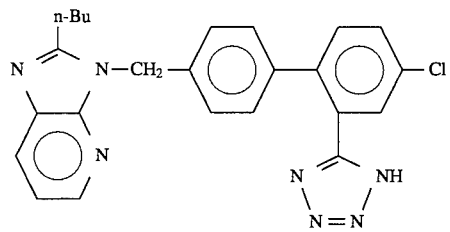

m.p. (° C.): 161~163

NMR (90 MHz, DMSO—d<sub>6</sub>, δ value): 8.28 (dd, 1H, J=1 Hz, 5 Hz), 7.99 (dd, 1H, J=1 Hz, 8 Hz), 7.82~7.35 (m, 3H), 7.24 (dd, 1H, J=5 Hz, 8Hz), 7.07 (s, 4H), 5.51 (s, 2H), 2.81 (t, 2H, J= 8 Hz), 1.90~1.00 (m, 4H), 0.85 (t, 3H, J=7 Hz)

(28) 2-Ethyl-3-[ { 2'-(1H-tetrazol-5-yl)biphenyl-4-yl}methyl]-3H-imidazo[ 4,5-b] pyridine

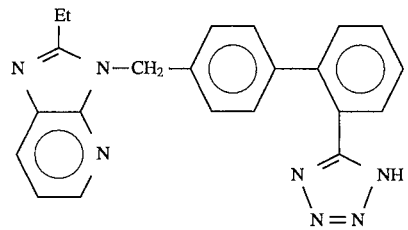

m.p. (° C.): 142~145

NMR (90 MHz, DMSO—d<sub>6</sub>, δ value): 8.34 (dd, 1H, J=1 Hz, 5 Hz), 8.02 (dd, 1H, J=1 Hz, 8 Hz), 7.75~7.37 (m, 4H), 7.24 (dd, 1H, J=5 Hz, 8 Hz), 7.06 (s, 4H), 5.50 (s, 2H), 2.83 (q, 2H, J= 7 Hz), 1.25 (t, 3H, J=7 Hz)

(29) 2-n-Butyl-3-[ { 5'-chloro-2'-(1H-tetrazol-5-yl)biphenyl- 4-yl}methyl]-3H-imidazo[ 4,5-b]-pyridine

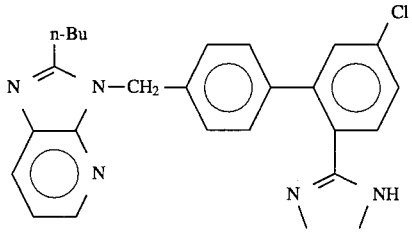

NMR (90 MHz, DMSO—d<sub>6</sub>, δ value): 8.29 (dd, 1H, J= 1 Hz, 5 Hz), 8.00 (dd, 1H, J= 1 Hz, 8 Hz), 7.75~6.90 (m, 4H), 7.09 (2,4H), 5.52 (s, 2H), 2.81 (t, 2H, J=7 Hz), 1.90~1.05 (m, 4H), 0.86 (t, 3H, J=7 Hz)

(30) 2-n-Butyl-3-[ { 5'-methoxy-2'-(1H-tetrazol-5-yl)biphenyl- 4-yl}methyl]-3H-imidazo[ 4,5-b]-pyridine

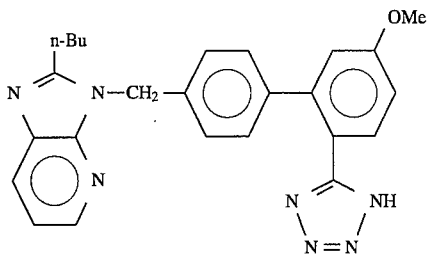

NMR (90 MHz, DMSO—d$_6$, δ value): 8.29 (dd, 1H, J=1 Hz, 5 Hz), 7.99 (dd, 1H, J=1 Hz, 8 Hz), 7.57 (d, 1H, J=9 Hz), 7.33~6.80 (m, 7H), 5.51 (s, 2H) 3.85 (s, 3H) 2.82 (t, 2H, J= 7 Hz), 1.90~1.05 (m, 4H), 0.86 (t, 3H, J=7 Hz)

(31) 2-n-Butyl-3-[ { 4'-methoxy-2'-(1H-tetrazol- 5-yl)biphenyl-4-yl}methyl]-3H-imidazo[ 4,5-b] -pyridine

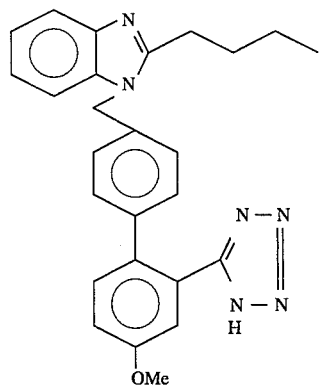

NMR (90 MHz, DMSO—d$_6$, δ value ): 8.33 (dd, 1H, J=5 Hz, 1 Hz), 8.03 (dd, 1H, J=8 Hz, 1 Hz), 7.59~6.80 (m, 8H), 5.53 (s, 2H), 3.86 (s, 3H), 2.85 (t, 2H, J=6 Hz), 1.93~1.10 (ms 4H), 0.88 (t, 3H, J=6 Hz)

(32) 2-n-Propyl-3-[ { 2'-(1H-tetrazol-5-yl)biphenyl-4-yl}methyl]-3H-imidazo[4,5-b] pyridine

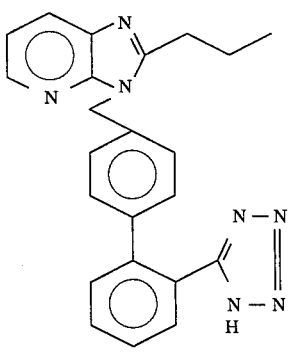

m.p. (° C.): 226–229.5

NMR (90 MHz, DMSO—d$_6$, δ value): 8.30 (dd, 1H, J=5 Hz), 8.01 (dd, 1H, J=8 Hz, 1 Hz), 7.82~7.37 (m, 4H), 7.26 (dd, 1H, J=8 Hz, 1 Hz), 7.09 (s, 3H), 5.54 (s, 2H), 2.79 (t, 2H, J=6 Hz), 1.95~1.39 (m, 2H), 0.92 (t, 3H, J=6 Hz)

(33) 2-n-Propyl-3-[{4'-methoxy-2'-(1H-tetrazol-5-yl)biphenyl- 4-yl}methyl] benzimidazole

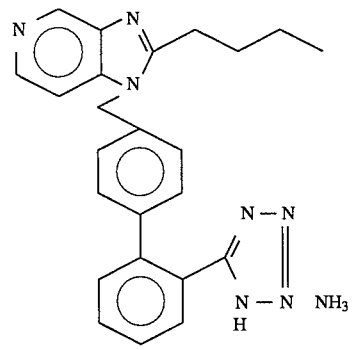

NMR (90 MHz, DMSO—d$_6$, δ value ): 7.73~7.03 (m, 7H), 7.00 (s, 4H), 5.46 (s, 2H), 3.83 (s, 3H), 2.82 (t, 2H, J=6 Hz), 1.88~1.12 (m, 4H), 0.86 (t, 3H, J=6 Hz)

(34) 2-n-Butyl-1-[ { 2'-(1H-tetrazol-5-yl) biphenyl-4-yl}methyl] benzimidazo[ 4,5-c] pyridine ammonium salt

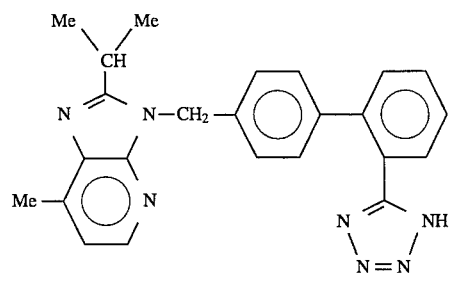

NMR (90 MHz, DMSO—d$_6$, δ value): 8.84 (s, 1H), 8.21 (d, 1H, J=5 Hz), 7.79~7.34 (m, 5H), 7.07 (s, 4H), 5.57 (s, 2H), 2.88 (t, 2H, J=6 Hz), 1.92~1.08 (m, 4H), 0.84 (t, 3H, J=6 Hz)

(35) 2-Isopropyl-7-methyl-3-[ { 2'-(1H-tetrazol- 5-yl)biphenyl-4-yl}methyl]-3H-imidazo[ 4,5-b] pyridine ammonium salt NMR (90 MHz, DMSO—d$_6$, δ value): 8.14 (d, 1H, J=5 Hz), 7.60~6.80 (m, 9H), 5.48 (s, 2H), 4.90 (bs, 4H), 3.42~3.00 (m, 1H), 2.56 (s, 3H), 1.23 (d, 6H, J=7 Hz)

(36) 2-Bromo-2-ethyl-3-[ { 2'-(1H-tetrazol-5-yl)-biphenyl-4-yl}methyl]-3H-imidazo[ 4,5-b] pyridine

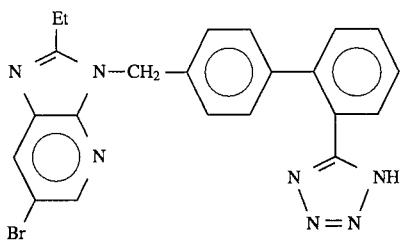

NMR (90 MHz, DMSO—d₆, δ value): 8.38 (d, 1H, J=2 Hz), 8.27 (d, 1H, J=2 Hz), 7.70~6.85 (m, 8H), 5.48 (s, 2H), 2.83 (q, 2H, J=7 Hz), 1.24 (t, 3H, J=7 Hz)

(37) 5-Chloro-2-ethyl-7-methyl-3-[{ 2'-(1H-tetrazol- 5-yl)biphenyl-4-yl}methyl]-3H-imidazo[ 4,5-b] pyridine

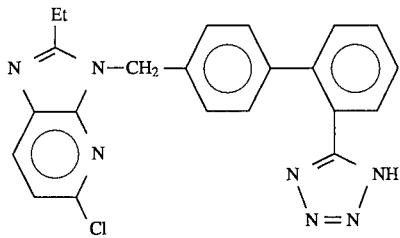

m.p. (° C.): 258 (dec)

NMR (90 MHz, DMSO—d₆, δ value): 8.07 (d, 1H, J=8 Hz), 7.70–7.35 (m, 4H), 7.31 (d, 1H, J=8 Hz), 7.07 (s, 4H), 5.46 (s, 2H), 2.81 (q, 2H, J=7 Hz), 1.24 (t, 3H, J=7 Hz)

(38) 3-[{5'-Chloro-2'-(1H-tetrazol-5-yl)biphenyl- 4-yl}methyl]-7-methyl-2-n-propyl-3H-imidazo[ 4,5-b] pyridine

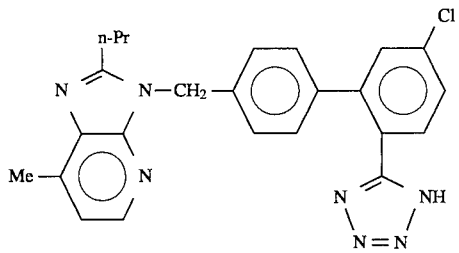

m.p. (° C.): 157~159

NMR (90 MHz, DMSO—d₆, δ value): 8.14 (d, 1H, J=8 Hz), 7.75~7.48 (m, 3H), 7.08~6.97 (m, 5H), 5.49 (s, 2H), 2.78 (t, 2H, J=7 Hz), 2.55 (s, 3H), 1.92~1.45 (m, 2H), 0.92 (t, 3H, J= 7 Hz)

(39) 6-Methyl-2-n-propyl-3-[ { 2'-(1H-tetrazol-5-yl)biphenyl- 4-yl}methyl]-3H-imidazo[4,5-b] pyridine

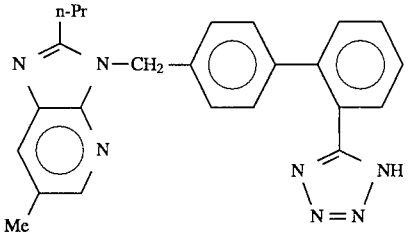

m.p. (° C.): 144~147

NMR (90 MHz, DMSO—d₆, δ value): 8.12 (d, 1H, J=1 Hz), 7.88~7.26 (m, 5H), 7.05 (s, 4H), 5.47 (s, 2H), 2.77 (t, 2H, J=7 Hz), 0.91 (t, 3H, J=7 Hz)

(40) 6-Chloro-7-methyl-2-n-propyl-3-[ { 2'-(1H-tetrazol-5-yl)biphenyl-4-yl}methyl]-3H-imidazo[ 4,5-b]pyridine

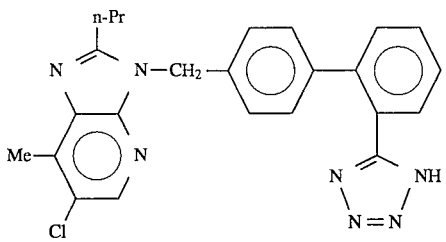

m.p. (° C.): 233–235

NMR (90 MHz, DMSO—d₆, δ value): 8.27 (s, 1H), 7.75~7.30 (m, 4H), 7.05 (s, 4H), 5.48 (s, 2H), 2.79 (t, 2H, J=7 Hz), 2.58 (s, 3H), 1.93~1.45 (m, 2H), 0.92 (t, 3H, J=7 Hz)

(41) 7-Methoxy-2-n-propyl-3-[{2'-(1H-tetrazol-5-yl)biphenyl- 4-yl}methyl]-3H-imidazo[ 4,5-b]pyridine

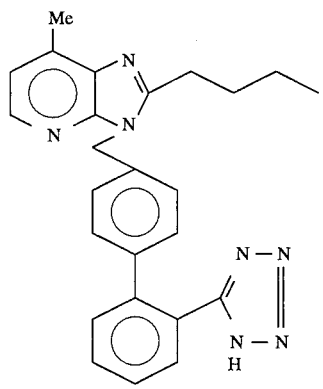

m.p. (° C.): 130~135

NMR (90 MHz, DMSO—d₆, δ value ): 8.11 (d, 1H, J=5 Hz), 7.60~6.88 (m, 8H), 6.80 (d, 1H, J=5 Hz), 5.42 (s, 4H), 4.04 (s, 3H), 2.76 (t, 2H, J=7 Hz), 1.96~1.50 (m, 2H), 0.92 (t, 3H, J=7 Hz)

(42) 2-Methoxymethyl-7-methyl-3-[ { 2'-(1H-tetrazol- 5-yl)biphenyl-4-yl}methyl]-3H-imidazo-[ 4,5-b] pyridine

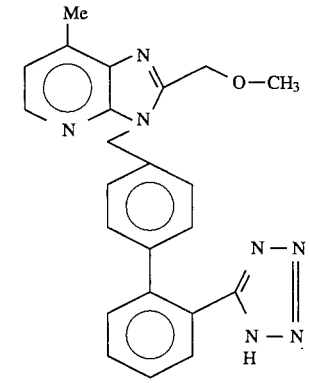

m.p. (° C.): 127~135

NMR (90 MHz, DMSO—d₆, δ value): 8.18 (d, 1H, J=5 Hz), 7.60~6.94 (m, 9H), 5.48 (s, 2H), 4.64 (s, 2H), 3.29 (s, 3H), 2.60 (s, 3H)

(43) 7-Methyl-2-n-propyl-3-[ {2'-(1H-tetrazol-5-yl)biphenyl- 4-yl}methyl]-3H-imidazo[4,5-b]pyridine ammonium salt

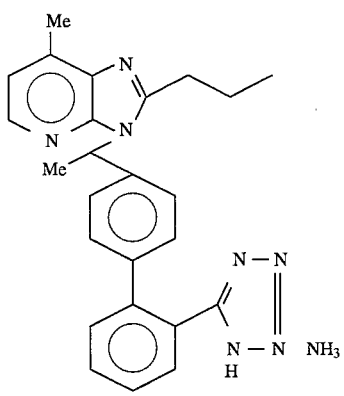

m.p. (° C.): 118~130

NMR (90 MHz, DMSO—d6, δ value): 8.10 (d, 1H, J=5 Hz), 7.68~7.36 (m, 4H), 7.32~ 6.92 (m, 5H), 6.02 (q, 1H, J=5 Hz), 2.80 (t, 2H, J=6 Hz), 2.58 (s, 3H), 2.08 (d, 3H, J=8 Hz), 1.96~ 1.50 (m, 2H), 0.96 (t, 3H, J=6 Hz)

(44) 2-Ethylthio-7-methyl-3-[ {2'-(1H-tetrazol- 5-yl)biphenyl-4-yl}methyl]-3H-imidazo-[ 4,5-b] pyridine ammonium salt

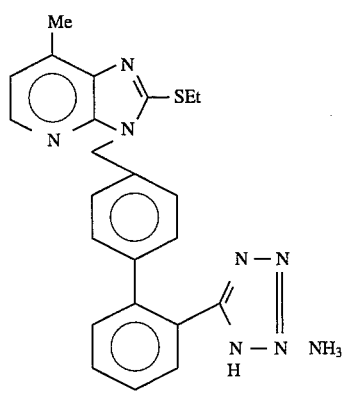

m.p. (° C.): 149~159

NMR (400 MHz, CDCl3 + DMSO—d6, δ value): 8.08 (d, 1H, J=5 Hz), 7.68 (dd, 1H, J=7 Hz, 1 Hz), 7.48 (td, 1H, J=8 Hz, 1 Hz), 7.44~7.37 (m, 2H), 7.19 (d, 2H, J=8 Hz), 7.09 (d, 2H, J=8 Hz), 6.99 (d, 1H, J=5 Hz), 4.97 (s, 2H), 3.38 (q, 2H, J=7 Hz), 2.61 (s, 3H), 1.45 (t, 3H, J=7 Hz)

(45) 7-Methyl-2-methylthio-3-[ { 2'-(1H-tetrazol- 5-yl )biphenyl-4-yl}methyl]-3H-imidazo-[ 4,5-b] pyridine ammonium salt

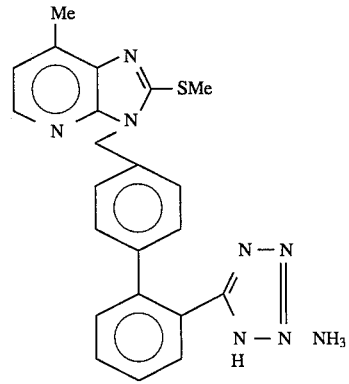

m.p. (° C.): 150~175

NMR (400 MHz, CDCl3 +DMSO—d6, δ value): 8.10 (d, 1H, J=5 Hz), 7.66 (dd, 1H, J=8 Hz, 1 Hz), 7.50~ 7.36 (m, 3H), 7.19 (d, 2H, J=8 Hz), 7.14 (d, 2H, J=8 Hz), 7.00 (d, 1H, J=5 Hz), 5.36 (s, 2H), 2.79 (s, 3H), 2.62 (s, 3H)

(46) 2-Ethoxy-5,7-dimethyl-3-[ {2'-(1H-tetrazol-5-yl) biphenyl-4-yl} methyl]-3H-imidazo[4,5-b]pyridine

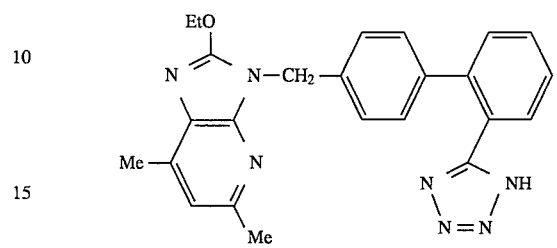

NMR (DMSO—d6) δ: 7.66 (1H, dt, J=1.8 Hz), 7.65 (1H, d, J=8 Hz), 7.56 (1H, dt, J=1.8 Hz), 7.52 (1H, d, J=8 Hz), 7.14 (2H, d, J=8 Hz), 7.04 (2H, d, J=8 Hz), 6.86 (1H, s), 5.18 (2H, s), 4.53 (2H, q, J=7 Hz), 2.45 (3H, s), 2.41 (3H, s), 1.34 (3H, t, J=7 Hz)

(47) 5,7-Dimethyl-2-methoxy-3-[{2'-(1H-tetrazol-5-yl) biphenyl-4-yl}methyl]-3H-imidazo[4,5-b]pyridine

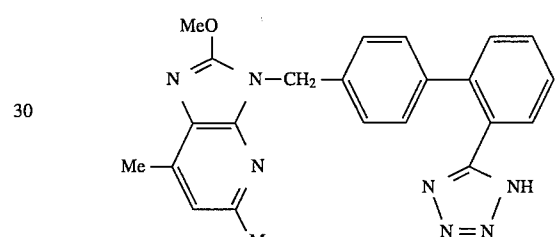

(48) 5,7-Dimethyl-2-n-propoxy-3-[ { 2'-(1H-tetrazol-5-yl) biphenyl-4-yl} methyl]-3H-imidazo[4.5-b]pyridine

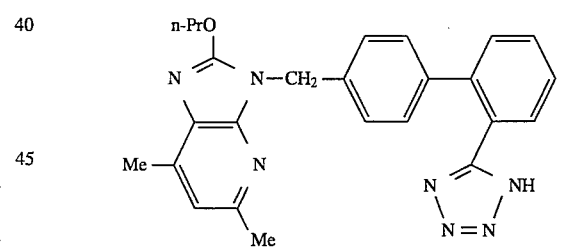

NMR (DMSO—d6) δ: 7.66 (1H, dt, J=1.8 Hz), 7.65 (1H, d, J=8 Hz), 7.56 (1H, dt, J=1.8 Hz), 7.51 (1H, d, J=8 Hz), 7.15 (2H, d, J=8 Hz), 7.05 (2H, d, J=8 Hz), 6.86 (1H, s), 5.18 (2H, s), 4.43 (2H, t, J=7 Hz), 2.46 (3H, s), 2.41 (3H, s), 1.78~1.68 (2H, m), 0.90 (3H, t, J=7 Hz)

EXAMPLE 5

3-{2'-Carboxybiphenyl-4-yl)methyl}-2-cyclopropyl-7-methyl-3H-imidazo[4,5-b]pyridine

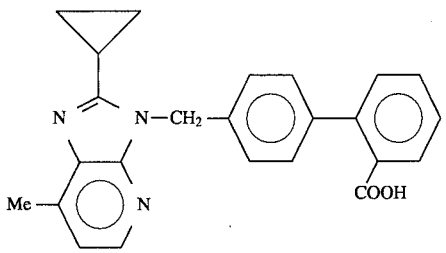

40 ml of ethanol and 20 ml of a 10% aqueous sodium hydroxide solution were added to 1.32 g of 2-cyclopropyl-3-{2'-carboxybiphenyl-4-yl)methyl}-7-methyl-3H-imidazo[4,5-b]pyridine, and the mixture was heated under reflux for 21 hr. The reaction mixture was concentrated to 30 ml, cooled and neutralized with 2N hydrochloric acid and acetic acid, and the precipitated crystal was collected by filtration and recrystallized from water. The yield was 1.03 g.

m.p. (° C.): 221~224

NMR (90 MHz, DMSO—$d_6$, δ value): 8.12 (d, 1H, J=5 Hz), 8.75~8.20 (m, 4H), 7.26 (s, 4H), 7.04 (d, 1H, J=5 Hz), 5.63 (s, 2H), 2.50~2.05 (m, 1H), 1.24~0.90 (m, 4H)

The following compounds were synthesized according to the process described in Example 5. The names, chemical structure formulae and physical constants of the synthesized compounds will be described below.

(1) 2-Butyl-1-{(2'-carboxylphenyl-4-yl)-methyl}benzimidazole

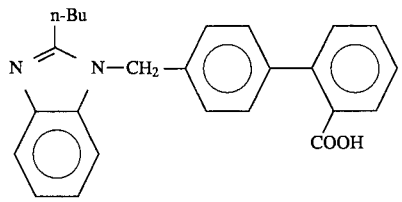

m.p. (° C.): 233~235

NMR (90 MHz, DMSO—$d_6$, δ value): 7.75~8.90 (m, 12H), 5.48 (s, 2H), 2.82 (t, 2H, J=7 Hz) 1.95~1.05 (m, 4H), 0.84 (t, 3H, J=7 Hz)

(2) 3-{(2'-Carboxybiphenyl-4-yl)methyl}-2-ethyl-7-methyl-3H-imidazo[4,5-b]pyridine

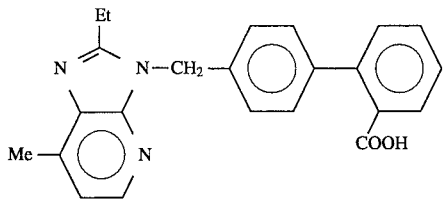

m.p. (° C.): 222~224

NMR (90 MHz, DMSO—$d_6$, δ value): 8.16 (d, 1H, J=5 Hz), 7.75~6.96 (m, 9H), 5.52 (s, 2H), 2.86 (q, 2H, J=7 Hz), 2.57 (s, 3H), 1.27 (t, 3H, J=7 Hz)

(3) 3-{(2'-Carboxybiphenyl-4-yl)methyl}-7-methyl-2-n-propyl-3H-imidazo[4,5-b]pyridine

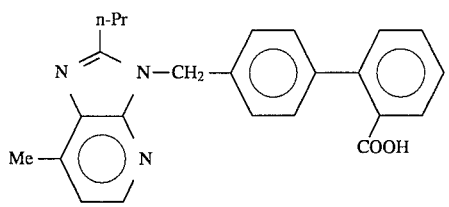

m.p. (° C.): 260~263

NMR (90 MHz, DMSO—$d_6$, δ value): 8.15 (d, 1H, J=5 Hz), 7.75~6.95 (m, 9H), 5.53 (s, 2H), 2.82 (t, 2H, J=7 Hz), 2.56 (s, 3H), 2.00~1.48 (m, 2H), 0.94 (t, 3H, J=7 Hz)

(4) 2-n-Butyl-3-{(2'-carboxybiphenyl-4-yl)-methyl}-7-methyl-3H-imidazo[4,5-b]pyridine

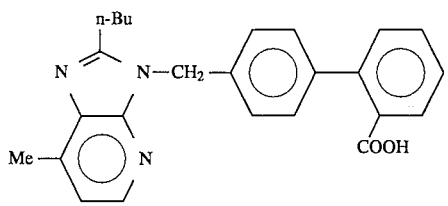

m.p. (° C.): 230~232

NMR (400 MHz, DMSO—$d_6$, δ value): 8.15 (d, 1H, J=5 Hz), 7.68 (d, 1H, J=8 Hz), 7.52 (t, 1H, J=8 Hz), 7.41 (t, 1H, J=8 Hz), 7.30 (d, 1H, J=8 Hz), 7.60 (d, 2H, J=8 Hz), 7.15 (d, 2H, J=8 Hz), 7.07 (d, 1H, J=5 Hz), 5.52 (s, 2H), 2.83 (t, 2H, J=8 Hz), 2.54 (s, 3H), 1.72~1.60 (m, 2H), 1.40~1.28 (m, 2H), 0.84 (t, 3H, J=8 Hz)

(5) 3-{(2'-Carboxybiphenyl-4-yl)methyl}-2-isopropyl-7-methyl-3H-imidazo[4,5-b]pyridine

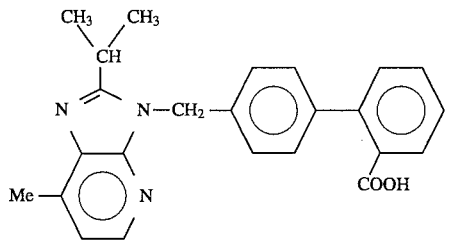

m.p. (° C.): 241~244

NMR (400 MHz, DMSO—$d_6$, δ value): 8.17 (d, 1H, J=5 Hz), 7.70 (d, 1H, J=8 Hz), 7.54 (t, 1H, J=8 Hz), 7.43 (t, 1H, J=8 Hz), 7.33 (d, 1H, J=8 Hz), 7.27 (d, 2H, J=8 Hz), 7.16 (d, 2H, J=8 Hz), 7.10 (d, 1H, J=5 Hz), 5.56 (s,2H), 3.45~3.20 (m, 1H), 2.58 (s, 4H), 1.25 (d, 6H, J=7 Hz)

(6) 3-{(2'-Carboxybiphenyl-4-yl)methyl}-2,7-dimethyl-3H-imidazo[4,5-b]pyridine

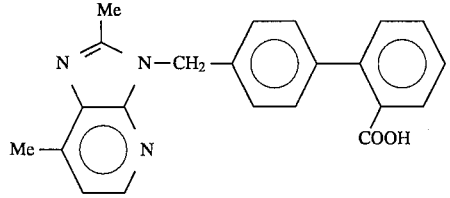

m.p. (° C.): 257~259

NMR (400 MHz, DMSO—$d_6$, δ value): 8.16 (d, 1H, J=5 Hz), 7.70 (d, 1H, J=8 Hz), 7.54 (t, 1H, J=8 Hz), 7.43 (t, 1H, J=8 Hz), 7.33 (d, 1H, J=8 Hz), 7.28 (d, 2H, J=8 Hz), 7.20 (d, 2H, J=8 Hz), 7.08 (d, 1H, J=5 Hz), 5.52 (s, 2H), 2.55 (s, 3H), 2.54 (s, 3H)

(7) 7-Methyl-2-(1-propenyl)-3-[ (2'-carboxybiphenyl- 4-yl)methyl]-3H-imidazo-[ 4,5-b] pyridine

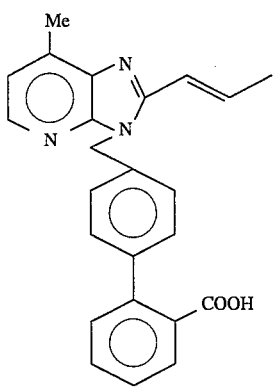

NMR (400 MHz, DMSO—$d_6$, δ value): 8.14 (d, 1H, J=5 Hz), 7.67 (d, 1H, J=8 Hz), 7.51 (td, 1H, J=8 Hz, 1 Hz), 7.40 (td, 1H, J=8 Hz, 1 Hz), 7.29 (d, 1H, J=8 Hz), 7.27~ 7.10 (m, 5H), 7.08 (d, 1H, J=5 Hz), 6.78 (d, 1H, J= 15 Hz), 5.59 (s, 2H), 2.56 (s, 3H), 1.96 (d, 3H, J=8 Hz)

(8) 7-Chloro-2-n-propyl-3-[ (2'-carboxybiphenyl- 4-yl)methyl]-3H-imidazo{ 4,5-b] pyridine

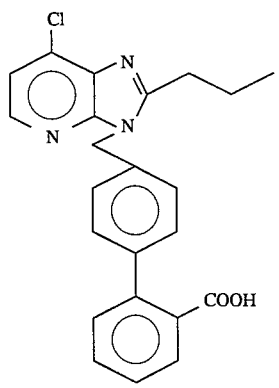

NMR (400 MHz, $CDCl_3$ + DMSO—$d_6$, δ value): 8.19 (d, 1H, J=5 Hz), 7.82 (d, 1H, J=7 Hz), 7.44 (t, 1H, J= 7 Hz), 7.34 (t, 1H, J=7 Hz), 7.29~7.20 (m, 4H), 7.11 (d,2H, J=8 Hz), 5.49 (s, 2H), 2.81 (t, 2H, J=8 Hz), 1.84~1.73 (m,2H), 0.96 (t, 3H, J=8 Hz)

(9) 7-Methyl-2-methylthio-3-[ (2'-carboxybiphenyl- 4-yl)methyl]-3H-imidazo[ 4,5-b] pyridine

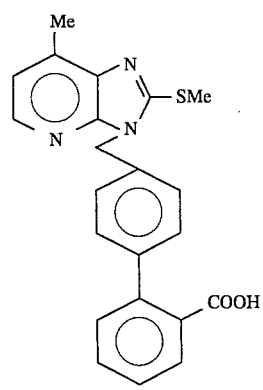

NMR (400 MHz, $CDCl_3$ + DMSO—$d_6$, δ value): 8.13 (d, 1H, J=5 Hz), 7.80 (dd, 1H, J=7 Hz, 1 Hz), 7.47 (td, 1H, J=7 Hz, 1 Hz), 7.39~7.28 (m, 6H), 7.00 (d, 1H, J=5 Hz), 5.41 (s, 2H), 2.79 (s, 3H), 2.64 (s, 3H)

(10) 7-Methoxymethyl-7-methyl-3-[ (2'-carboxybiphenyl-4-yl)methyl]-3H- imidazo-[ 4,5-b] pyridine

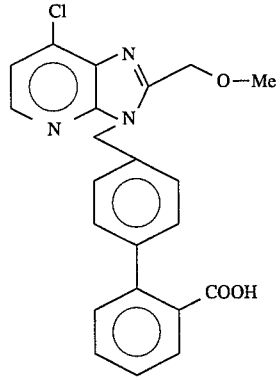

NMR (400 MHz, DMSO—$d_6$, δ value): 8.23 (d, 1H, J=5 Hz), 7.67 (d, 1H, J=8 Hz), 7.51 (td, 1H, J=8 Hz, 1 Hz), 7.40 (td, 1H, J=8 Hz, 1 Hz), 7.30 (d, 1H, J=8 Hz), 7.26~7.13 (m, 4H), 7.13 (d, 1H, J=5 Hz), 5.55 (s, 2H), 4.66 (s, 2H), 2.26 (s, 3H), 2.56 (s, 3H)

(11) 2-Cyclobutyl-7-methyl-3-[ (2'-carboxybiphenyl- 4-yl)methyl]-3H-imidazo[ 4,5-b] pyridine

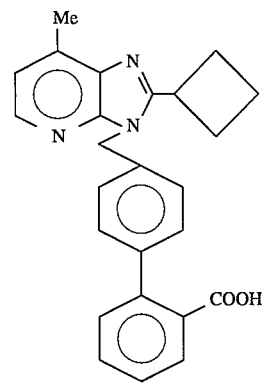

NMR (400 MHz, DMSO—$d_6$, δ value): 8.15 (d, 1H, J=5 Hz), 7.69 (d, 1H, J=8 Hz), 7.52 (td, 1H, J=8 Hz, 1 Hz), 7.42 (td, 1H, J=8 Hz, 1 Hz), 7.31 (d, 1H, J=8 Hz), 7.25 (d, 2H, J=8 Hz), 7.13 (d, 2H, J=8 Hz), 7.08 (d, 1H, J=5 Hz), 5.43 (s, 2H), 3.81 (quint, 1H, J=8 Hz), 2.58 (s, 3H), 2.45~ 2.33 (m, 2H), 2.25~2.16 (m, 2H), 2.06~1.93 (m, 1H), 1.90~1.80 (m, 1H)

(12) 2-Ethylthio-7-methyl-3-[ (2'-carboxybiphenyl- 4-yl)methyl]-3H-imidazo[ 4,5-b]pyridine

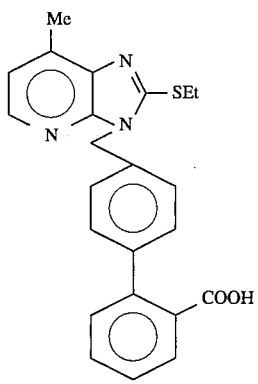

NMR (400 MHz, CDCl₃ + DMSO—d₆, δ value): 8.11 (d, 1H, J=5 Hz), 7.02 (d, 1H, J=8 Hz), 7.51 (td, 1H, J=8 Hz, 1 Hz), 7.41 (td, 1H, J=8 Hz, 1 Hz), 7.34~7.22 (m, 5H), 7.04 (d, 1H, J=5 Hz), 5.41 (s, 2H), 3.39 (q, 2H, J=8 Hz), 2.58 (s, 3H), 1.44 (t, 1H, J=8 Hz)
(13) 3-{(2'-Carboxybiphenyl-4-yl)methyl} -2-ethoxy-7-methyl- 3H-imidazo[4,5-b]pyridine

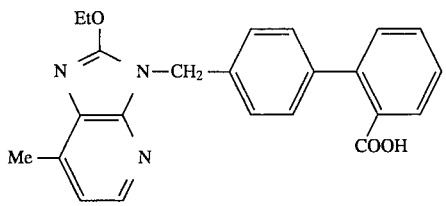

NMR (DMSO—d₆) δ: 8.00 (1H, d, J=5 Hz), 7.59 (1H, dd, J=1.8 Hz), 7.45 (1H, dt, J=1.8 Hz), 7.36 (1H, dt, J=1.8 Hz), 7.30 (1H, d, J=8 Hz), 7.30 (2H, d, J=8 Hz), 7.25 (2H, d, J=8 Hz), 7.00 (1H, d, J=5 Hz), 5.24 (2H, s), 4.60 (2H, q, J=7 Hz), 2.47 (3H, s), 1.41 (3H, t, J=7 Hz)
(14) 3-{(2'-Carboxybiphenyl-4-yl)methyl} -2-methoxy-7-methyl- 3H-imidazo[4,5-b]pyridine

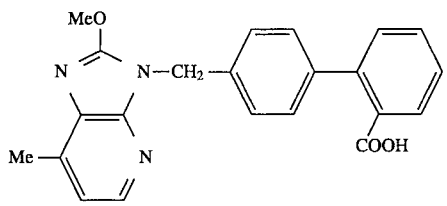

(15)  3-{(2'-Carboxybiphenyl-4-yl)methyl-2-n-propoxy-3H-imidazo[4,5-b]pyridine

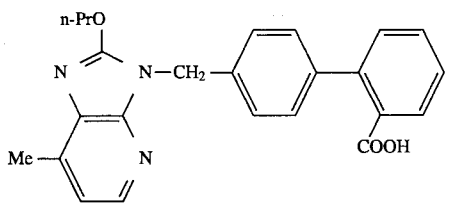

NMR (DMSO—d₆) δ: 8.01 (1H, d, J=5 Hz), 7.64 (1H, d, J=8 Hz), 7.49 (1H, t, J=8 Hz), 7.39 (1H, t, J=8 Hz), 7.30 (1H, d, J=8 Hz), 7.28 (4H, s), 7.00 (1H, d, J=5 Hz), 5.25 (2H, s), 4.50 (2H, t, J=7 Hz), 2.47 (3H, s), 1.83~1.78 (2H, m), 0.96 (3H, t, J=7 Hz)
(16) 3-{(2'-Carboxybiphenyl-4-yl)methyl}-5,7-dimethyl-2-ethoxy-3H-imidazo[4,5-b]pyridine

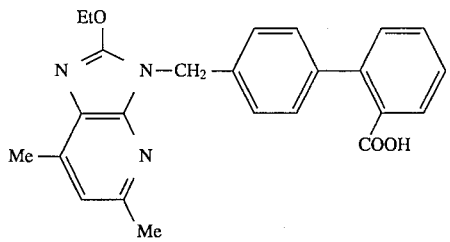

NMR (CDCl₃) δ: 7.70 (1H, d, J=8 Hz), 7.54 (1H, t, J=8 Hz), 7.43 (1H, t, J=8 Hz), 7.33 (1H, d, J=8 Hz), 7.29 (2H, d, J=8 Hz), 7.24 (2H, d, J=8 Hz), 6.87 (1H, s), 5.25 (2H, s), 4.56 (2H, q, J=7 Hz), 2.46 (3H, s), 2.42 (3H, s), 1.38 (3H, t, J=7 Hz)
(17)  3-{(2'-Carboxybiphenyl-4-yl)methyl}-5,7-dimethyl-2-methoxy-3H-imidazo[4,5-b]pyridine

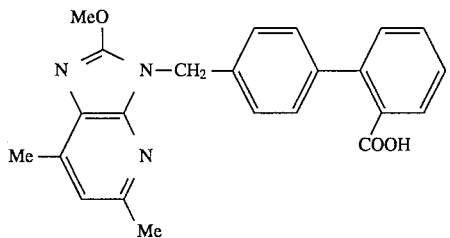

NMR (DMSO—d₆) δ: 7.70 (1H, d, J=8 Hz), 7.55 (1H, t, J=8 Hz), 7.44 (1H, t, J=8 Hz), 7.35 (1H, d, J=8 Hz), 7.29 (2H, d, J=8 Hz), 7.15 (2H, d, J=8 Hz), 6.68 (1H, s), 5.28 (2H, s), 3.39 (3H, s), 2.40 (3H, s), 2.23 (3H, s)
(18)  3-{(2'-Carboxybiphenyl-4-yl)methyl}-5,7-dimethyl-2-n-propoxy-3H-imidazo[ 4,5-b]pyridine

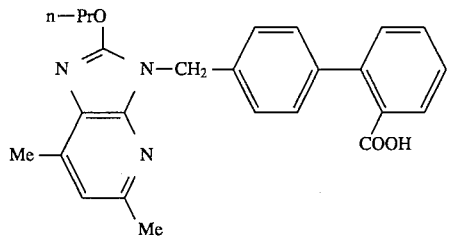

NMR (DMSO—d₆) δ: 7.51 (1H, dd, J=1.8 Hz), 7.38 (1H, dt, J=1.8 Hz), 7.32 (2H, t, J=8 Hz), 7.31 (1H, dt, J=1.8 Hz), 7.24 (1H, dd, J=1.8 Hz), 7.21 (2H, d, J=8 Hz), 6.86 (1H, s), 5.21 (2H, s), 4.46 (2H, t, J=7 Hz), 2.47 (3H, s), 2.42 (3H, s), 1.83~1.73 (2H, m), 0.94 (3H, t, J=7 Hz)

EXAMPLE 6

2-Ethylsulfonyl-7-methyl-3[ (2'-(1H-tetrazol-5-yl)biphenyl- 4-yl) methyl]-3H-imidazo[4.5-b]pyridine 6.4 g (15 mmol) of 2-ethylthio-7-methyl-3[ (2'-(1H-tetrazol- 5-yl) biphenyl -4-yl) methyl]-3H- imidazo[4.5-b] pyridine was dispersed in 150 ml of dichloromethane. 150 ml of a dichloromethane solution of 3.94 g (23 mmol) of meta-chloro-perbenzoic acid was added dropwise to the solution over 40 minutes, while agitated and cooled with water and ice. The mixture was stirred at room temperature for 20 minutes. The reaction product mixture was washed separately with 10% aqueous solution of sodium bisulfate, a saturated aqueous solution of sodiuim bicarbonate and a saturated saline. The dichloromethane phase was separated and taken, then dried with aqueous magnesium sulfate. The solvent was distilled out at a reduced pressure and the residue was treated chromatographically with silicagel to obtain 5.93 g of the above named compound from the eluate of ethyl acetate and methanol (9:1 v/v).

EXAMPLE 7

2-Methoxy-7-methyl-3[ (2'-(1H-tetrazol-5-yl)biphenyl-4-yl)methyl]-3H-imidazo[4.5-b]pyridine 420 mg (2.2 mmol) of 28% methanol solution of sodium methoxide was added to 10 ml of a methanol solution of 0.44 g (0.96 mmol) of 2-ethylsulfonyl-7-methyl- 3[(2'-(1H-tetrazol-5-yl)biphenyl-4-yl)methyl]- 3H-imidazo[4.5-b]-pyridine was dispersed in 150 ml of dichloromethane. The mixture was refluxed for 40 minutes. The solvent was distilled out at a reduced pressure. The residue was mixed with water and neutralized with 2N HCl. An extract with dichloromethane was washed with a saturated saline and dried with anhydrous magnesium sulfate. The solvent was distilled out at a reduced pressure. The residue was treated with ethanol and ether for recrystallization to obtain 300 mg of the above named compound.

EXAMPLE 7-1

2-Ethoxy-7-methyl-3[ (2'-(1H-tetrazol-5-yl)biphenyl-4-yl)methyl]-3H-imidazo[4,5-b]pyridine was obtained in the same manner as shown in Example 7.

EXAMPLE 8

2-n-butoxy-7-methyl-3[ (2'-(1H-tetrazol-5-yl)-biphenyl-4-yl) methyl]-3H-imidazo[4.5-b] pyridine A mixture of 100 mg (1.3 mmol) of n-butanol, 400 mg (3.6 mmol) of potassium tert.-butoxide and DMF was heated at 80 degree C. for 5 minutes. 300 mg (0.65 mmol) of 2-ethyl-sulfonyl-7-methyl-3[ (2'-(1H-tetrazol-5-yl)-biphenyl- 4-yl)methyl]-3H-imidazo[4.5-b]pyridine was added to the mixture. The resultant was heated for 2 hours. The reaction product mixture was mixed with water, neutralized with 2n HCl and extracted with dichloromethane. The dichloromethane phase was washed with a saturated saline and dried with anhydrous magnesium sulfate. The solvent was distilled out at a reduced pressure and the residue was treated with ether-hexane-dichloromethane or re-crystallization to obtained 140 mg of the intended compound.

The following compounds were produced by the same production process as shown above:

7-methyl-2-n-propoxy-3[ (2'-(1H-tetrazol-5-yl)-biphenyl-4-yl)methyl]-3H-imidazo[4.5-b] pyridine 2-isopropoxy-7-methyl-3[ (2'-(1H-tetrazol-5-yl)-biphenyl- 4-yl)methyl]-3H-imidazo[4.5-b] pyridine 2-cyclopropylmethoxy-7-methyl-3[ (2'-(1H-tetrazol-5-yl)-biphenyl-4-yl)methyl]-3 H-imidazo[4.5-b] pyridine

EXAMPLE 9

7-methyl-3[ (2'-(1H-tetrazol-5-yl)-biphenyl-4-yl)-methyl] -1,3-dihydro-2-oxo-imidazo[4.5-b] pyridine A mixture of 90 mg (0.23 mmol) of 2-methoxy-7-methyl-3[ (2'-(1H-tetrazol-5-yl)-biphenyl-4-yl)methyl] -3H-imidazo[4.5-b]pyridine and 1 ml of 48% HBr was stirred at a room temperature for 1.5 hours. The product mixture was mixed with water to produce crystals, which was taken out and washed with water to obtain 70 mg of the intended compound.

EXAMPLE 10

2-hydroxymethyl-7-methyl-3[ (2'-(1H-tetrazol-5-yl)-biphenyl- 4-yl)-methyl]-3H-imidazo[4.5-b] pyridine 30 ml of a dichloromethane solution of 410 mg (1 mmol) of 2-methoxy-methyl-7-methyl-3[ (2'-(1H-tetrazol- 5-yl)-biphenyl-4-yl)-methyl]-3H-imidazo[4.5-b] pyridine was stirred, cooled with ice. During this step, 10 ml (10 mmol) of dichloromethane solution of 1M boron tribromide was added little by little thereto dropwise. The mixture was further agitated at a room temperature for 12 hours. The reaction product mixture was cooled, while stirred. During this step, methanol was added little by little. The solvent was distilled out at a reduced pressure. The residue was mixed with water, neutralized with sodium bicarbonate, adjusted to a weak acidity with acetic acid and decanted to remove the water. The residue was mixed with methanol. The solvent was distilled out at a reduced pressure. The residue was treated with isopropylether for re-crystallization to obtain 330 mg of the intended compound.

EXAMPLE 11

2-chloroymethyl-7-methyl-3[ (2'-(1H-tetrazol-5-yl)-biphenyl- 4-yl)-methyl]-3H-imidazo[ 4.5-b] pyridine A mixture of 20 ml of dichloromethane and 2.2 g (5.5 mmol) of 2-hydroxymethyl-7-methyl-3[ (2'-(1H-tetrazol-5-yl)-biphenyl-4-yl)-methyl]-3H-imidazo[4.5-b]pyridine was stirred, cooled with ice. During this step, 1.6 ml of thionyl chloride was added thereto. The mixture was further agitated at a room temperature for 1 hour. The solvent was distilled out at a reduced pressure. The residue was mixed with water, neutralized with sodium bicarbonate, adjusted to a weak acidity with acetic acid and extracted with dichloromethane. The dichloromethane phase was washed with a saturated saline and dried with anhydrous magnesium sulfate. The solvent was distilled out at a reduced pressure. The residue was treated with dichloromethane for re-crystallization to obtain 1.37 mg of the intended compound.

EXAMPLE 12

3-[ (2'-carboxybiphenyl-4-yl)methyl]-2-hydroxy-methyl-7-methyl-3H-imidazo[4.5-b] pyridine A mixture of 8 ml of an aqueous 10% sodium hydroxide solution of 500 mg (1.3 mmol) of 2-hydroxymethyl-3-[ (2'-methoxycarbonyl-biphenyl-4-yl)methyl]-7-methyl-3H-imidazo[4.5-b]pyridine and 20 ml of ethanol was heated for reflux for 2 hours. The insoluble was removed out and the filtrate was concentrated. The residue was mixed with water and washed with ethyl acetate. The aqueous phase was weakly acidified with 2N hydrochloric acid and acetic acid. The precipitates of crystals was taken out and washed with water, dried, to obtain 400 mg of the intended compound.

EXAMPLE 13

According to one of the foregoing Examples and Preparation Examples, the following compounds were obtained.

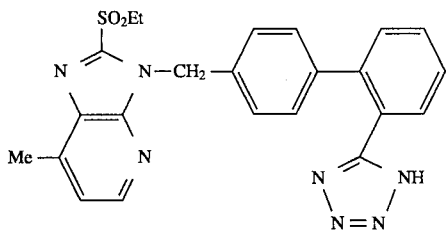

NMR (400 MHz, DMSO—d₆, δ value): 8.50 (1H, d, J=5 Hz), 7.64~7.51 (4H, m), 7.48 (1H, dd, J=1 Hz, 5 Hz), 7.17 (2H, d, J=8 Hz), 7.04 (2H, d, J=8 Hz), 5.82 (2H, s), 3.52 (2H, q, J=7 Hz), 2.66 (3H, s), 1.22 (3H, t, J=7 Hz)

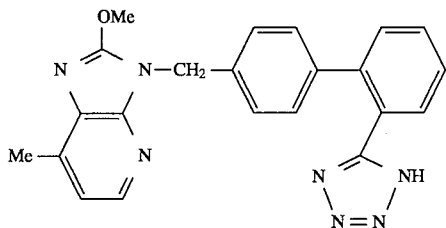

NMR (400 MHz, DMSO—d₆, δ value): 8.0 (1H, d, J=5 Hz), 7.64 (2H, d, J=8 Hz), 7.56 (1H, td, J=8 Hz, 1 Hz), 7.51 (1H, d, J=8 Hz), 7.16 (2H, d, J=8 Hz), 7.04 (2H, d, J=8 Hz), 7.01 (1H, d, J=5 Hz), 5.23 (2H, s), 4.14 (3H, s), 2.48 (3H, s)

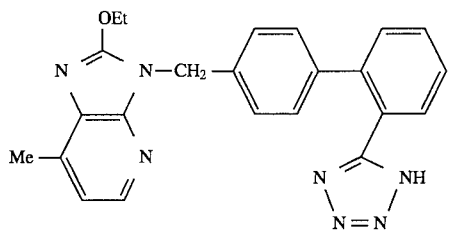

NMR (400 MHz, DMSO—d₆, δ value): 7.99 (1H, d, J=5 Hz), 7.65 (2H, d, J=8 Hz), 7.56 (1H, t, J=8 Hz), 7.51 (1H, d, J=8 Hz), 7.18 (2H, d, J=8 Hz), 7.04 (2H, d, J=8 Hz), 7.00 (1H, d, J=5 Hz), 5.21 (2H, 4.57 (2H, q, J=7 Hz), 2.46 (3H, s), 1.37 (3H, t, J=7 Hz)

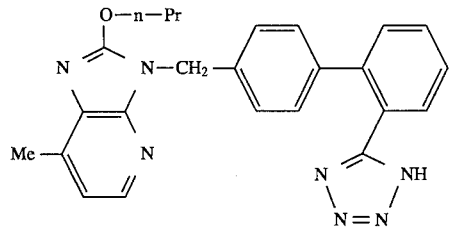

NMR (400 MHz, DMSO—d₆, δ value): 8.00 (1H, d, J=5 Hz), 7.65 (2H, dd, J=8 Hz, 1 Hz), 7.57 (1H, td, J=8 Hz, 1 Hz), 7.51 (1H, d, J=8 Hz), 7.20 (2H, d, J=8 Hz,), 7.05 (2H, d, J=8 Hz), 7.00 (1H, d, J=5 Hz), 5.24 (2H, s), 4.48 (2H, t, J=7 Hz), 2.47 (3H, s), 1.81~1.73 (2H, m), 0.93 (3H, t, J=7 Hz)

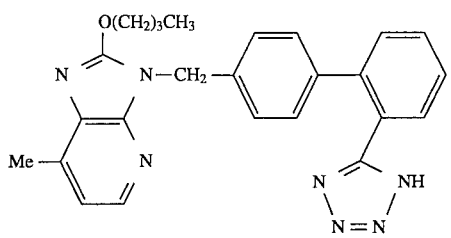

NMR (400 MHz, DMSO—d₆, δ value): 8.00 (1H, d, J=5 Hz), 7.65 (2H, dd, J=8 Hz, 1 Hz), 7.56 (1H, td, J=8 Hz, 1 Hz), 7.18 (2H, d, J=8 Hz), 7.04 (2H, d, J=8 Hz), 7.00 (1H, d, J=5 Hz), 5.21 (2H, s), 4.52 (2H; t, J=7 Hz), 2.47 (3H, s), 1.77~1.70 (2H, m), 1.41~1.32 (2H, m), 0.90 (3H, t, J=7 Hz)

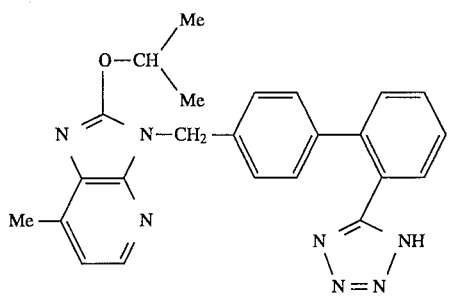

NMR (400 MHz, DMSO—d₆, δ value): 7.98 (1H, d, J=5 Hz), 7.64 (2H, d, J=8 Hz), 7.56 (1H, t, J=8 Hz), 7.51 (1H, d, J=8 Hz), 7.18 (2H, d, J=8 Hz), 7.04 (2H, d, J=8 Hz), 6.99 (1H, d, J=5 Hz), 5.35~5.30 (1H, m), 5.18 (2H, s), 2.47 (3H, s), 1.36 (6H, d, J=6 Hz)

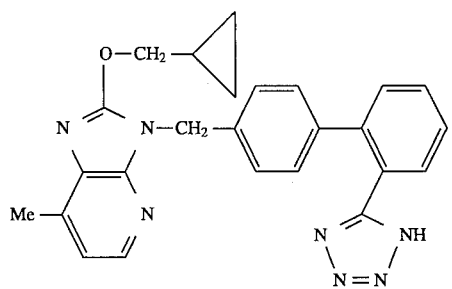

NMR (400 MHz, DMSO—d₆, δ value): 7.99 (1H, d, J=5 Hz), 7.64 (2H, d, J=8 Hz), 7.55 (1H, t, J=8 Hz), 7.50 (1H, d, J=8 Hz), 7.21 (2H, d, J=7 Hz), 7.05 J=6 Hz) (2H, d, J=7 Hz), 6.99 (1H, d, J=5 Hz), 5.23 (2H, s), 4.38 (2H, d, J=8 Hz), 2.46 (3H, s), 1.36~1.25 (1H, 0.63~ 0.50 (2H, m), 0.41~0.35 (2H, m)

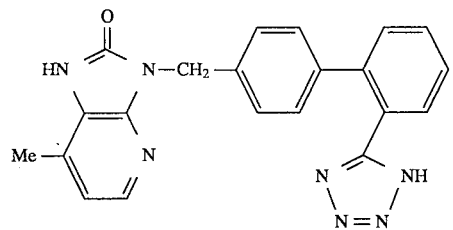

NMR (400 MHz, DMSO—d₆. δ value): 11.36 (1H, s), 7.83 (1H, d, J=5 Hz), 7.66 (1H, dd, J=8 Hz, 1 Hz), 7.65 (1H, d, J=8 Hz), 7.56 (1H, td, J=8 Hz, 1 Hz), 7.52 (1H, d, J=8 Hz), 7.23 (2H, d, 3.81 Hz), 7.04 (2H, d, J=8 Hz), 6.89 (1H, d, J=5

Hz), 5.00 (2H, s), 2.31 (3H, s)

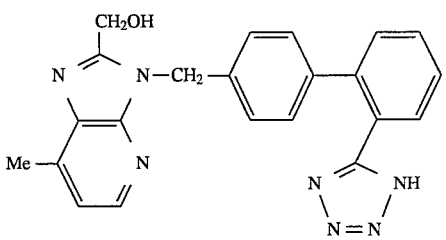

NMR (400 MHz, DMSO—d$_6$, δ value): 8.19 (1H, d, J=5 Hz), 7.61 (2H, t, J=8 Hz), 7.52 (1H, t, J=8 Hz), 7.47 (1H, d, J=8 Hz), 7.14 (2H, d, J=8 Hz), 7.11 (1H, d, J=5 Hz), 7.03 (2H, d, J=8 Hz), 5.56 (2H, s), 4.67 (2H, s), 2.55 (3H, s)

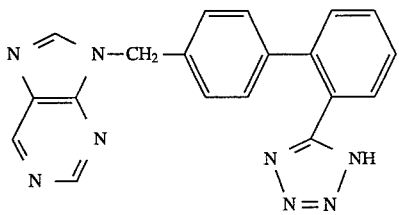

NMR (400 MHz, DMSO—d$_6$, δ value): 9.15 (1H, s), 8.92 (1H, s), 8.72 (1H, s), 7.61 (2H, d, J=7 Hz), 7.53 (1H, d, J=7 Hz), 7.46 (1H, d, J=7 Hz), 7.24 (2H, d, J=7 Hz), 7.03 (2H, d, J=7 Hz), 5.48 (2H, s)

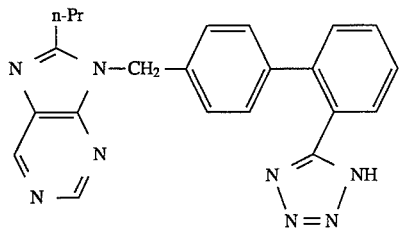

NMR (400 MHz, DMSO—d$_6$, δ value): 9.07 (1H, s), 8.90 (1H, s), 7.66 (2H, d, J=8 Hz), 7.57 (1H, t, J=8 Hz), 7.52 (1H, d, J=8 Hz), 7.14 (2H, d, J=8 Hz), 7.07 (2H, d, J=8 Hz), 5.52 (2H, s), 2.84 (2H, t, J=8 Hz), 1.78~1.69 (2H, m), 0.93 (3H, t, J=8 Hz)

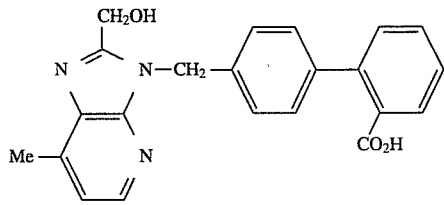

NMR (400 MHz, DMSO—d$_6$, δ value): 8.18 (1H, d, J=5 Hz), 7.66 (1H, dd, J=8 Hz, 1 Hz), 7.51 (1H, td, J=8 Hz, 1 Hz), 7.40 (1H, td, J=8 Hz, 1 Hz), 7.30 (1H, dd, J=8 Hz, 1 Hz), 7.23 (4H, s), 7.09 (1H, d, J=5 Hz), 5.57 (2H, s), 4.70 (2H, s), 2.54 (3H, s)

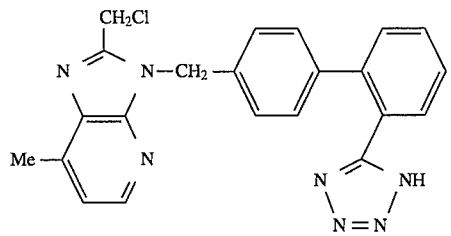

NMR (400 MHz, DMSO—d$_6$, δ value): 8.27 (1H, d, J=5 Hz), 7.68~7.64 (2H, m), 7.56 (1H, t, J=8 Hz), 7.51 (1H, d, J=8 Hz), 7.18 (1H, d, J=5 Hz), 7.18 (2H, d, J=8 Hz), 7.04 (2H, d, J=8 Hz), 5.60 (2H, s), 5.05 (2H, s), 2.60 (3H, s)

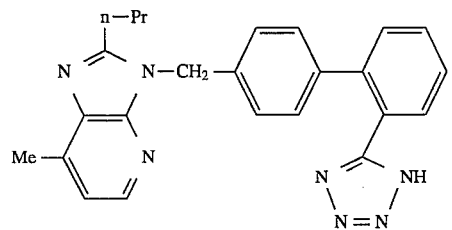

NMR (400 MHz, DMSO—d$_6$, δ value): 7.63 (1H, td, J=8 Hz, 1 Hz), 7.61 (1H, rid, J=8 Hz, 1 Hz), 7.54 (1H, td, J=8 Hz, 1Hz), 7.48 (1H, rid, J=8 Hz, 1 Hz), 7.01 (4H, s), 6.91 (1H, s), 5.43 (2H, s), 2.68 (2H, t, J=8 Hz), 2.47 (6H, s), 1.68~1.59 (2H, m), 0. 87 (3H, t, J=8 Hz)

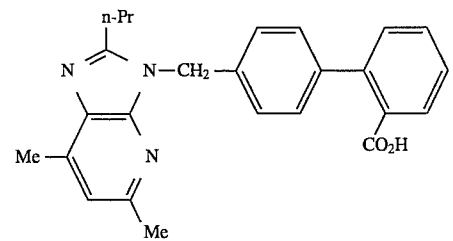

NMR (400 MHz, DMSO—d$_6$, δ value): 7.60 (1H, d, J=8 Hz), 7.45 (1H, t, J=8 Hz), 7.37 (1H, t, J=8 Hz), 7.27 (1H, d, J=8 Hz), 7.26 (2H, d, J=8 Hz), 7.08 (2H, d, J=8 Hz), 6.92 (1H, ), 5.46 (2H, s), 2.73 (2H, t, J=8 Hz), 2.49 (6H, s), 1.74~1.65 (2H, m), 0.89 (3H, t, J=8 Hz)

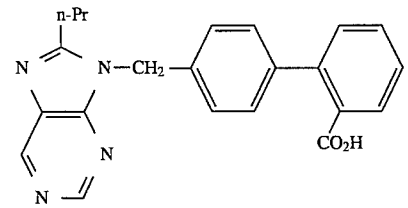

NMR (400 MHz, DMSO—d$_6$, δ value): 9.08 (1H, s), 8.91 (1H, s), 7.71 (1H, d, J=8 Hz), 7.55 (1H, t, J=8 Hz), 7.44 (1H, t, J=8 Hz), 7.34 (1H, d, J=8 Hz), 7.30 (2H, d, J=8 Hz), 7.23 (2H, d, J=8 Hz), 5.54 (2H, s), 2.89 (2H, t, J=8 Hz), 1.81~1.75 (2H, m), 0.95 (3H, t, J=8 Hz)

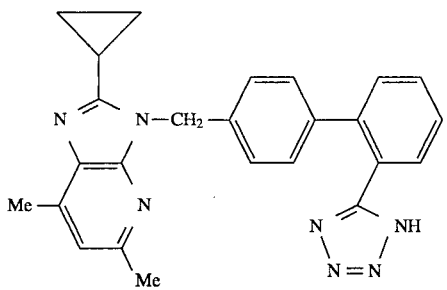

NMR (400 MHz, DMSO—d$_6$, δ value): 7.67 (1H, td, J=8 Hz, 1 Hz), 7.65 (1H, d, J=8 Hz), 7.57 (1H, td, J=8 Hz, 1 Hz), 7.52 (1H, d, J=8 Hz), 7.12 (2H, d, J=8 Hz), 7.05 (2H, d, J=8 Hz), 6.92 (1H, s), 5.54 (2H, s), 2.49 (3H, s), 2.44 (3H, s), 2.17~2.11 (1H, m), 0.99~0.95 (4H, m)

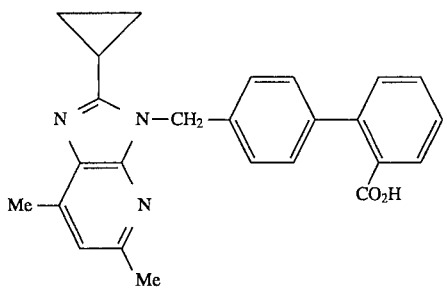

NMR (400 MHz, DMSO—d$_6$, δ value): 7.71 (1H, dd, J=8 Hz, 1 Hz), 7.55 (1H, td, J=8 Hz, 1Hz), 7.44 (1H, td, J=8 Hz, 1 Hz), 7.34 (1H, dd, J=8 Hz, 1 Hz), 7.29 (2H, d, J=8 Hz), 7.23 (2H, d, 6.95 (1H, s), 5.60 (2H, s), 2.49 (3H, s), 2.45 (3H, s), 2.25~2.18 (1H, m), 1.05~1.00 (4H, m)

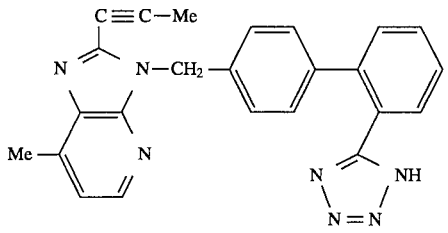

NMR (400 MHz, DMSO—d$_6$, δ value): 8.12 (d. 1H, J=5 Hz), 7.66~ 7.60 (m. 2H), 7.54 (td, 1H, J=8 Hz, 1Hz), 7.49 (dd, 1H, J=8 Hz, 1 Hz), 7.08 ((d, 2H, J=8 Hz), 7.05 (d, 1H, J=5 Hz), 7.02 (d, 2H, J=8 Hz), 5.45 (s, 2H), 2.52 (s, 3H), 2.48 (s, 3H)

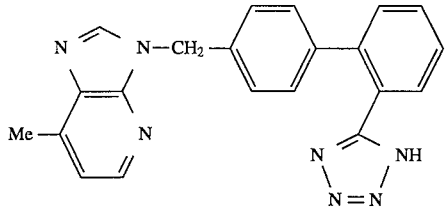

NMR (400 MHz, DMSO—d$_6$, δ value): 8.54 (s, 1H), 8.23 (d, 1H, J=5 Hz), 7.68~ 7.62 (m, 2H), 7.56 (td, 1H, J=8 Hz, 1 Hz), 7.49 (d, 1H, J=8 Hz), 7.24 (2H, d, J=8 Hz), 7.12 (d, 1H, J=5 Hz), 7.05 (d, 2H, J=8 Hz), 5.49 (s, 2H), 2.58 (s, 3H)

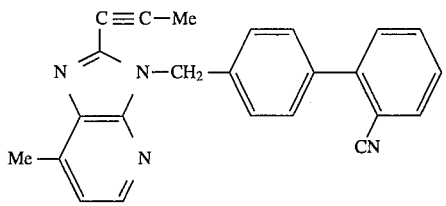

NMR (400 MHz, CDCl$_3$, δ value): 8.22 (d, 1H, J=5 Hz), 7.74 (d, 1H, J=8 Hz), 7.62 (td, 1H, J=8 Hz, 1 Hz), 7.51~7.40 (m, 4H), 7.27 (d, 2H, J=8 Hz), 7.05 (d, 1H, J=5 Hz), 5.54 (s, 2H), 2.69 (s, 3H), 2.60 (s, 3H)

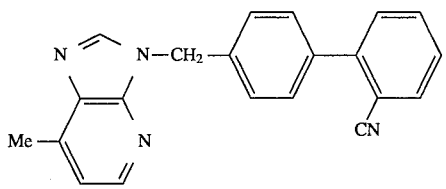

NMR (400 MHz, CDCl$_3$, δ value): 8.32 (d, 1H, J=5 Hz), 8.24~8.17 (bs, 1H), 7.40 (d, 1H, J=8 Hz), 7.63 (td, 1H, J=8 Hz, 1 Hz), 7.52 (d, 2H, J=8 Hz), 7.48~7.39 (m, 4H), 7.11 (d, 1H, J=5 Hz), 5.59 (s, 2H), 2.72 (s, 3H)

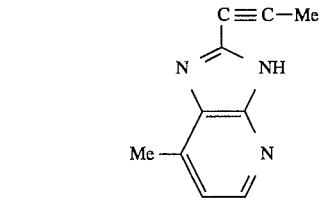

NMR (400 MHz, CDCl$_3$, δ value): 8.16 (d, 1H, J=5 Hz), 7.02 (d, 1H, J=5 Hz), 2.73 (s, 3H), 2.68 (s, 3H)

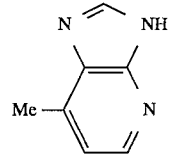

NMR (400 MHz, CDCl$_3$, δ value): 8.30 (d, 1H, J=5 Hz), 8.28 (s, 1H), 7.09 (d, 1H, J=5 Hz), 2.70 (s, 3H)

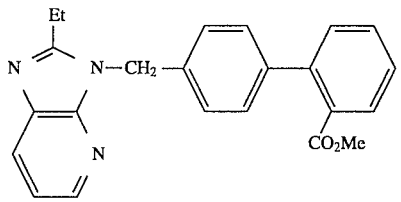

NMR (400 MHz, CDCl$_3$, δ value): 8.36 (dd, 1H, J=1 Hz, 5 Hz), 8.03 (dd, 1H, J=1 Hz, 8 Hz), 7.81 (dd, 1H, J=1 Hz, 8 Hz), 7.51 (td, 1H, J=8 Hz, 1 Hz), 7.40 (td, 1H, J=8 Hz, 1 Hz), 7.31 (dd, 1H, J=1 Hz, 8 Hz), 7.24 (d, 2H, J=8 Hz), 7.23 (dd, 1H, J=5 Hz, 8 Hz), 7.18 (d, 2H, J=8 Hz), 5.54 (s, 2H), 3.61 (s, 3H), 2.87 (q, J=8 Hz), 1.41 (t, 3H, J=8 Hz)

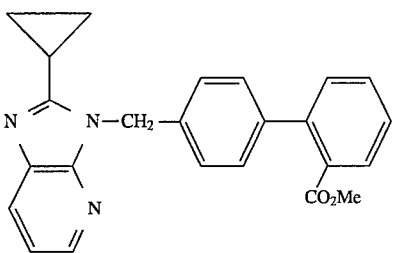

NMR (400 MHz, CDCl₃, δ value: 8.33 (dd, 1H, J=1 Hz, 5 Hz), 7.95 (dd, 1H, J=1 Hz, 8 Hz), 7.82 (dd, 1H, J=1 Hz, 8 Hz), 7.52 (td, 1H, J=8 Hz, 1 Hz), 7.41 (td, 1H, J=8 Hz, 1 Hz), 7.33 (dd, 1H, J=1 Hz, 8 Hz), 7.27 (s, 4H), 7.21 (dd, 1H, J=5 Hz, 8 Hz), 5.67 (s, 2H), 3.63 (s, 3H), 2.06~1.96 (m, 1H), 1.28~1.21 (m, 2H), 1.11~1.04 (m, 2H)

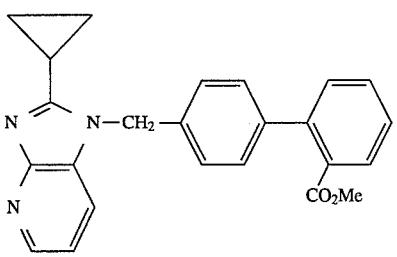

NMR (400 MHz, CDCl₃, δ value): 8.46 (dd, 1H, J=1 Hz, 5 Hz), 7.84 (dd, 1H, J=1 Hz, 8 Hz), 7.55~7.49 (m, 2H), 7.41 (td, 1H, J=8 Hz, 1 Hz), 7.31 (dd, 1H, J=1 Hz, 8 Hz), 7.28 (d, 2H, J=8 Hz), 7.15 (d, 2H, J=8 Hz), 7.09 (dd, 1H, J=5 Hz, 8 Hz), 5.51 (s, 2H), 3.64 (s, 3H), 2.07~1.95 (m, 2H), 1.43~1.35 (m, 2H), 1.16~1.08 (m, 2H),

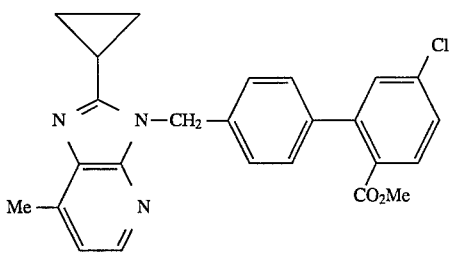

NMR (400 MHz, CDCl₃, δ value): 8.19 (d, 1H, J=5 Hz), 7.70 (d, 1H, J=5 Hz), 7.37 (dd, 1H, J=2 Hz, 8 Hz), 7.31 (d, 1H, J=2 Hz), 7.25~7.20 (m, 4H), 7.01 (d, 1H, J=5 Hz), 5.63 (s, 2H), 3.61 (s, 3H), 2.65 (s, 3H), 2.00~1.92 (m, 1H), 1.24~1.17 (m, 2H), 1.08~1.00 (m, 2H)

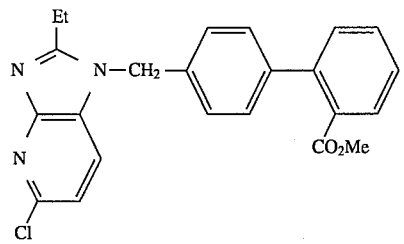

NMR (400 MHz, CDCl₃, δ value): 7.95 (d, 1H, J=8 Hz), 7.82 (dd, 1H, J=1 Hz, 8 Hz), 7.51 (td, 1H, J=8 Hz, 1 Hz), 7.40 (td, 1H, J=8 Hz, 1 Hz), 7.31 (dd, 1H, J=1 Hz, 8 Hz), 7.25 (d, 2H, J=8 Hz), 7.23 (d, 1H, J=5 Hz), 7.17 (d, 2H, J=5 Hz), 5.49 (s, 2H), 3.62 (s, 3H), 2.83 (q, 2H, J=8 Hz), 1.39 (t, 3H, J=8 Hz)

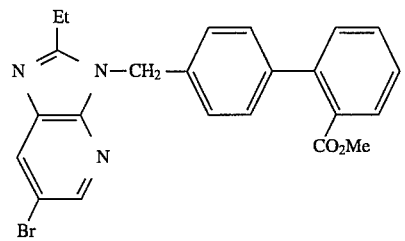

NMR (400 MHz, CDCl₃, δ value): 7.86 (d, 1H, J=8 Hz), 7.53 (td, 1H, J=8 Hz, 1 Hz), 7.46 (d, 1H, J=8 Hz), 7.42 (td, 1H, J=8 Hz, 1 Hz), 7.32 (d, 1H, J=8 Hz), 7.27 (d, 2H, J=8 Hz), 7.14 (d, 1H, J=8 Hz), 7.06 (d, 2H, J=8 Hz), 5.38 (s, 2H), 3.65 (s, 3H), 2.93 (q, 2H, J=8 Hz), 1.46 (t, 3H, J=8 Hz)

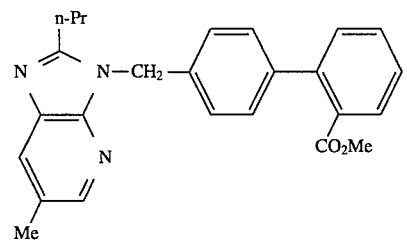

NMR (400 MHz, CDCl₃, δ value): 8.40 (d, 1H, J=2Hz), 8.14 (d, 1H, J=2Hz), 7.83 (dd, 1H, J=1 Hz, 8 Hz), 7.51 (td, 1H, J=8 Hz, 1 Hz), 7.40 (td, 1H, J=8 Hz, 1 Hz), 7.30 (dd, 1H, J=1 Hz, 8 Hz), 7.25 (d, 2H, J=8 Hz), 7.17 (d, 2H, J=8 Hz), 5.50 (s, 2H), 3.62 (s, 3H), 2.87 (q, 2H, J=8 Hz), 1.40 (t, 3H, J=8 Hz)

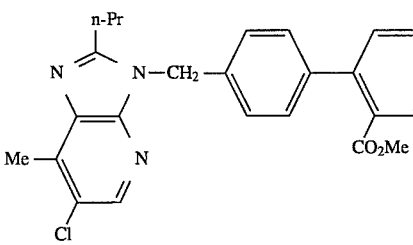

NMR (400 MHz, CDCl₃, δ value): 8.18 (d, 1H, J=2 Hz), 7.82~7.19 (m, 2H), 7.51 (td, 1H, J=8 Hz, 1 Hz), 7.40 (td, 1H, J=8 Hz, 1 Hz), 7.30 (dd, 1H, J=1 Hz, 8 Hz), 7.23 (d, 2H, J=8 Hz), 7.15 (d, 2H, J=8 Hz), 5.51 (s, 2H), 3.61 (s, 3H), 2.80 (t, 2H, J=8 Hz), 2.48 (s, 3H), 1.90~1.78 (m, 2H), 1.00 (t, 3H, J=8 Hz)

NMR (400 MHz, CDCl₃, δ value): 8.28 (s, 1H), 7.82 (dd, 1H, J=1 Hz, 8 Hz), 7.51 (td, 1H, J=8 Hz, 1 Hz), 7.41 (td, 1H, J=8 Hz, 1Hz), 7.31 (dd, 1H, J=1 Hz, 8 Hz), 7.25 (d, 2H, J=8 Hz), 7.15 (d, 2H, J=8 Hz), 5.50 (s, 2H), 3.62 (s, 3H), 2.83 (t, 2H, J=8 Hz), 2.72 (s, 3H), 1.87~1.75 (m, 2H), 1.01 (t, 3H, J=8 Hz)

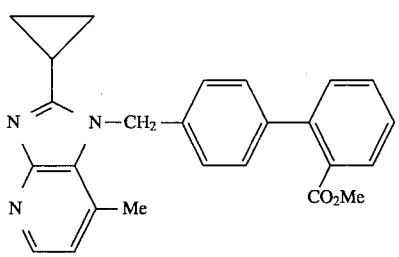

NMR (400 MHz, CDCl₃, δ value): 8.30 (d, 1H, J=5 Hz), 7.83 (dd, 1H, J=1 Hz, 8 Hz), 7.52 (td, 1H, J=8 Hz, 1 Hz), 7.41 (td, 1H, J=8 Hz, 1Hz), 7.32 (dd, 1H, J=1 Hz, 8 Hz), 7.27 (d, 2H, J=8 Hz), 7.02 (d, 2H, J=8 Hz), 6.83 (d, 1H, J=5 Hz), 5.71 (s, 2H), 3.63 (s, 3H), 2.48 (s, 3H), 1.98~1.89 (m, 1H), 1.39~1.32 (m, 2H), 1.11~1.03 (m, 2H)

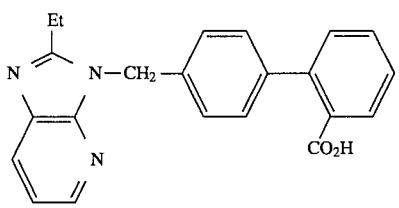

m.p.: 235°~238° C.

NMR (400 MHz, DMSO—d₆, δ value): 8.32 (dd, 1H, J=1 Hz, 5 Hz), 8.20 (dd, 1H, J=1 Hz, 8 Hz), 7.70 (dd, 1H, J=1Hz, 8 Hz), 754 (td, 1H, J=8 Hz, 1 Hz), 7.44 (td, 1H, J=8 Hz, 1 Hz), 7.34 (dd, 1H, J=1 Hz, 8 Hz), 7.30~7.24 (m, 3H), 7.20 (d, 2H), 5.56 (s, 2H), 2.89 (q, 2H, J=8 Hz), 1.29 (t, 3H, J=8 Hz)

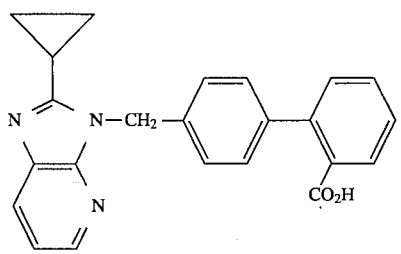

m.p.: 246.5°~248.5° C.

NMR (400 MHz, DMSO—d₆, δ value): 8.27 (dd, 1H, J=1 Hz, 5 Hz), 7.92 (dd, 1H, J=1 Hz, 8 Hz), 7.71 (dd, 1H, J=1 Hz, 8 Hz), 7.54 (td, 1H, J=8 Hz, 1 Hz), 7.43 (td, 1H, J=8 Hz, 1 Hz), 7.34 (dd, 1H, J=1 Hz, 8 Hz), 7.29 (s, 4H), 7.23 (dd, 1H, J=5 Hz, 8 Hz), 5.67 (s, 2H), 2.37~2.19 (m, 1H), 1.13~1.02 (m, 4H)

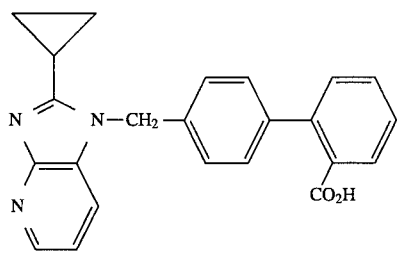

m.p.: 227°~229° C.

NMR (400 MHz, DMSO—d₆, δ value): 8.31 (dd, 1H, J=1 Hz, 5 Hz), 7.94 (dd, 1H, J=1 Hz, 8 Hz), 7.71 (dd, 1H, J=1 Hz, 8 Hz), 7.54 (td, 1H, J=8 Hz, 1 Hz), 7.43 (td, 1H, J=8 Hz, 1 Hz), 7.34 (dd, 1H, J=1 Hz, 8 Hz), 7.31 (d, 2H, J=8 Hz), 7.24 (d, 2H, J=8 Hz), 7.17 (dd, 1H, J=5 Hz, 8 Hz), 5.69 (s, 2H), 2.41~2.33 (m, 1H), 1.19~1.06 (m, 4H)

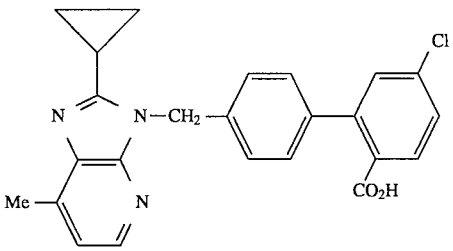

m.p.: 256°~259° C.

NMR (400 MHz, DMSO—d₆, δ value): 8.13 (d, 1H, J=5 Hz), 7.74 (d, 1H, J=8 Hz), 7.51 (dd, 1H, J=2Hz, 8 Hz), 7.40 (d, 1H, J=2Hz), 7.31 (d, 2H, J=8 Hz), 7.27 (d, 2H, J=8 Hz), 7.05 (d, 1H, J=5 Hz), 5.65 (s, 2H), 2.51 (s, 3H), 2.32~2.24 (m, 1H), 1.08~1.00 (m, 4H)

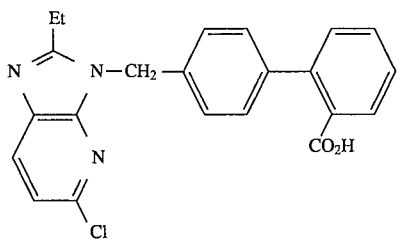

m.p.: 248°~251° C.

NMR (400 MHz, DMSO—d₆, δ value): 12.75 (bs, 1H), 8.10 (d, 1H, J=8 Hz), 7.72 (d, 1H, J=8 Hz), 7.55 (t, 1H, J=8 Hz), 7.44 (t, 1H, J=8 Hz), 7.37~7.32 (m, 2H), 7.31 (d, 2H, J=8 Hz), 7.18 (d, 2H, J=8 Hz), 5.53 (s, 2H), 2.87 (q, 2H, J=8 Hz), 1.28 (t, 3H, J=8 Hz)

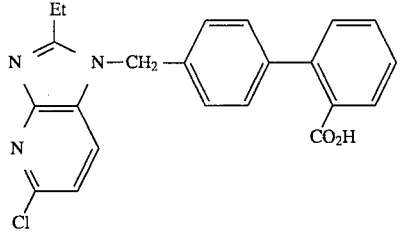

m.p.: 280°~282° C.

NMR (400 MHz, DMSO—d₆, δ value): 12.74 (bs, 1H), 8.06 (d, 1H, J=8 Hz), 7.71 (dd, 1H, J=1 Hz, 8 Hz), 7.55 (td, 1H, J=8 Hz, 1 Hz), 7.44 (td, 1H, J=8 Hz, 1 Hz), 7.33 (dd, 1H, J=1 Hz, 8 Hz), 7.32~7.28 (m, 3H), 7.16 (d, 2H, J=8 Hz), 5.60 (s, 2H), 2.93 (q, 2H, J=8 Hz), 1.30 (t, 3H, J=8 Hz)

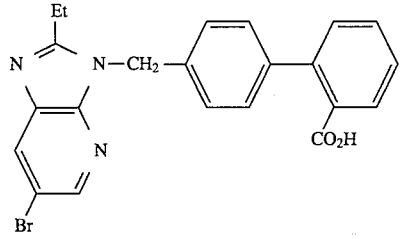

m.p.: 235°~237° C.

NMR (400 MHz, DMSO—d$_6$, δ value): 8.42 (d, 1H, J=2 Hz), 8.22 (d, 1H, J=2 Hz), 7.71 (dd, 1H, J=1 Hz, 8 Hz), 7.55 (td, 1H, J=8 Hz, 1 Hz), 7.44 (td, 1H, J=8 Hz, 1 Hz), 7.32 (dd, 1H, J=1 Hz, 8 Hz), 7.28 (d, 2H, J=8 Hz), 7.20 (d, 2H, J=8 Hz), 5.55 (s, 2H), 2.91 (q, 2H, J=8 Hz), 1.28 (t, 3H, J=8 Hz)

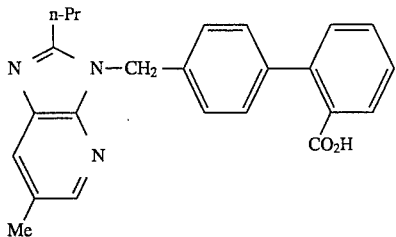

m.p.: 208°~210° C.

NMR (400 MHz, DMSO—d$_6$, δ value): 8.16 (d, 1H, J=2 Hz), 7.83 (d, 1H, J=2 Hz), 7.70 (dd, 1H, J=1 Hz, 8 Hz), 7.54 (td, 1H, J=8 Hz, 1 Hz), 7.43 (td, 1H, J=8 Hz, 1 Hz), 7.22 (dd, 1H, J=1 Hz, 8 Hz), 7.27 (d, 2H, J=8 Hz), 7.17 (d, 2H, J=8 Hz), 5.53 (s, 2H), 2.82 (t, 2H, J=8 Hz), 2.42 (s, 3H), 1.80~1.70 (m, 2H), 0.94 (t, 3H, J=8 Hz)

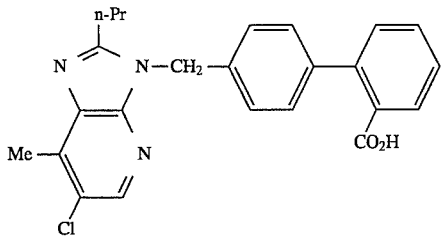

m.p.: 189°~191° C.

NMR (400 MHz, DMSO—d$_6$, δ value): 12.73 (bs, 1H), 8.31 (s, 1H), 7.71 (dd, 1H, J=1 Hz, 8 Hz), 7.55 (td, 1H, J=8 Hz, 1Hz), 7.44 (td, 1H, J=8 Hz, 1 Hz), 7.33 (dd, 1H, J=1 Hz, 8 Hz), 7.28 (d, 2H, J=8 Hz), 7.18 (d, 2H, J=8 Hz), 5.55 (s, 2H), 2.85 (t, 2H, J=8 Hz), 2.61 (s, 3H), 1.80~1.69 (m, 2H), 0.95 (t, 3H, J=8 Hz)

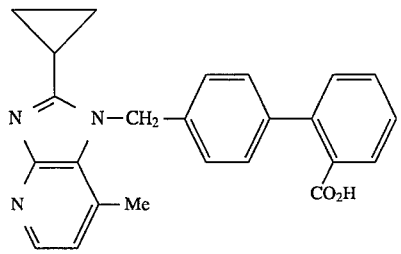

NMR (400 MHz, DMSO—d$_6$, δ value): 8.16 (d, 1H, J=5 Hz), 7.70 (d, 1H, J=8 Hz), 7.54 (t, 1H, J=8 Hz), 7.43 (t, 1H, J=8 Hz), 7.35 (d, 1H, J=8 Hz), 7.32 (d, 2H, J=8 Hz), 7.02 (d, 2H, J=8 Hz), 6.90 (d, 1H, J=5 Hz), 5.83 (s, 2H), 2.44 (s, 3H), 2.31~2.23 (m, 1H), 1.15~1.02 (m, 4H)

We claim:

1. A compound having the formula

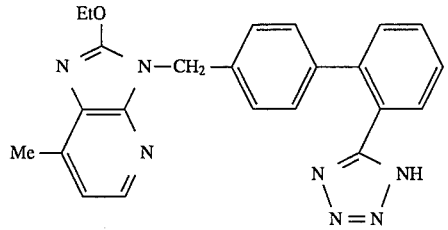

or a pharmacologically acceptable salt thereof.

2. A pharmacological composition comprising an antihypertensive or anticardiac failing amount of the biphenylmethane derivative or a pharmacologically acceptable salt thereof as defined in claim 1 and a pharmacologically acceptable carrier.

3. A method for preventing and treating hypertension by administering an effective antihypertensive amount of the biphenylmethane derivative or a pharmacologically acceptable salt thereof as defined in claim 1 to a patient in need thereof.

4. A method for preventing and treating cardiac failure by administering an effective anticardiac failing amount of the biphenylmethane derivative or a pharmacologically acceptable salt thereof as defined in claim 1 to a patient in need thereof.

* * * * *